US010464878B2

(12) United States Patent
Zhang et al.

(10) Patent No.: US 10,464,878 B2
(45) Date of Patent: *Nov. 5, 2019

(54) TREPROSTINIL DERIVATIVES AND COMPOSITIONS AND USES THEREOF

(71) Applicant: CORSAIR PHARMA, INC., South San Francisco, CA (US)

(72) Inventors: Xiaoming Zhang, Sunnyvale, CA (US); Meenakshi S. Venkatraman, Fremont, CA (US); Cyrus K. Becker, Pleasanton, CA (US)

(73) Assignee: Corsair Pharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,566

(22) Filed: Jul. 19, 2018

(65) Prior Publication Data

US 2019/0010112 A1 Jan. 10, 2019

Related U.S. Application Data

(63) Continuation of application No. 15/617,243, filed on Jun. 8, 2017, now Pat. No. 10,053,414, which is a continuation of application No. 15/178,637, filed on Jun. 10, 2016, now Pat. No. 9,701,616, which is a continuation of application No. 14/742,544, filed on Jun. 17, 2015, now Pat. No. 9,394,227.

(51) Int. Cl.
| | |
|---|---|
| *C07C 69/734* | (2006.01) |
| *C07C 69/732* | (2006.01) |
| *A61K 31/216* | (2006.01) |
| *C07C 69/013* | (2006.01) |
| *C07C 69/26* | (2006.01) |
| *C07C 69/675* | (2006.01) |
| *C07C 69/708* | (2006.01) |
| *C07C 69/712* | (2006.01) |
| *C07C 69/96* | (2006.01) |
| *C07D 303/48* | (2006.01) |
| *A61K 9/00* | (2006.01) |
| *A61K 9/70* | (2006.01) |
| *A61K 45/06* | (2006.01) |

(52) U.S. Cl.
CPC .......... *C07C 69/734* (2013.01); *A61K 9/0014* (2013.01); *A61K 9/7023* (2013.01); *A61K 31/216* (2013.01); *A61K 45/06* (2013.01); *C07C 69/013* (2013.01); *C07C 69/26* (2013.01); *C07C 69/675* (2013.01); *C07C 69/708* (2013.01); *C07C 69/712* (2013.01); *C07C 69/732* (2013.01); *C07C 69/96* (2013.01); *C07D 303/48* (2013.01); *C07C 2601/04* (2017.05); *C07C 2601/14* (2017.05); *C07C 2603/14* (2017.05)

(58) Field of Classification Search
CPC .... C07C 69/734; C07C 69/732; A61K 31/216
See application file for complete search history.

(56) References Cited

U.S. PATENT DOCUMENTS

| | | |
|---|---|---|
| 3,598,122 A | 8/1971 | Zaffaroni |
| 4,144,317 A | 3/1979 | Higuchi et al. |
| 4,201,211 A | 5/1980 | Chandrasekaran et al. |
| 4,262,003 A | 4/1981 | Urquhart et al. |
| 4,306,075 A | 12/1981 | Aristoff |
| 4,306,076 A | 12/1981 | Nelson |
| 4,338,457 A | 7/1982 | Aristoff |
| 4,349,689 A | 9/1982 | Aristoff |
| 4,379,454 A | 4/1983 | Campbell et al. |
| 4,420,632 A | 12/1983 | Aristoff |
| 4,525,586 A | 6/1985 | Aristoff |
| 4,668,814 A | 5/1987 | Aristoff |
| 4,683,330 A | 7/1987 | Aristoff |
| 5,028,628 A | 7/1991 | Tadepalli et al. |
| 5,071,657 A | 12/1991 | Oloff et al. |
| 5,088,977 A | 2/1992 | Sibalis |
| 5,153,222 A | 10/1992 | Tadepalli et al. |
| 5,328,453 A | 7/1994 | Sibalis |
| 5,797,898 A | 8/1998 | Santini, Jr. et al. |
| 5,853,751 A | 12/1998 | Masiz |
| 5,972,974 A | 10/1999 | Keenan |
| 6,242,482 B1 | 6/2001 | Shorr et al. |
| 6,264,990 B1 | 7/2001 | Knepp et al. |
| 6,635,274 B1 | 10/2003 | Masiz et al. |
| 6,638,528 B1 | 10/2003 | Kanios |
| 6,700,025 B2 | 3/2004 | Moriarty et al. |
| 6,809,223 B2 | 10/2004 | Moriarty et al. |
| 7,199,157 B2 | 4/2007 | Wade et al. |

(Continued)

FOREIGN PATENT DOCUMENTS

| | | |
|---|---|---|
| EP | 1628654 A2 | 3/2006 |
| EP | 2252570 A1 | 11/2010 |

(Continued)

OTHER PUBLICATIONS

EP 0496548 A1 + ESR, Jul. 29, 1992, P. Fuchs.
WO 00/57701 A1 + ISR, Oct. 5, 2000, R. Shorr et al.
WO 02/053517 A3 (ISR), Jul. 11, 2002, R. Moriarty et al.
WO 03/049676 A3 (ISR), Jun. 19, 2003, R. Shorr et al.
WO 2005/007081 A3 (ISR), Jan. 27, 2005, K. Phares et al.
WO 2005/058329 A1 + ISR, Jun. 30, 2005, M. Wade et al.
WO 2005/058303 A1 + ISR, Jun. 30, 2005, M. Wade et al.
WO 2007/100902 A3 (ISR), Sep. 7, 2007, S. Charles.
WO 2007/127216 A3 (ISR), Nov. 8, 2007, A. Kidane et al.
WO 2007/134292 A3 (ISR), Nov. 22, 2007, H. Olschewski et al.
WO 2008/002929 A3 (ISR), Jan. 3, 2008, R. Bond.

(Continued)

*Primary Examiner* — Matthew P Coughlin
(74) *Attorney, Agent, or Firm* — The Marbury Law Group, PLLC

(57) ABSTRACT

The present disclosure provides treprostinil derivatives that can act as prodrugs of treprostinil. The treprostinil derivatives can be used to treat any conditions responsive to treatment with treprostinil, including pulmonary hypertension, such as pulmonary arterial hypertension.

16 Claims, No Drawings

(56) References Cited

U.S. PATENT DOCUMENTS

| | | |
|---|---|---|
| 7,375,139 B2 | 5/2008 | Aldred |
| 7,384,978 B2 | 6/2008 | Phares et al. |
| 7,417,070 B2 | 8/2008 | Phares et al. |
| 7,537,590 B2 | 5/2009 | Santini, Jr. et al. |
| 7,544,713 B2 | 6/2009 | Phares et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,410,169 B2 | 4/2013 | Phares et al. |
| 8,435,944 B2 | 5/2013 | Dipeitro et al. |
| 8,481,782 B2 | 7/2013 | Batra et al. |
| 8,497,393 B2 | 7/2013 | Batra et al. |
| 8,519,178 B2 | 8/2013 | Hogan et al. |
| 8,524,939 B2 | 9/2013 | Wei et al. |
| 8,536,363 B2 | 9/2013 | Phares et al. |
| 8,591,941 B2 | 11/2013 | Kanios et al. |
| 8,609,134 B2 | 12/2013 | Yoneto et al. |
| 8,617,591 B2 | 12/2013 | Schacht et al. |
| 8,658,837 B2 | 2/2014 | Wei et al. |
| 8,747,897 B2 | 6/2014 | Kidane et al. |
| 8,748,657 B2 | 6/2014 | Batra et al. |
| 8,809,334 B2 | 8/2014 | Clozel |
| 8,846,021 B2 | 9/2014 | Charles |
| 8,877,710 B2 | 11/2014 | Johansson et al. |
| 8,940,930 B2 | 1/2015 | Batra et al. |
| 8,957,240 B2 | 2/2015 | Hogan et al. |
| 9,050,311 B2 | 6/2015 | Batra et al. |
| 9,102,660 B2 | 8/2015 | Batra et al. |
| 9,156,786 B2 | 10/2015 | Batra et al. |
| 9,199,908 B2 | 12/2015 | Batra et al. |
| 9,255,064 B2 | 2/2016 | Malinin et al. |
| 9,278,901 B2 | 3/2016 | Batra et al. |
| 9,346,738 B2 | 5/2016 | Ghone et al. |
| 9,371,264 B2 | 6/2016 | Becker et al. |
| 9,394,227 B1 * | 7/2016 | Zhang .................. C07C 69/732 |
| 9,422,223 B2 | 8/2016 | Batra et al. |
| 9,469,600 B2 | 10/2016 | Malinin et al. |
| 9,505,704 B2 | 11/2016 | Gao et al. |
| 9,505,737 B2 * | 11/2016 | Becker .................. C07C 59/72 |
| 9,701,616 B2 * | 7/2017 | Zhang .................. C07C 69/732 |
| 9,845,305 B2 * | 12/2017 | Becker .................. C07C 59/72 |
| 10,053,414 B2 * | 8/2018 | Zhang .................. C07C 69/732 |
| 2002/0099034 A1 | 7/2002 | Moriarty et al. |
| 2003/0108512 A1 | 6/2003 | Shorr et al. |
| 2004/0176645 A1 | 9/2004 | Moriarty et al. |
| 2005/0080140 A1 | 4/2005 | Hatae et al. |
| 2005/0085540 A1 | 4/2005 | Phares et al. |
| 2005/0165110 A1 | 7/2005 | Wade et al. |
| 2005/0165111 A1 * | 7/2005 | Wade .................. A61K 31/191 514/573 |
| 2005/0282901 A1 | 12/2005 | Phares et al. |
| 2007/0078095 A1 | 4/2007 | Phares et al. |
| 2007/0078182 A1 | 4/2007 | Phares et al. |
| 2007/0082948 A1 | 4/2007 | Phares et al. |
| 2007/0254032 A1 | 11/2007 | Kidane et al. |
| 2008/0200449 A1 | 8/2008 | Olschewski et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0163738 A1 | 6/2009 | Batra et al. |
| 2010/0076083 A1 | 3/2010 | Olschewski et al. |
| 2010/0166700 A1 | 7/2010 | Charles |
| 2010/0282622 A1 | 11/2010 | Phares |
| 2010/0324313 A1 | 12/2010 | Hogan et al. |
| 2011/0092599 A1 | 4/2011 | Wade et al. |
| 2011/0118213 A1 | 5/2011 | Phares et al. |
| 2011/0136818 A1 | 6/2011 | Clozel |
| 2011/0268732 A1 | 11/2011 | Johansson |
| 2011/0294815 A1 | 12/2011 | Harbeson |
| 2011/0319641 A1 | 12/2011 | Batra et al. |
| 2012/0010159 A1 | 1/2012 | Rothblatt et al. |
| 2012/0129941 A1 | 5/2012 | Wade et al. |
| 2012/0184622 A1 | 7/2012 | Freissmuth et al. |
| 2012/0190888 A1 | 7/2012 | Batra et al. |
| 2012/0197041 A1 | 8/2012 | Batra et al. |
| 2012/0216801 A1 | 8/2012 | Olschewski et al. |
| 2012/0283470 A1 | 11/2012 | Batra et al. |
| 2012/0295980 A1 | 11/2012 | Phares et al. |
| 2013/0040898 A1 | 2/2013 | Johansson |
| 2013/0053581 A1 | 2/2013 | Wei et al. |
| 2013/0096200 A1 | 4/2013 | Wade et al. |
| 2013/0165389 A1 | 6/2013 | Schellenberger |
| 2013/0184295 A1 | 7/2013 | Sprague et al. |
| 2013/0261187 A1 | 10/2013 | Phares et al. |
| 2013/0267734 A1 | 10/2013 | Batra et al. |
| 2013/0274261 A1 | 10/2013 | Sands |
| 2013/0289304 A1 | 10/2013 | Batra et al. |
| 2013/0317245 A1 | 11/2013 | Wei et al. |
| 2013/0317249 A1 | 11/2013 | Hogan et al. |
| 2013/0331593 A1 | 12/2013 | McGowan et al. |
| 2013/0337534 A1 | 12/2013 | Charles |
| 2013/0344038 A1 | 12/2013 | Freissmuth et al. |
| 2014/0018430 A1 | 1/2014 | Freissmuth et al. |
| 2014/0018431 A1 | 1/2014 | Wade et al. |
| 2014/0024856 A1 | 1/2014 | Giust et al. |
| 2014/0044797 A1 | 2/2014 | Johansson et al. |
| 2014/0193379 A1 | 7/2014 | Jeffs et al. |
| 2014/0249093 A1 | 9/2014 | Vetter et al. |
| 2014/0256730 A1 | 9/2014 | Becker et al. |
| 2014/0275616 A1 | 9/2014 | Batra et al. |
| 2014/0288314 A1 | 9/2014 | Batra et al. |
| 2014/0296150 A1 | 10/2014 | Hersel et al. |
| 2014/0303245 A1 | 10/2014 | Sprogoee et al. |
| 2014/0303252 A1 | 10/2014 | Kidane et al. |
| 2014/0322207 A1 | 10/2014 | Johansson |
| 2014/0323567 A1 | 10/2014 | Laing |
| 2014/0329824 A1 | 11/2014 | Clozel |
| 2015/0005374 A1 | 1/2015 | Phares et al. |
| 2015/0050714 A1 | 2/2015 | Charles |
| 2015/0057325 A1 | 2/2015 | Johansson et al. |
| 2015/0087688 A1 | 3/2015 | Hersel et al. |
| 2015/0105582 A1 | 4/2015 | Batra et al. |
| 2015/0126761 A1 | 5/2015 | Jain et al. |
| 2015/0126764 A1 | 5/2015 | Hogan et al. |
| 2015/0148414 A1 | 5/2015 | Malinin et al. |
| 2015/0166503 A1 | 6/2015 | Becker et al. |
| 2015/0175529 A1 | 6/2015 | Malinin et al. |
| 2015/0259274 A1 | 9/2015 | Phares et al. |
| 2015/0299091 A1 | 10/2015 | Batra et al. |
| 2015/0376106 A1 | 12/2015 | Batra et al. |
| 2016/0030371 A1 | 2/2016 | Batra et al. |
| 2016/0051505 A1 | 2/2016 | Batra et al. |
| 2016/0152548 A1 | 6/2016 | Gao et al. |
| 2016/0243064 A1 | 8/2016 | Trehan et al. |
| 2016/0256425 A1 | 9/2016 | Malinin et al. |
| 2016/0289158 A1 | 10/2016 | Chambournier et al. |
| 2016/0318844 A1 | 11/2016 | Malinin et al. |
| 2016/0355455 A1 | 12/2016 | Batra et al. |
| 2016/0368854 A1 | 12/2016 | Zhang et al. |
| 2016/0368855 A1 | 12/2016 | Zhang et al. |
| 2016/0368889 A1 | 12/2016 | Becker et al. |

FOREIGN PATENT DOCUMENTS

| | | |
|---|---|---|
| EP | 2427054 A1 | 3/2012 |
| EP | 2674413 A1 | 12/2013 |
| EP | 2792353 A2 | 10/2014 |
| EP | 2792353 A3 | 10/2014 |
| EP | 2841109 A1 | 3/2015 |
| EP | 2861554 A2 | 4/2015 |
| EP | 2978313 A1 | 2/2016 |
| EP | 3060041 A2 | 8/2016 |
| EP | 3068752 A1 | 9/2016 |
| WO | WO 01/93862 A1 | 12/2001 |
| WO | WO 02/053517 A2 | 7/2002 |
| WO | WO 03/049676 A2 | 6/2003 |
| WO | WO 2005/007081 | 1/2005 |
| WO | WO 2007/100902 A2 | 9/2007 |
| WO | WO 2007/127216 A2 | 11/2007 |
| WO | WO 2007/134292 A2 | 11/2007 |
| WO | WO 2008/002929 A2 | 1/2008 |
| WO | WO 2008/049000 A2 | 4/2008 |
| WO | WO 2009/152160 | 12/2009 |

(56) References Cited

FOREIGN PATENT DOCUMENTS

| | | | |
|---|---|---|---|
| WO | WO 2010/018549 A2 | 2/2010 | |
| WO | WO 2010/075861 A2 | 7/2010 | |
| WO | WO 2011/005505 A2 | 1/2011 | |
| WO | WO 2011/123813 A2 | 10/2011 | |
| WO | WO 2011/134478 A2 | 11/2011 | |
| WO | WO 2012/009816 | 1/2012 | |
| WO | WO 2013/022846 | 2/2013 | |
| WO | WO 2013/024051 | 2/2013 | |
| WO | WO 2013/024052 | 2/2013 | |
| WO | WO 2013/024053 A1 | 2/2013 | |
| WO | WO 2013/174848 A2 | 11/2013 | |
| WO | WO 2014/089385 A2 | 6/2014 | |
| WO | WO 2014/110491 A1 | 7/2014 | |
| WO | WO-2014110491 A1 * | 7/2014 | ........... C07C 69/712 |
| WO | WO 2014/203278 A2 | 12/2014 | |
| WO | WO 2015061720 A2 | 4/2015 | |
| WO | WO 2015073314 A1 | 5/2015 | |
| WO | WO 2015061720 A3 | 6/2015 | |
| WO | WO 2015138423 A1 | 9/2015 | |
| WO | WO 2015138423 A9 | 11/2015 | |
| WO | WO 2016010538 A1 | 1/2016 | |
| WO | WO 2016055819 A1 | 4/2016 | |
| WO | WO 2016081658 A1 | 5/2016 | |
| WO | WO 2016120311 A1 | 8/2016 | |
| WO | WO 2016176555 A1 | 11/2016 | |
| WO | WO 2016205202 A1 | 12/2016 | |

OTHER PUBLICATIONS

WO 2008/049000 A3 (ISR), Apr. 24, 2008, R. Roscigno et al.
WO 2008/098196 A1 + ISR, Aug. 14, 2008, M. Wade et al.
WO 2009/078965 A1 + ISR, Jun. 25, 2009, H. Batra et al.
WO 2009/158010 A1 + ISR, Dec. 30, 2009, S. Harbeson.
WO 2010/018549 A3 (ISR), Feb. 18, 2010, M. Clozel.
WO 2010/075861 A3 (ISR), Jul. 8, 2010, P. Johansson.
WO 2010/129757 A1 + ISR, Nov. 11, 2010, K. Phares.
WO 2011/005505 A3 (ISR), Jan. 13, 2011, R. Hogan et al.
WO 2011/015630 A1 + ISR, Feb. 10, 2011, M. Freissmuth et al.
WO 2011/123813 A3 (ISR), Oct. 6, 2011, V. Schenenberger et al.
WO 2011/134478 A3 (ISR), Nov. 3, 2011, P. Johansson.
WO 2011/153363 A1 + ISR, Dec. 8, 2011, H. Batra et al.
WO 2012/006273 A1 + ISR, Jan. 12, 2012, M. Rothblatt et al.
WO 2012/088607 A1 + ISR, Jul. 5, 2012, W. Giust et al.
WO 2012/095511 A1 + ISR, Jul. 19, 2012, M. Freissmuth et al.
WO 2012/107364 A1 + ISR, Aug. 16, 2012, M. Freissmuth.
WO 2012/107363 A1 + ISR, Aug. 16, 2012, M. Freissmuth et al.
WO 2012/143012 A1 + ISR, Oct. 26, 2012, P. Johansson et al.
WO 2013/024053 A1 + ISR, Feb. 21, 2013, D. Vetter et al.
WO 2013/143548 A1 + ISR, Oct. 3, 2013, P. Johansson et al.
WO 2013/160340 A1 + ISR, Oct. 31, 2013, U. Hersel et al.
WO 2013/174848 A3 (ISR), Nov. 28, 2013, N. Jain et al.
WO 2014/089385 A3 (ISR), Jun. 12, 2014, K. Hering et al.
WO 2014/022373 A1 + ISR, Feb. 6, 2014, R. Jeffs et al.
WO 2014/110094 A1 + ISR, Jul. 17, 2014, R. Jeffs et al.
WO 2014/150203 A1 + ISR, Sep. 25, 2014, H. Batra et al.
WO 2014/160638 A1 + ISR, Oct. 2, 2014, H. Batra et al.
WO 2014/179295 A1 + ISR, Nov. 6, 2014, P. Laing.
WO 2014/203278 A3 (ISR), Dec. 24, 2014, S. Rajan et al.
Cochrane et al., "A macrolactonization approach to the total synthesis of the antimicrobial cyclic depsipeptide LI-F04a and dlastereosiomeric analogues", Beilstein Journal of Organic Chemistry, vol. 8, 1344-1351 (2012).
Hea-Jeong Doh et al., Synthesis and Evaluation of Ketorolac Ester Prodrugs for Transdermal Delivery, J. of Pharmaceutical Sciences, vol. 92, No. 5, May 2003.
Gannes L Z et al., "Natural abundance variations in stable isotopes and their potential uses in animal physiological ecology", Comp Biochem Physiol Mol Integr Physiol, 119:725-737 (1998).
*Handbook of Reagents of Organic Synthesi*: Activating Agents and Protecting Groups, Pearson and Rousch (Ed.), John Wiley & Sons (1999).
Paudel et al., "Challenges and Opportunities in dermal/transdermal Delivery", Ther Deliv., 2010, 1, 109-131.
Rautio et al., "Prodrugs: design and clinical applications", Nature Reviews: Drug Discovery 2008, 7, 2008, 255-270.
Schanz, et al., "Topical treatment of erectile dysfunction with prostaglandin E1 ethyl ester", J. Dtsch Dermatol. Ges., 7:1055-59 (2009).
Shiina, Isamu, "Total Synthesis of Natural 8- and 9-Membered lactones: Recent Advancements in Medium Sized Ring Formations", Chemical Reviews 107, 239-273 (2007).
Smith, Michael B. et al. "March's Advanced Organic Chemistry: Reactions, Mechanisms and Structure", 6th Ed., Wiley & Sons (2007).
Thayer, Chemical & Engineering News, Jun. 18, 2007, vol. 85. Issue 25, pp. 17-30.
Wada E et al., "Natural abundance of carbon, nitrogen, and hydrogen isotope ratios in biogenic substances: present and future," Seikagaku, 66:15-29 (English portions included). (1994).
Wuts, Peter G. and Greene, Theodora W., "Greene's Protective Groups in Organic Synthesis", 4th Ed., John Wiley & Sons (2007).
Invitation to pay additional fees with partial international search report received in connection with international patent application No. PCT/US2014/046920; dated Sep. 11, 2014.
International Search Report and Written Opinion received in connection with international patent application No. PCT/US2014/011260; dated May 6, 2014.
Findlay et al., Prostaglandins, Leukotrienes and Essential Fatty Acids, vol. 48, Issue No. 2, 1993, pp. 167-174.
Geiger et al., Biomaterials, vol. 31, Issue No. 10, 2010, pp. 2903-2911.
Zhang et al., "Treprostinil Derivatives and Compositions and Uses Thereof" U.S. Appl. No. 14/829,180, filed Aug. 18, 2015.
International Search Report and Written Opinion received in connection with international application No. PCT/US2016/037383; dated Nov. 23, 2016.

* cited by examiner

TREPROSTINIL DERIVATIVES AND COMPOSITIONS AND USES THEREOF

CROSS REFERENCE TO RELATED APPLICATIONS

The present application is a continuation of and claims priority to and the benefit of U.S. application Ser. No. 14/742,544 filed on Jun. 17, 2015, whose entire disclosure is incorporated herein by reference for all purposes.

BACKGROUND OF THE DISCLOSURE

Pulmonary hypertension (PH), which includes pulmonary arterial hypertension (PAH), is a disease that can result in death and is characterized by increased pulmonary artery pressure and pulmonary vascular resistance. Some drugs that can be used to treat PH or PAH cannot be effectively administered orally for various reasons and are generally administered via subcutaneous, intravenous or intramuscular routes. These routes of administration generally require intervention by a healthcare professional, and can entail considerable discomfort as well as potential local trauma to the patient.

One example of such a drug is treprostinil. Treprostinil as the free acid has an absolute oral bioavailability of less than 10% and a very short systemic half-life due to significant metabolism. Treprostinil can be administered in an inhaled form, but about 50% of PAH patients cannot take inhaled treprostinil due to irritation. Treprostinil (also called Compound A herein) has the following structure:

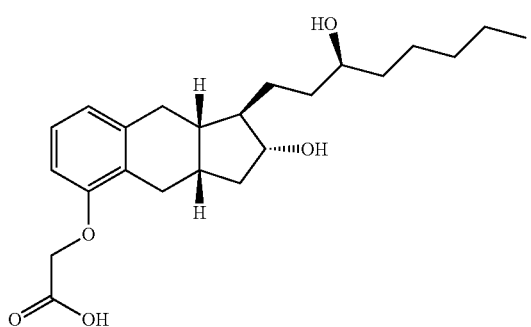 [SMILES: CCCCC[C@H](O)CC[C@@H]1[C@H]2Cc3cccc(OCC(=O)O)c3C[C@H]2C[C@H]1O]

Treprostinil can exist as a salt, such as a sodium or diethanolamine salt.

SUMMARY OF THE DISCLOSURE

The present disclosure describes treprostinil derivatives that can act as prodrugs and provide increased systemic availability of treprostinil. In some embodiments, treprostinil derivatives have the structure of Formula (I):

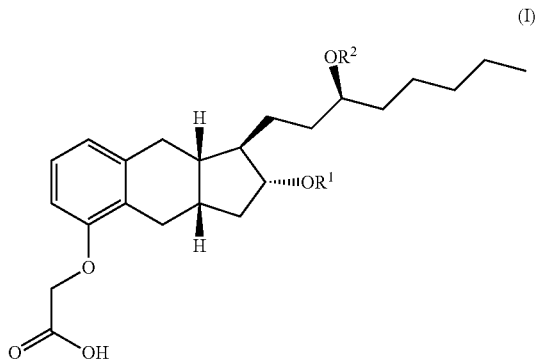

wherein $R^1$ and $R^2$ independently are hydrogen,

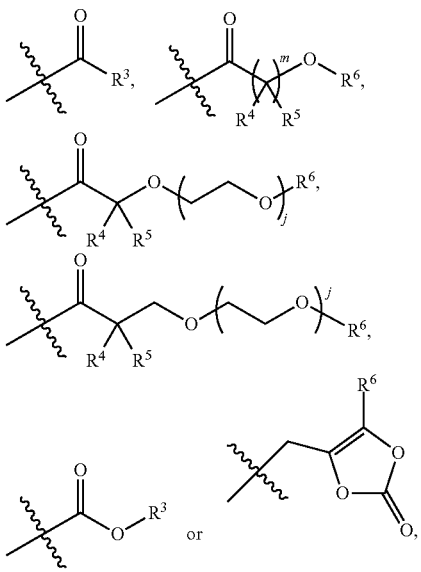

and $R^3$, $R^4$, $R^5$, $R^6$, j and m are as described herein, or pharmaceutically acceptable salts, solvates, hydrates, clathrates, polymorphs or stereoisomers thereof, with the proviso that:
both $R^1$ and $R^2$ are not hydrogen;
neither —$OR^1$ nor —$OR^2$ forms an acetate;
neither —$OR^1$ nor —$OR^2$ forms a substituted cyclohexane-ester; and
neither —$OR^1$ nor —$OR^2$ forms an ester with or of an amino acid (protected or unprotected), a peptide or a protein.

In other embodiments, treprostinil derivatives have the structure of Formula (II):

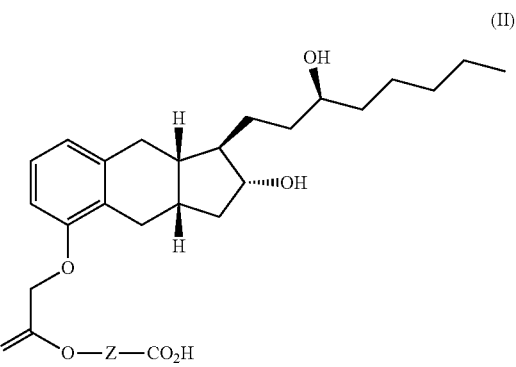

wherein —O—Z—$CO_2H$

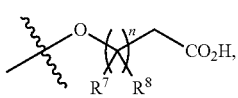

—O-heteroalkyl-$CO_2H$, —O-cyclyl-$CO_2H$, —O—$CH_2$-cyclyl-$CO_2H$, —O-cyclyl-$CH_2$—$CO_2H$, or —O—$CH_2$-cyclyl-$CH_2$—$CO_2H$, each of which may optionally be substituted, and -cyclyl-, -heteroalkyl-, $R^7$, $R^8$ and n are as described herein, with the proviso that:
—O—Z—$CO_2H$ is not

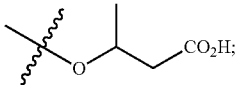 [SMILES: *OC(C)CC(=O)O]

and

—O—Z—CO₂H does not contain a sugar moiety.

The treprostinil derivatives can be used to treat any conditions responsive to treatment with treprostinil, including pulmonary hypertension (e.g., PAH). In some embodiments, the treprostinil derivatives are administered topically, such as transdermally (e.g., via a transdermal patch).

DETAILED DESCRIPTION OF THE DISCLOSURE

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act or step, the order of the acts or steps of the method is not necessarily limited to the order in which the acts or steps of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. DEFINITIONS

As used in the specification and the appended claims, the indefinite articles "a" and "an" and the definite article "the" can include plural referents as well as singular referents unless specifically stated otherwise.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within 10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "pharmaceutically acceptable" refers to a substance (e.g., an active ingredient or an excipient) that is suitable for use in contact with the tissues and organs of a subject without excessive irritation, allergic response, immunogenecity and toxicity, is commensurate with a reasonable benefit/risk ratio, and is effective for its intended use. A "pharmaceutically acceptable" excipient or carrier of a pharmaceutical composition is also compatible with the other ingredients of the composition.

The term "therapeutically effective amount" refers to an amount of a compound that, when administered to a subject, is sufficient to prevent development of, or to alleviate to some extent, the medical condition being treated or one or more symptoms associated with the condition. The term "therapeutically effective amount" also refers to an amount of a compound that is sufficient to elicit the biological or medical response of a cell, tissue, organ, system, animal or human which is sought by a researcher, veterinarian, medical doctor or clinician.

The terms "treat", "treating", and "treatment" include alleviating or abrogating a medical condition or one or more symptoms associated with the condition, and alleviating or eradicating one or more causes of the condition. Reference to "treatment" of a condition is intended to include prevention of the condition. The terms "prevent", "preventing", and "prevention" include precluding or delaying the onset of a medical condition or one or more symptoms associated with the condition, precluding a subject from acquiring a condition, and reducing a subject's risk of acquiring a condition. The term "medical conditions" includes diseases and disorders.

The term "subject" refers to an animal, including but not limited to a mammal, such as a primate (e.g., a human, a chimpanzee and a monkey), a rodent (e.g., a rat, a mouse, a gerbil and a hamster), a lagomorph (e.g., a rabbit), a swine (e.g., a pig), an equine (e.g., a horse), a canine (e.g., a dog) and a feline (e.g., a cat). The terms "subject" and "patient" are used interchangeably herein in reference to, e.g., a mammalian subject, such as a human subject.

The term "compound" encompasses salts, solvates, hydrates, clathrates and polymorphs of that compound. A "solvate" of a compound includes a stoichiometric or non-stoichiometric amount of a solvent (e.g., water, acetone or an alcohol [e.g., ethanol]), bound non-covalently to the compound. A "hydrate" of a compound includes a stoichiometric or non-stoichiometric amount of water bound non-covalently to the compound. A "clathrate" of a compound contains molecules of a substance (e.g., a solvent) enclosed in the crystal structure of the compound. A "polymorph" of a compound is a crystalline form of the compound. The specific recitation of "salt", "solvate", "hydrate", "clathrate" or "polymorph" with respect to a compound in certain instances of the disclosure shall not be interpreted as an intended omission of any of these forms in other instances of the disclosure where the term "compound" is used without recitation of any of these forms.

The terms "halogen", "halide" and "halo" refer to fluoride, chloride, bromide and iodide.

The term "alkyl" refers to a linear or branched, saturated monovalent hydrocarbon radical, wherein the alkyl group may optionally be substituted with one or more substituents as described herein. In certain embodiments, an alkyl group is a linear saturated monovalent hydrocarbon radical that has 1 to 20 ($C_{1-20}$), 1 to 10 ($C_{1-10}$), or 1 to 6 ($C_{1-6}$) carbon atoms, or is a branched saturated monovalent hydrocarbon radical that has 3 to 20 ($C_{3-20}$), 3 to 10 ($C_{3-10}$), or 3 to 6 ($C_{3-6}$) carbon atoms. As an example, the term "$C_{1-6}$ alkyl" refers to a linear saturated monovalent hydrocarbon radical of 1 to 6 carbon atoms or a branched saturated monovalent hydrocarbon radical of 3 to 6 carbon atoms. Linear $C_{1-6}$ and branched $C_{3-6}$ alkyl groups may also be referred to as "lower alkyl". Non-limiting examples of alkyl groups include methyl, ethyl, propyl (including all isomeric forms, such as n-propyl and isopropyl), butyl (including all isomeric forms, such as n-butyl, isobutyl, sec-butyl and tert-butyl), pentyl (including all isomeric forms, such as n-pentyl), and hexyl (including all isomeric forms, such as n-hexyl).

The terms "alkylene" and "-alkyl-" refer to a divalent alkyl group, which may optionally be substituted with one or more substituents as described herein.

The term "heteroalkyl" refers to a linear or branched, saturated monovalent hydrocarbon group containing one or more heteroatoms independently selected from O, N and S. The terms "heteroalkylene" and "-heteroalkyl-" refer to a divalent heteroalkyl group. A heteroalkyl group and a -heteroalkyl- group may optionally be substituted with one or more substituents as described herein. Examples of heteroalkyl and -heteroalkyl- groups include without limitation —(CH$_2$)$_2$—(O or S)—CH$_2$CH$_3$ and —(CH$_2$)$_2$—(O or S)—(CH$_2$)$_2$—.

The term "alkoxy" refers to an —O-alkyl group, which may optionally be substituted with one or more substituents as described herein.

The term "-alkylaryl" refers to an alkyl group that is substituted with one or more aryl groups. An -alkylaryl group may optionally be substituted with one or more additional substituents as described herein.

The term "cycloalkyl" refers to a cyclic saturated, bridged or non-bridged monovalent hydrocarbon radical, which may optionally be substituted with one or more substituents as described herein. In certain embodiments, a cycloalkyl group has from 3 to 10 ($C_{3-10}$), or from 3 to 8 ($C_{3-8}$), or from 3 to 6 ($C_{3-6}$) carbon atoms. Non-limiting examples of cycloalkyl groups include cyclopropyl, cyclobutyl, cyclopentyl, cyclohexyl, cycloheptyl, cyclooctyl, norbornyl, decalinyl and adamantyl. The term "-cycloalkyl-" refers to a divalent cycloalkyl group, which may optionally be substituted with one or more substituents as described herein.

The terms "heterocyclyl" and "heterocyclic" refer to a monocyclic non-aromatic group or a multicyclic group that contains at least one non-aromatic ring, wherein at least one non-aromatic ring contains one or more heteroatoms independently selected from O, N and S. The non-aromatic ring containing one or more heteroatoms may be attached or fused to one or more saturated, partially unsaturated or aromatic rings. In certain embodiments, a heterocyclyl or heterocyclic group has from 3 to 15, or 3 to 12, or 3 to 10, or 3 to 8, or 3 to 6 ring atoms. In some embodiments, a heterocyclyl or heterocyclic group is a monocyclic, bicyclic or tricyclic ring system, which may include a fused or bridged ring system, and in which nitrogen or sulfur atoms may optionally be oxidized, nitrogen atoms may optionally be quaternized, and one or more rings may be fully or partially saturated, or aromatic. A heterocyclyl or heterocyclic group may be attached to the main structure at any heteroatom or carbon atom which results in the creation of a stable compound. Examples of heterocyclyl or heterocyclic groups include without limitation azepinyl, azetidinyl, aziridinyl, benzodioxanyl, benzodioxolyl, benzofuranonyl, benzopyranonyl, benzopyranyl, benzotetrahydrofuranyl, benzotetrahydrothienyl, benzothiopyranyl, β-carbolinyl, chromanyl, decahydroisoquinolinyl, dihydrobenzisothiazinyl, dihydrobenzisoxazinyl, dihydrofuryl, dihydropyranyl, dihydropyrazinyl, dihydropyridinyl, dihydropyrazolyl, dihydropyrimidinyl, dihydropyrrolyl, dioxolanyl, dithianyl, furanonyl, imidazolidinyl, imidazolinyl, indolinyl, indolizinyl, isobenzotetrahydrofuranyl, isobenzotetrahydrothienyl, isochromanyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrrolidinyl, pyrrolinyl, quinuclidinyl, tetrahydrofuryl, tetrahydrofuranyl (oxolanyl), tetrahydroisoquinolinyl, tetrahydropyranyl, tetrahydrothienyl (tetrahydrothiophenyl, thiolanyl), thiamorpholinyl (thiomorpholinyl), thiazolidinyl and 1,3,5-trithianyl. The term "-heterocyclyl" refers to a divalent heterocyclyl group. A heterocyclyl or heterocyclic group, and a -heterocyclyl- group, may optionally be substituted with one or more substituents as described herein.

The term "aryl" refers to a monocyclic aromatic hydrocarbon group or a multicyclic group that contains at least one aromatic hydrocarbon ring. In certain embodiments, an aryl group has from 6 to 15, or 6 to 12, or 6 to 10 ring atoms. Non-limiting examples of aryl groups include phenyl, naphthyl, fluorenyl, azulenyl, anthryl, phenanthryl, biphenyl and terphenyl. The aromatic hydrocarbon ring of an aryl group may be attached or fused to one or more saturated, partially unsaturated or aromatic rings—e.g., dihydronaphthyl, indenyl, indanyl and tetrahydronaphthyl (tetralinyl). The term "-aryl-" refers to a divalent aryl group. An aryl group and an -aryl- group may optionally be substituted with one or more substituents as described herein.

The term "heteroaryl" refers to a monocyclic aromatic group or a multicyclic group that contains at least one aromatic ring, wherein at least one aromatic ring contains one or more heteroatoms independently selected from O, N and S. The heteroaromatic ring may be attached or fused to one or more saturated, partially unsaturated or aromatic rings that may contain only carbon atoms or that may contain one or more heteroatoms. A heteroaryl group may be attached to the main structure at any heteroatom or carbon atom which results in the creation of a stable compound. In certain embodiments, a heteroaryl group has from 5 to 15, or 5 to 12, or 5 to 10 ring atoms. Examples of monocyclic heteroaryl groups include without limitation pyrrolyl, pyrazolyl, pyrazolinyl, imidazolyl, oxazolyl, isoxazolyl, thiazolyl, thiadiazolyl, isothiazolyl, furanyl, thienyl (thiophenyl), oxadiazolyl, triazolyl, tetrazolyl, pyridyl, pyrazinyl, pyrimidinyl, pyridazinyl and triazinyl. Non-limiting examples of bicyclic heteroaryl groups include indolyl, benzothiazolyl, benzothiadiazolyl, benzoxazolyl, benzisoxazolyl, benzothienyl (benzothiophenyl), quinolinyl, tetrahydroisoquinolinyl, isoquinolinyl, benzimidazolyl, benzotriazolyl, indolizinyl, benzofuranyl, isobenzofuranyl, chromonyl, coumarinyl, cinnolinyl, quinazolinyl, quinoxalinyl, indazolyl, naphthyridinyl, phthalazinyl, quinazolinyl, purinyl, pyrrolopyridinyl, furopyridinyl, thienopyridinyl, dihydroisoindolyl and tetrahydroquinolinyl. Examples of tricyclic heteroaryl groups include without limitation carbazolyl, benzindolyl, dibenzofuranyl, phenanthrollinyl, acridinyl, phenanthridinyl and xanthenyl. The term "-heteroaryl-" refers to a divalent heteroaryl group. A heteroaryl group and a -heteroaryl- group may optionally be substituted with one or more substituents as described herein.

Each group described herein (including without limitation alkyl, heteroalkyl, alkylaryl, cycloalkyl, heterocyclyl, aryl and heteroaryl), whether as a primary group or as a substituent group, may optionally be substituted with one or more substituents. In certain embodiments, each group described herein may optionally be substituted with one to six substituents independently selected from the group consisting of halide, cyano, nitro, hydroxyl, sulfhydryl (—SH), amino (—NH$_2$), —OR$^{11}$, —SR$^{11}$, —NR$^{12}$R$^{13}$, —C(=O)R$^{11}$, —C(=O)OR$^{11}$, —OC(=O)R$^{11}$, —C(=O)NR$^{12}$R$^{13}$, —NR$^{11}$C(=O)R$^{11}$, alkyl, cycloalkyl, heterocyclyl, aryl and heteroaryl, wherein:

R$^{11}$ in each occurrence independently is hydrogen, alkyl, cycloalkyl, heterocyclyl, aryl or heteroaryl; and R$^{12}$ and R$^{13}$ in each occurrence independently are hydrogen, alkyl, cycloalkyl, heterocyclyl, aryl or heteroaryl, or R$^{12}$ and R$^{13}$ and the nitrogen atom to which they are connected form a heterocyclic or heteroaryl ring.

II. STEREOISOMERS

It is understood that the present disclosure encompasses all possible stereoisomers, including all possible diastereomers and enantiomers and racemic mixtures of enantiomers, of the compounds described herein, and not only the specific stereoisomers as indicated by drawn structure or nomenclature. Some embodiments of the disclosure relate to the specific stereoisomers indicated by drawn structure or nomenclature. The specific recitation of the phrase "or stereoisomers thereof" or the like with respect to a compound in certain instances of the disclosure shall not be interpreted as an intended omission of any of the other possible stereoisomers of the compound in other instances of the disclosure where the term "compound" is used without recitation of the phrase "or stereoisomers thereof" or the like.

III. TREPROSTINIL DERIVATIVES

The present disclosure provides treprostinil derivatives that can function as prodrugs of treprostinil. In some embodiments, a treprostinil derivative is of Formula (I):

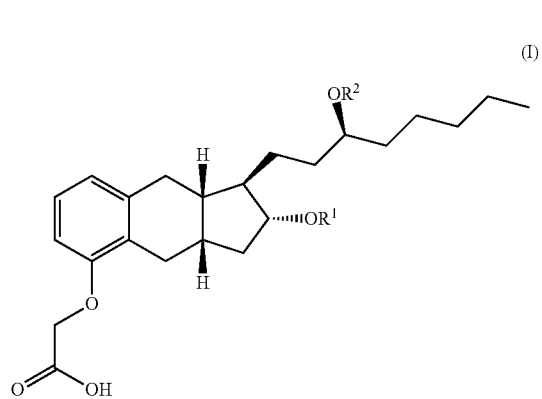

wherein:

R$^1$ and R$^2$ independently are hydrogen,

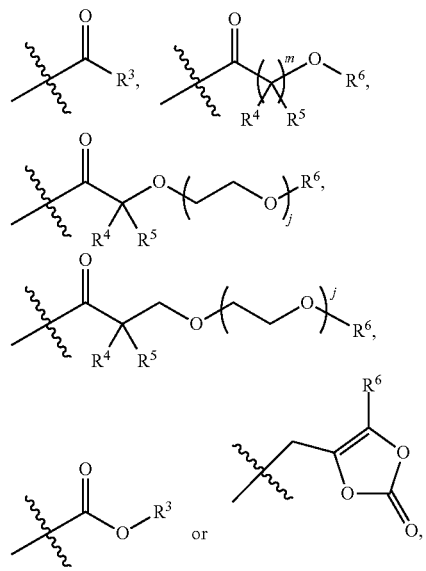

wherein:

R$^3$ in each occurrence independently is alkyl, -alkylaryl, cycloalkyl, heterocyclyl, aryl or heteroaryl, each of which may optionally be substituted;

R$^4$ and R$^5$ in each occurrence independently are hydrogen, C$_1$-C$_6$ alkyl or C$_3$-C$_6$ cycloalkyl, or R$^4$ and R$^5$ and the carbon atom to which they are connected form a C$_3$-C$_6$ cycloalkyl ring;

R$^6$ in each occurrence independently is hydrogen, R$^3$, —C(=O)R$^3$, —C(=O)OR$^3$ or —C(=O)NR$^9$R$^{10}$; or R$^6$ and R$^4$ or R$^5$, together with the atoms to which they are connected, form a heterocyclic ring;

R$^9$ and R$^{10}$ in each occurrence independently are hydrogen, alkyl, -alkylaryl, cycloalkyl, heterocyclyl, aryl or heteroaryl; or R$^9$ and R$^{10}$ and the nitrogen atom to which they are connected form a heterocyclic or heteroaryl ring;

j in each occurrence independently is an integer from 0 to 4; and m in each occurrence independently is an integer from 1 to 10;

or a pharmaceutically acceptable salt, solvate, hydrate, clathrate, polymorph or stereoisomer thereof, with the proviso that:

both R¹ and R² are not hydrogen;
neither —OR¹ nor —OR² forms an acetate;
neither —OR¹ nor —OR² forms a substituted cyclohexane-ester; and
neither —OR¹ nor —OR² forms an ester with or of an amino acid (protected or unprotected), a peptide or a protein.

In certain embodiments, R³ in

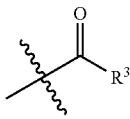

is not alkyl substituted with a nitrogen-containing group, or not cycloalkyl substituted with a carbonyl-containing group. In further embodiments, neither the alkyl nor the cycloalkyl group of R³ in

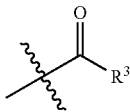

is substituted. In yet further embodiments, none of the alkyl, -alkylaryl, cycloalkyl, heterocyclyl, aryl or heteroaryl group of R³ in

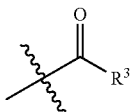

is substituted.

In some embodiments, j in each occurrence independently is 0, 1 or 2. In certain embodiments, j is 0. In further embodiments, m in each occurrence independently is an integer from 1 to 6.

In some embodiments, R¹ and R² independently are

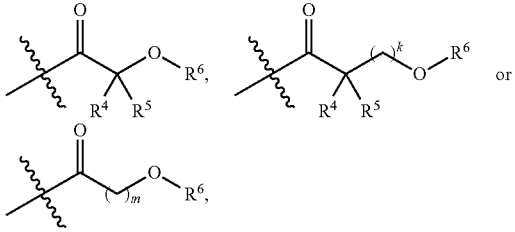

wherein R⁴, R⁵, R⁶ and m are as defined above, and k in each occurrence independently is an integer from 1 to 9. In certain embodiments, k in each occurrence independently is an integer from 1 to 5.

In further embodiments, R³ in each occurrence independently is $C_1$-$C_6$ alkyl; R⁴ and R⁵ in each occurrence independently are hydrogen or $C_1$-$C_3$ alkyl, or R⁴ and R⁵ and the carbon atom to which they are connected form a cyclopropyl ring; R⁶ in each occurrence independently is hydrogen or R³; j in each occurrence independently is 0 or 1; and m in each occurrence independently is 1 or 2. In certain embodiments, R³ in each occurrence independently is methyl, ethyl, propyl, isopropyl, butyl, iso-butyl, sec-butyl or tert-butyl; R⁴ and R⁵ in each occurrence independently are hydrogen, methyl, ethyl, propyl or isopropyl; R⁶ in each occurrence independently is hydrogen or R³; j is 0; and m ist.

In some embodiments, R¹ and R² independently are selected from the group consisting of:

hydrogen,

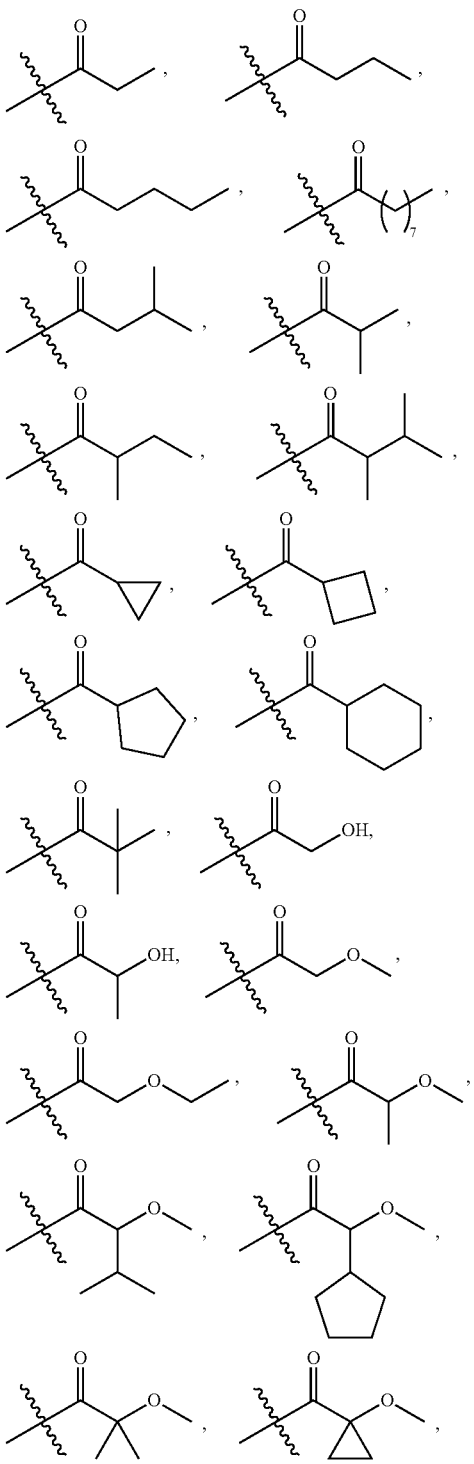

-continued

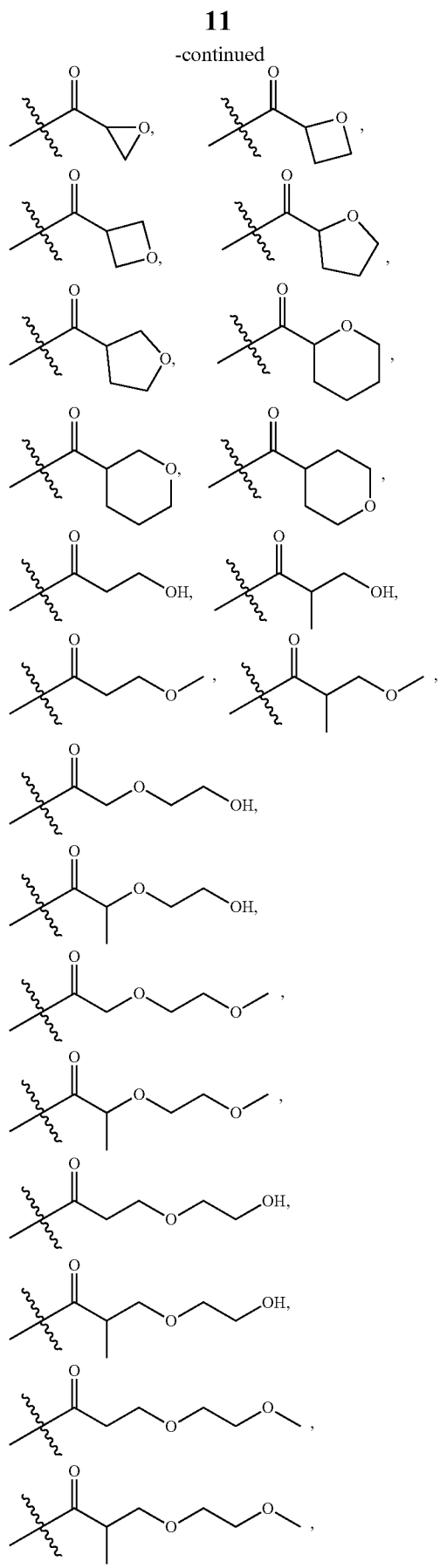

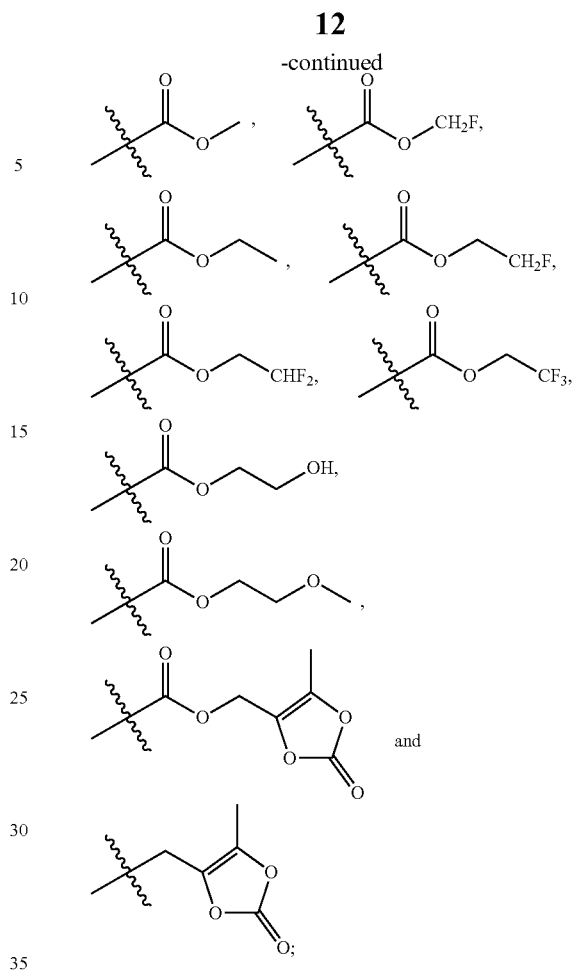

wherein each moiety that has a stereocenter adjacent to the carbonyl group can have the (R)-stereochemistry or the (S)-stereochemistry or can be racemic at that stereocenter; with the proviso that both $R^1$ and $R^2$ are not hydrogen. The disclosure specifically describes treprostinil derivatives in which: (1) $R^2$ is hydrogen and —$OR^1$ is derivatized with each of the moieties (other than hydrogen) in the preceding group; (2) $R^1$ is hydrogen and —$OR^2$ is derivatized with each of the moieties (other than hydrogen) in the preceding group; and (3) both —$OR^1$ and —$OR^2$ are derivatized with the same moiety and with each of the moieties (other than hydrogen) in the preceding group. In certain embodiments, $R^1$ and $R^2$ independently are selected from the group consisting of:

hydrogen,

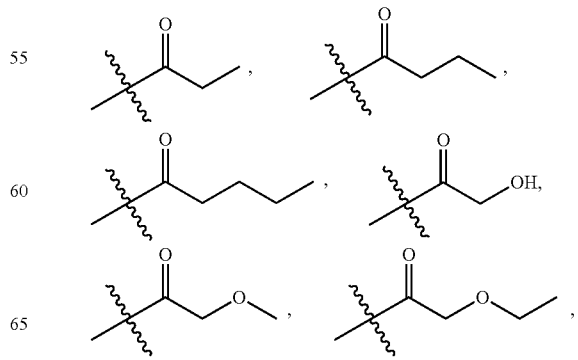

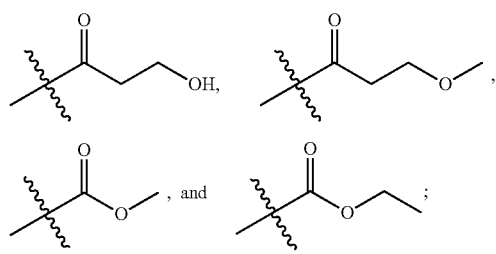

with the proviso that both $R^1$ and $R^2$ are not hydrogen.

In some embodiments, both —$OR^1$ and —$OR^2$ are derivatized [Formula (Ic)], optionally with the same group. In other embodiments, $R^2$ is hydrogen and —$OR^1$ is derivatized [Formula (Ia)]. In yet other embodiments, $R^1$ is hydrogen and —$OR^2$ is derivatized [Formula (Ib)].

In certain embodiments, a treprostinil derivative of Formula (I) is selected from the group consisting of:

Compound Ia-1
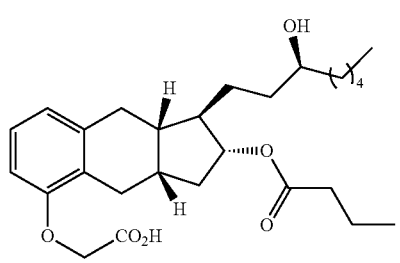

Compound Ia-2
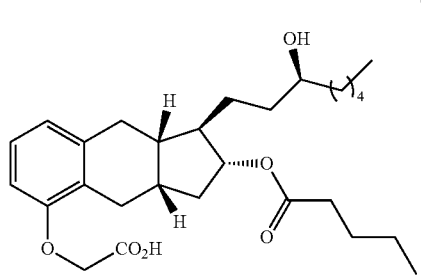

Compound Ia-3
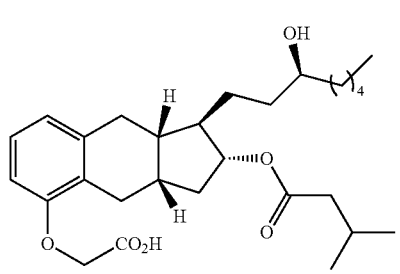

Compound Ia-4
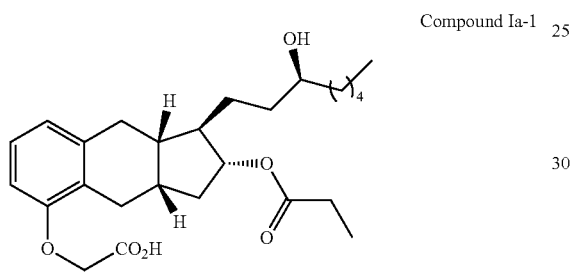

Compound Ia-5
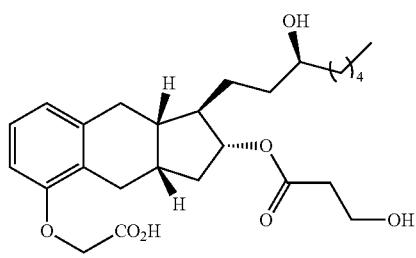

Compound Ia-6
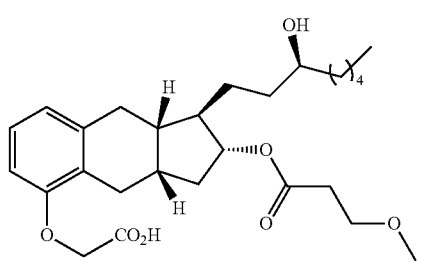

Compound Ia-7
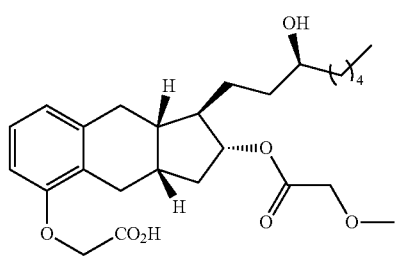

Compound Ia-8
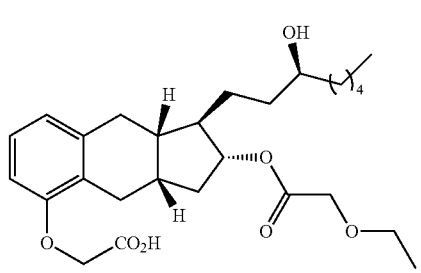

Compound Ia-9
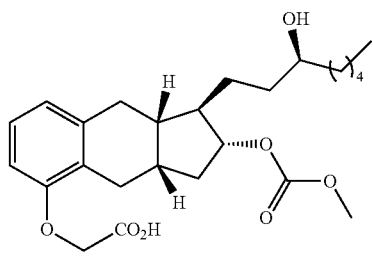

Compound Ia-10

Compound Ia-11
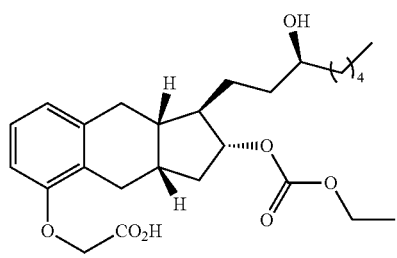
Compound Ib-1
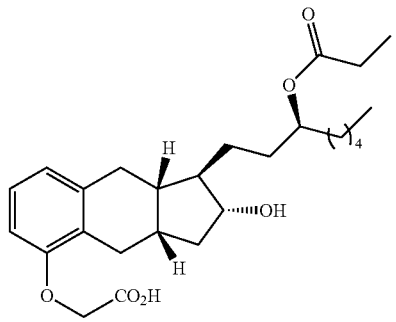
Compound Ia-12
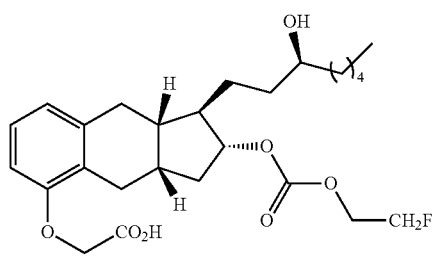
Compound Ib-2
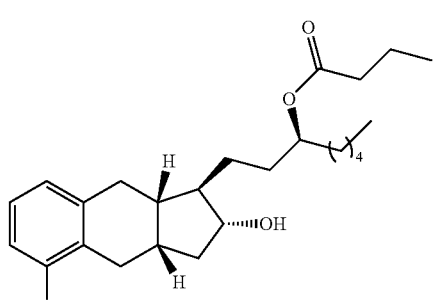
Compound Ia-13
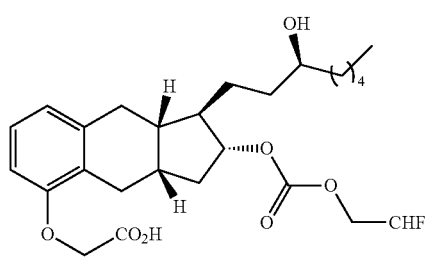
Compound Ia-14
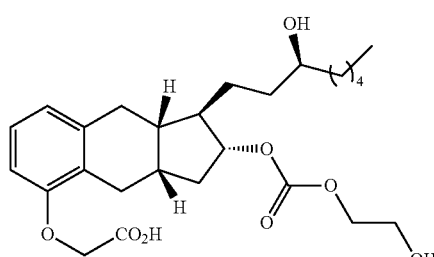
Compound Ib-3
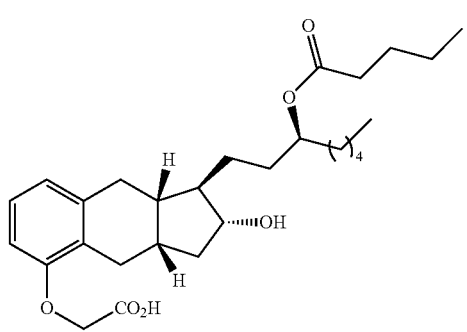
Compound Ia-15
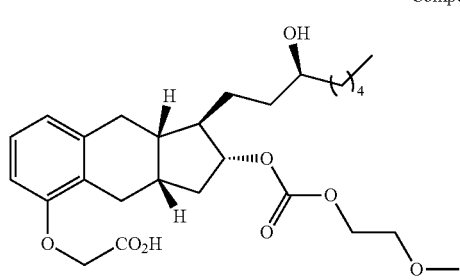
Compound Ib-4
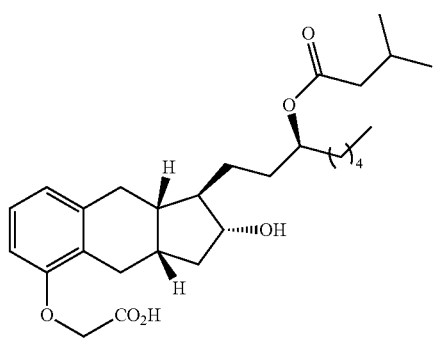

-continued
Compound Ib-5
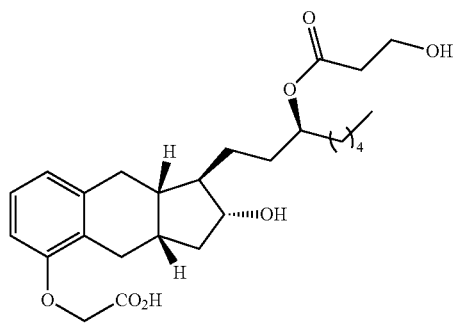
Compound Ib-6
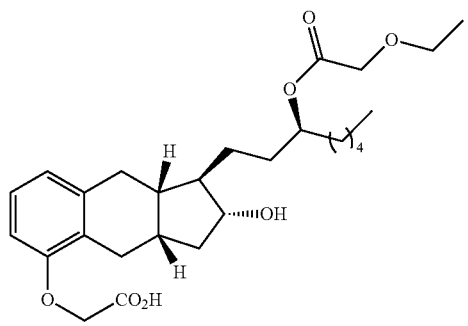
Compound Ib-7
Compound Ib-8
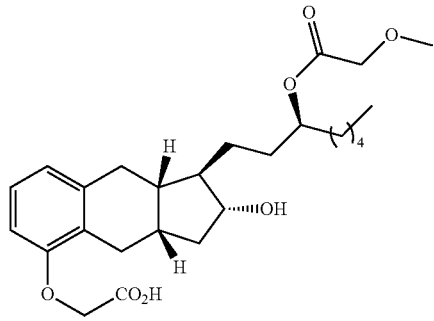
-continued
Compound Ib-9
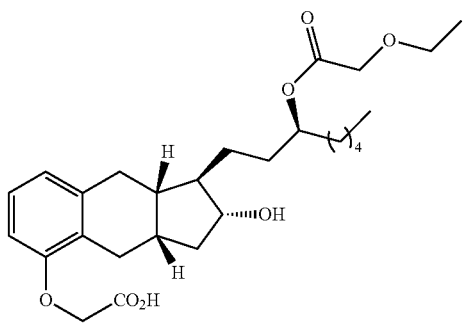
Compound Ib-10
Compound Ib-11
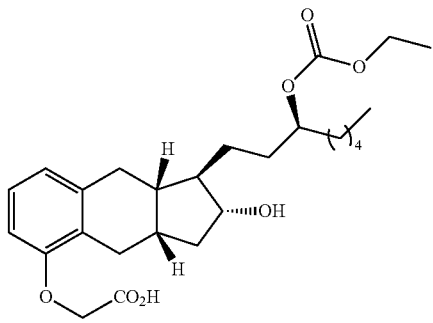
Compound Ib-12

-continued

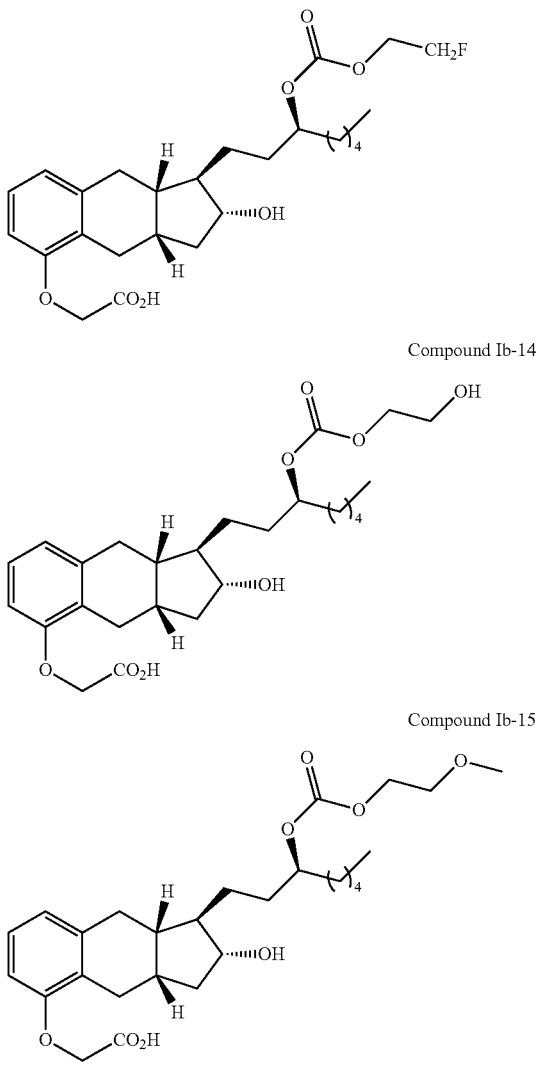

Compound Ib-13

Compound Ib-14

Compound Ib-15 and pharmaceutically acceptable salts, solvates, hydrates, clathrates, polymorphs and stereoisomers thereof.

In other embodiments, a treprostinil derivative is of Formula (II):

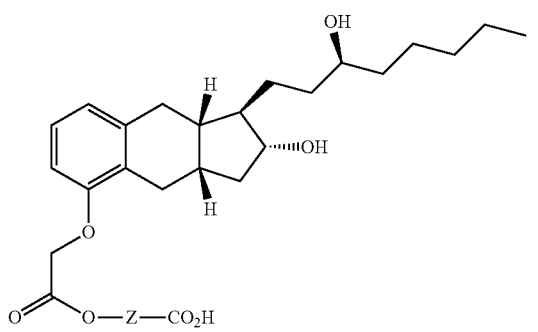

(II)

wherein:
—O—Z—CO$_2$H is

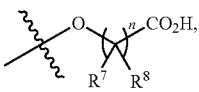

—O-heteroalkyl-CO$_2$H, —O-cyclyl-CO$_2$H, —O—CH$_2$-cyclyl-CO$_2$H, —O-cyclyl-CH$_2$—CO$_2$H, or —O—CH$_2$-cyclyl-CH$_2$—CO$_2$H, each of which may optionally be substituted, wherein:
  cyclyl- is -cycloalkyl-, -heterocyclyl-, -aryl- or -heteroaryl-;
  $R^7$ and $R^8$ in each occurrence independently are hydrogen, $C_1$-$C_6$ alkyl or $C_3$-$C_6$ cycloalkyl, or $R^7$ and $R^8$ and the carbon atom to which they are connected form a $C_3$-$C_6$ cycloalkyl ring; and
  n is an integer from 1 to 10;
or a pharmaceutically acceptable salt, solvate, hydrate, clathrate, polymorph or stereoisomer thereof, with the proviso that:
  —O—Z—CO$_2$H is not

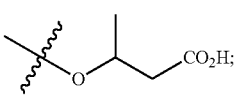 [SMILES: *OC(C)CC(=O)O]

and
  —O—Z—CO$_2$H does not contain a sugar moiety.
In some embodiments, n is an integer from 1 to 6.
In certain embodiments, —O—Z—CO$_2$H does not contain a -heterocyclyl- group, or a substituted -heterocyclyl- group.
In some embodiments, —O—Z—CO$_2$H is

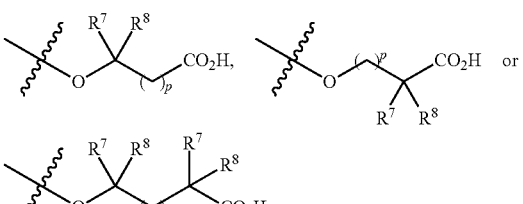

wherein $R^7$ and $R^8$ are as defined above, p is an integer from 1 to 9, and q is an integer from 0 to 8, with the proviso that —O—Z—CO$_2$H is not

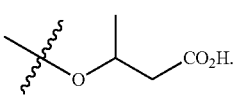 [SMILES: *OC(C)CC(=O)O]

In certain embodiments, p is an integer from 1 to 5, and q is an integer from 0 to 4. In some embodiments, both $R^7$ and $R^8$ are hydrogen, and p is an integer from 1 to 5 or from 1 to 3 (or each occurrence of $R^7$ and $R^8$ is hydrogen, and q is an integer from 0 to 4 or from 0 to 2). The disclosure specifically describes treprostinil derivatives in which both $R^7$ and $R^8$ are hydrogen, and p is each of 1, 2, 3, 4, 5, 6, 7, 8 and 9. In further embodiments, —O—Z—CO$_2$H is

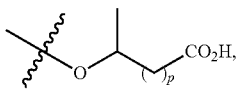

and p is 2, 3, 4 or 5. The disclosure specifically describes treprostinil derivatives in which —O—Z—CO₂H is

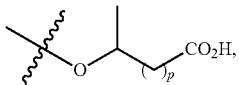

and p is each of 2, 3, 4, 5, 6, 7, 8 and 9, wherein the stereocenter connected to the methyl group can have the (R)-stereochemistry or the (S)-stereochemistry or can be racemic at that position.

In other embodiments, —O—Z—CO₂H is —O-heteroalkyl-CO₂H, and —O-heteroalkyl-CO₂H is selected from the group consisting of:

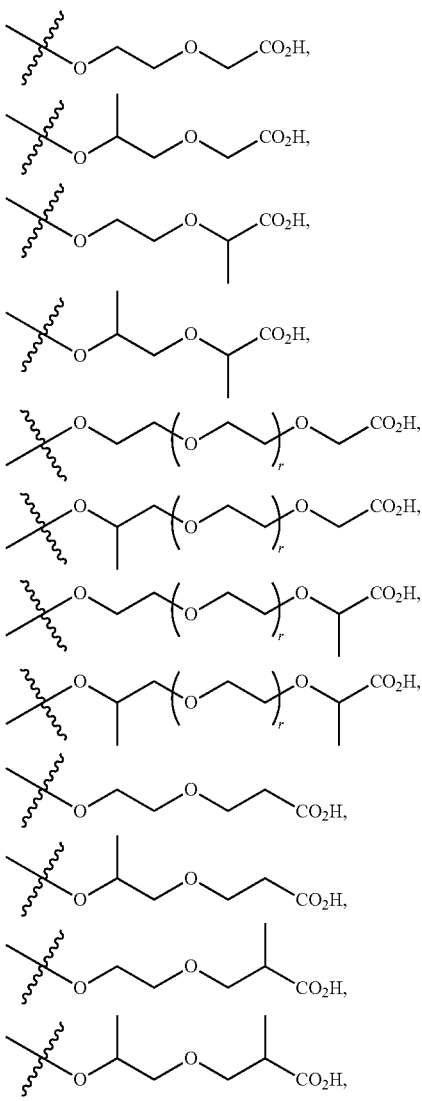

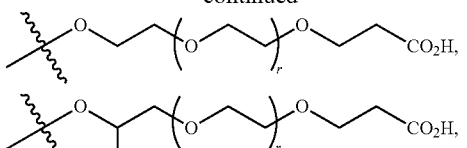

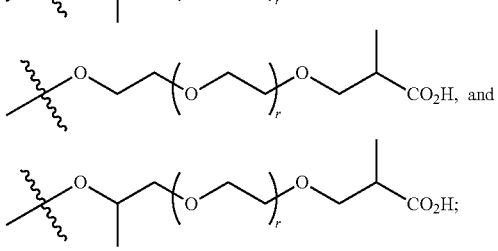

wherein r is each of 1, 2 and 3; and wherein each moiety that has a stereocenter adjacent to the oxygen atom connected to treprostinil, and/or a stereocenter adjacent to the carboxyl group, independently can have the (R)-stereochemistry or the (S)-stereochemistry or can be racemic at that (those) stereocenter(s). The disclosure specifically describes treprostinil derivatives in which —O—Z—CO₂H is each of the moieties in the preceding group. In certain embodiments, —O—Z—CO₂H is

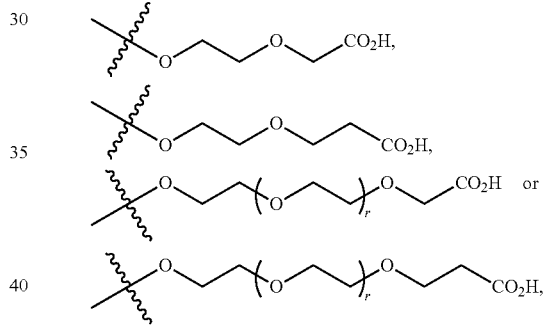

wherein r is 1, 2 or 3.

In further embodiments, —O—Z—CO₂H is —O-cycloalkyl-CO₂H, —O—CH₂-cycloalkyl-CO₂H, —O-cycloalkyl-CH₂—CO₂H, or —O—CH₂-cycloalkyl-CH₂—CO₂H, and for each of the preceding moieties -cycloalkyl- is:

1,2-cyclopropyl (cis or trans); or 1,3-cyclobutyl (cis or trans) or 1,2-cyclobutyl (cis or trans); or 1,3-cyclopentyl (cis or trans) or 1,2-cyclopentyl (cis or trans); or 1,4-cyclohexyl (cis or trans), 1,3-cyclohexyl (cis or trans), or 1,2-cyclohexyl (cis or trans). The disclosure specifically describes the 64 treprostinil derivatives in which —O—Z—CO₂H is each of the moieties in the preceding group. In certain embodiments, —O—Z—CO₂H is selected from the group consisting of:

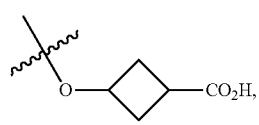

-continued
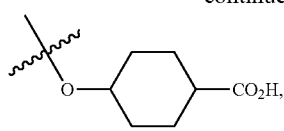
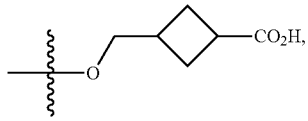
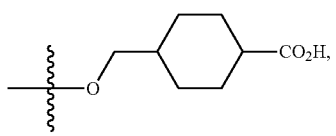
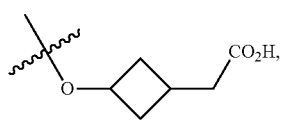
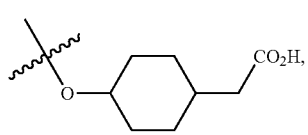
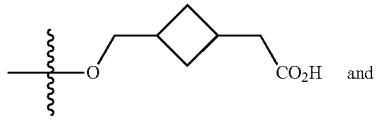 and
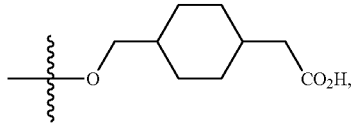
wherein for each of the moieties the two groups on the cycloalkyl ring can be cis or trans relative to one another.
In some embodiments, a treprostinil derivative of Formula (II) is selected from the group consisting of:
Compound II-1
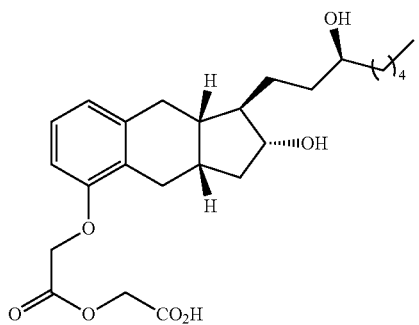
-continued
Compound II-2
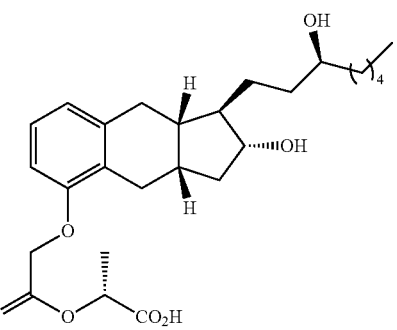
Compound II-3
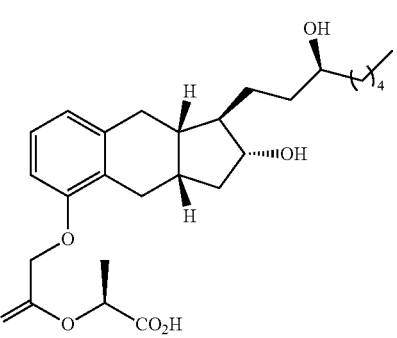
Compound II-4
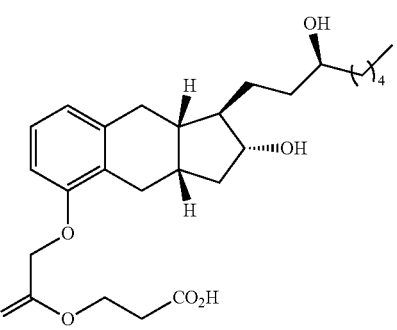
Compound II-5
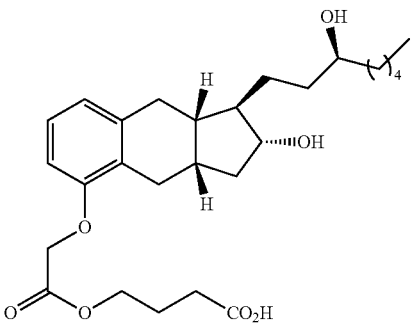

-continued
Compound II-6
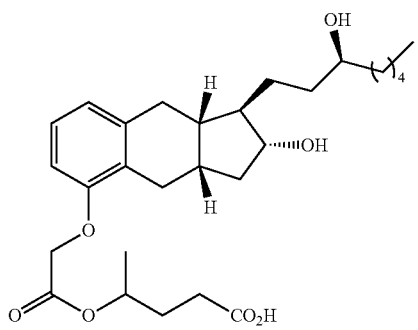
Compound II-10
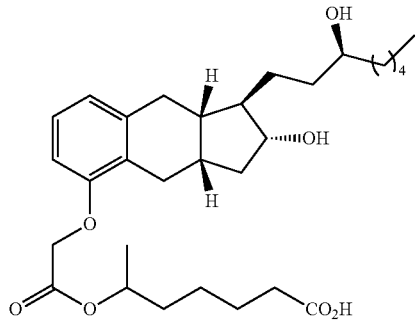
Compound II-7
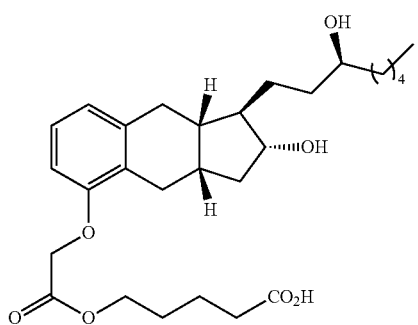
Compound II-11
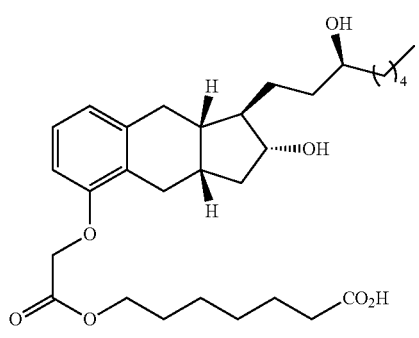
Compound II-8
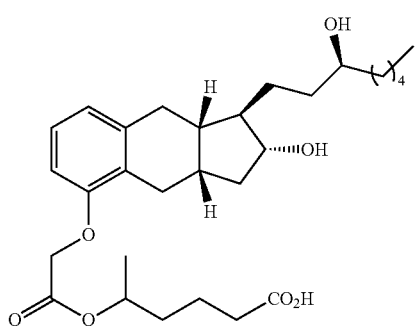
Compound II-12
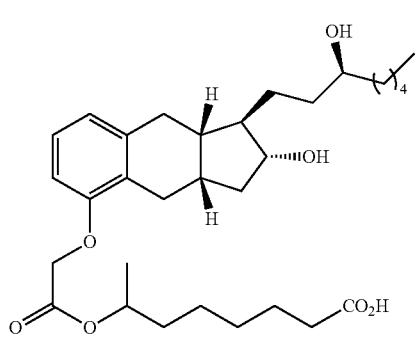
Compound II-9
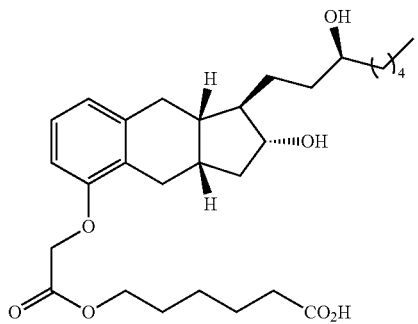
Compound II-13
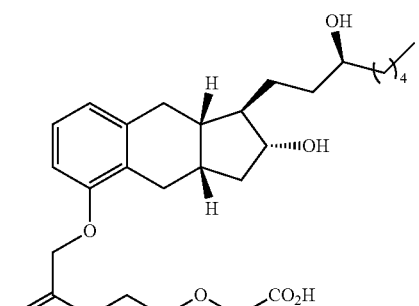

Compound II-14
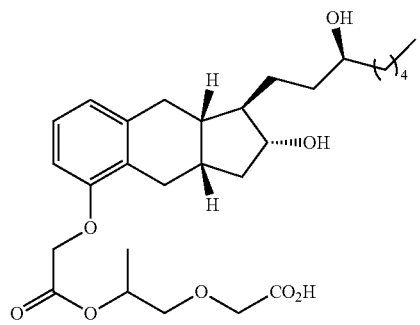
Compound II-18
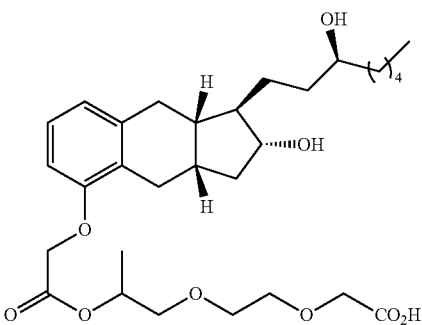
Compound II-15
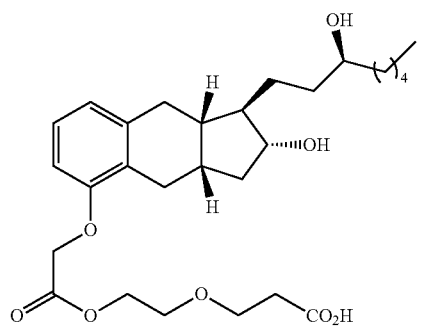
Compound II-19
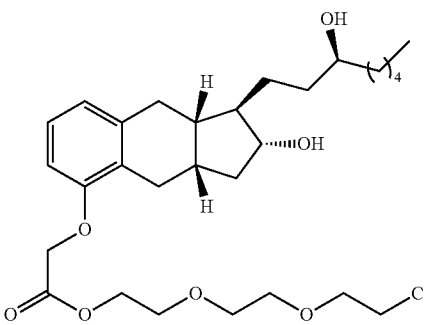
Compound II-16
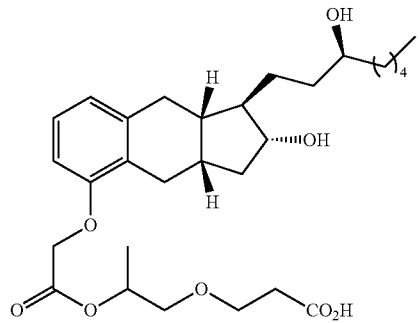
Compound II-20
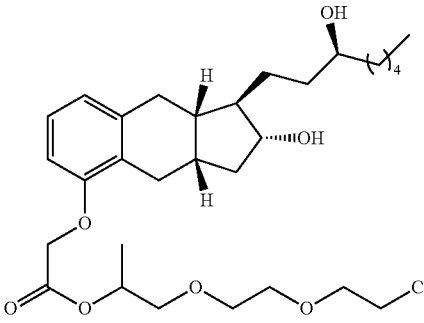
Compound II-17
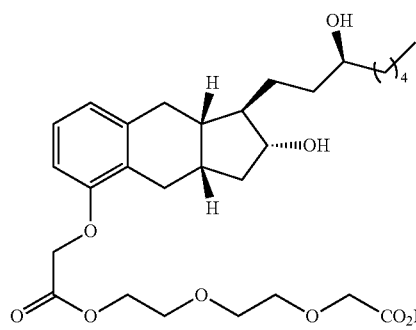
Compound II-21
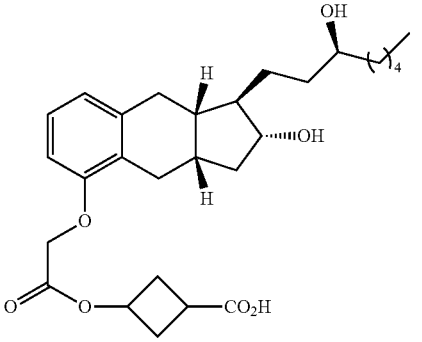

Compound II-22

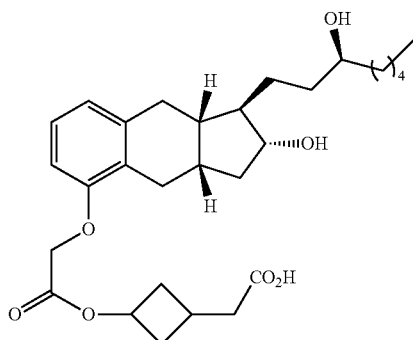

Compound II-23

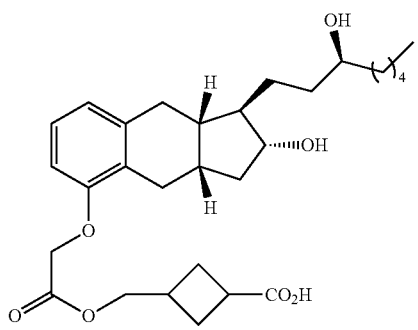

Compound II-24

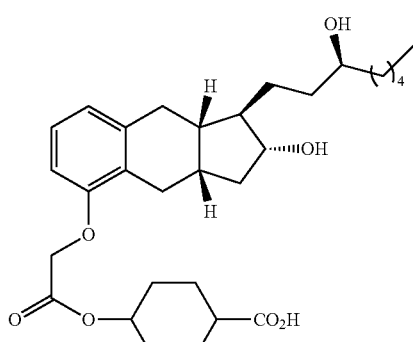

Compound II-25

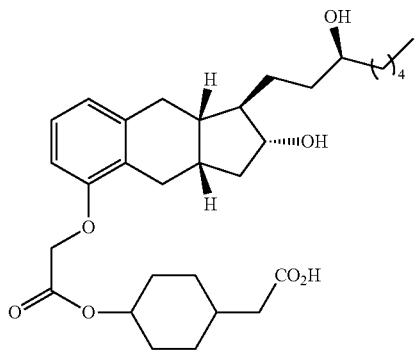

Compound II-26

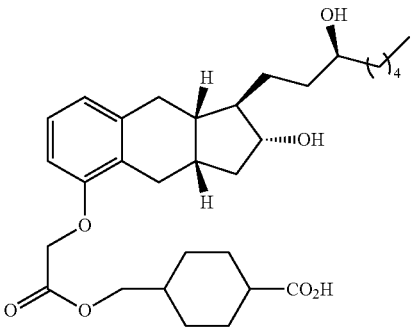

and pharmaceutically acceptable salts, solvates, hydrates, clathrates, polymorphs and stereoisomers thereof.

The treprostinil derivatives described herein can exist or be used in the form of a pharmaceutically acceptable salt. The treprostinil derivatives have a carboxyl group, and thus can form an addition salt with a base. Pharmaceutically acceptable base addition salts can be formed with, e.g., metals (e.g., alkali metals or alkaline earth metals) or amines (e.g., organic amines). Examples of metals useful as cations include without limitation alkali metals (e.g., lithium, sodium, potassium and cesium), alkaline earth metals (e.g., magnesium and calcium), aluminum and zinc. Metal cations can be provided by way of, e.g., inorganic bases, such as hydroxides, carbonates and hydrogen carbonates. Non-limiting examples of organic amines useful for forming base addition salts include chloroprocaine, choline, cyclohexylamine, dibenzylamine, N,N'-dibenzylethylene-diamine, dicyclohexylamine, diethanolamine, ethylenediamine, N-ethylpiperidine, histidine, isopropylamine, N-methylglucamine, procaine, pyrazine, triethylamine, trimethylamine and tromethamine.

If a compound has a basic atom or functional group (e.g., a basic nitrogen atom), the compound can form an addition salt with an acid. Non-limiting examples of acids useful for forming acid addition salts include mineral acids (e.g., HCl, HBr, HI, nitric acid, phosphoric acid and sulfuric acid) and organic acids, such as carboxylic acids (e.g., acetic acid) and sulfonic acids (e.g., ethanesulfonic acid). Pharmaceutically acceptable salts are discussed in detail in Handbook of Pharmaceutical Salts, Properties, Selection and Use, P. Stahl and C. Wermuth, Eds., Wiley-VCH (2011).

IV. DEUTERATED TREPROSTINIL COMPOUNDS

To eliminate foreign substances such as drugs, the animal body expresses a variety of enzymes, such as cytochrome $P_{450}$ enzymes, esterases, proteases, reductases, dehydrogenases and monoamine oxidases, which react with and convert the foreign substances to more polar intermediates or metabolites for renal excretion. Such metabolic reactions can involve the oxidation of a carbon-hydrogen (C—H) bond to a carbon-oxygen (C—O) bond or a carbon-carbon (C═C) pi bond. The resulting metabolites may be stable or unstable under physiological conditions, and may have substantially different pharmacologic, pharmacokinetic and pharmacodynamic properties and toxicity profiles compared to the parent compounds. For many drugs, such metabolic oxidations can be rapid and lead to the requirement of higher dosage amounts and/or increased dosing frequencies, which can result in greater side effects.

The present disclosure provides treprostinil isotopologues corresponding to the treprostinil derivatives described herein which are enriched with deuterium (deuterated) at one or more positions. In some embodiments, a treprostinil derivative is deuterated at one or more positions in the parent treprostinil structure so that when the derivative is converted to treprostinil in vivo, the resulting active parent drug is deuterated at one or more positions.

Deuteration of a treprostinil compound at one or more positions can have any one or more, or all, of the following benefits: (1) a longer half-life; (2) decreased amount of a dose and/or decreased number of doses needed to achieve a desired effect; (3) decreased variation between subjects in the blood or plasma level of the parent drug; (4) increased efficacy; (5) reduced side effects due to decreased amount of the parent drug administered and/or decreased production of deleterious metabolites; and (6) increased maximum tolerated dose.

Deuterium can be substituted for hydrogen at any one or more, or all, of the available positions in a treprostinil (Trp) compound, including at any one or more, or all, of the available positions in the phenyl ring of Trp, the cyclohexyl ring of Trp, the cyclopentyl ring of Trp, the octyl chain of Trp, or the hydroxyacetic acid group of Trp, or any combination thereof. In certain embodiments, a treprostinil derivative is deuterated at one or more, or all, of the available positions in the cyclohexyl ring of Trp and/or the hydroxyacetic acid group of Trp. In some embodiments, at least one of the available positions has deuterium enrichment of at least about 10%, 25%, 50%, 75%, 90%, 95% or 98%. In certain embodiments, at least one of the available positions has deuterium enrichment of at least about 90%, 95% or 98%.

In further embodiments, each position in a treprostinil derivative enriched with deuterium (or deuterated) independently has deuterium enrichment of at least about 10%, 25%, 50%, 75%, 90%, 95% or 98%. In certain embodiments, each position enriched with deuterium independently has deuterium enrichment of at least about 90%, 95% or 98%.

Deuterated treprostinil derivatives can also contain less prevalent isotopes for other elements, including without limitation $^{13}C$ or $^{14}C$ for carbon and $^{17}O$ or $^{18}O$ for oxygen.

The term "deuterium enrichment" refers to the percentage of incorporation of deuterium at a given position in a molecule in place of hydrogen. For example, deuterium enrichment of 10% at a given position means that 10% of molecules in a given sample contain deuterium at that position. Because the naturally occurring distribution of deuterium is about 0.0156%, deuterium enrichment at any position in a molecule synthesized using non-deuterium-enriched starting materials or reagents is about 0.0156%. Deuterium enrichment can be determined using conventional analytical methods known to one of ordinary skill in the art, including mass spectrometry and nuclear magnetic resonance spectroscopy.

The term "is deuterium" or "is deuterated", when used to describe a given position in a molecule, or the symbol "D", when used to represent an element at a given position in a drawing of a molecular structure, means that the specified position is enriched with deuterium above the naturally occurring distribution of deuterium. In some embodiments, deuterium enrichment is at least about 10%, 20%, 30%, 40%, 50%, 60%, 70%, 80%, 90%, 95%, 98% or 99% (e.g., at least about 50%) of deuterium at the specified position. In certain embodiments, deuterium enrichment is at least about 90%, 95% or 98% of deuterium at the specified position.

V. PHARMACEUTICAL COMPOSITIONS

Additional embodiments of the disclosure relate to pharmaceutical compositions comprising one or more treprostinil derivatives described herein, or a pharmaceutically acceptable salt, solvate, hydrate, clathrate or polymorph thereof, and one or more pharmaceutically acceptable excipients or carriers. The compositions can optionally contain an additional therapeutic agent.

Pharmaceutically acceptable excipients and carriers include pharmaceutically acceptable substances, materials and vehicles. Non-limiting examples of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, sweetening agents, flavoring agents, coloring agents, stabilizers, preservatives, antioxidants, antimicrobial agents, antibacterial agents, antifungal agents, adjuvants, encapsulating materials and coating materials. The use of such excipients in pharmaceutical formulations is known in the art. For example, conventional vehicles and carriers include without limitation oils (e.g., vegetable oils, such as sesame oil), aqueous solvents (e.g., saline and phosphate-buffered saline [PBS]), and solvents (e.g., dimethyl sulfoxide [DMSO] and alcohols [such as ethanol and glycerol]). Except insofar as any conventional excipient or carrier is incompatible with the active ingredient (for purposes of the content of a pharmaceutical composition, the term "active ingredient" encompasses a prodrug), the disclosure encompasses the use of conventional excipients and carriers in formulations containing treprostinil derivatives. See, e.g., Remington: The Science and Practice of Pharmacy, 21st Ed., Lippincott Williams & Wilkins (Philadelphia, Pa. [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla. [2004]).

Proper formulation can depend on various factors, such as the route of administration chosen. Potential routes of administration of pharmaceutical compositions comprising treprostinil derivatives include without limitation oral, parenteral (including intradermal, subcutaneous, intramuscular, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). Topical formulations can be designed to produce a local or systemic therapeutic effect.

As an example, formulations of treprostinil derivatives suitable for oral administration can be presented as, e.g., capsules (including push-fit capsules and soft capsules), cachets or tablets; as powders or granules; or as boluses, electuaries or pastes. For example, push-fit capsules can contain a treprostinil derivative in admixture with, e.g., a filler (e.g., lactose), a binder (e.g., a starch) and a lubricant (e.g., talc or magnesium stearate), and optionally a stabilizer. For soft capsules, a treprostinil derivative can be dissolved or suspended in a suitable liquid (e.g., a fatty oil, liquid paraffin or liquid polyethylene glycol), and a stabilizer can be added.

Compositions for oral administration can also be formulated as solutions or suspensions in an aqueous liquid and/or a non-aqueous liquid, or as oil-in-water liquid emulsions or water-in-oil liquid emulsions. Dispersible powder or granules of a treprostinil derivative can be mixed with any suitable combination of an aqueous liquid, an organic solvent and/or an oil and any suitable excipients (e.g., any combination of a dispersing agent, a wetting agent, a suspending agent, an emulsifying agent and/or a preservative) to form a solution, suspension or emulsion.

Treprostinil derivatives can also be formulated for parenteral administration by injection or infusion to circumvent gastrointestinal absorption and first-pass metabolism. An exemplary parenteral route is intravenous. Additional advantages of intravenous administration include direct administration of a therapeutic agent into systemic circulation to achieve a rapid systemic effect, and the ability to administer the agent continuously and/or in a large volume if desired. Formulations for injection or infusion can be in the form of, e.g., solutions, suspensions or emulsions in oily or aqueous vehicles, and can contain excipients such as suspending agents, dispersing agents and/or stabilizing agents. For example, aqueous or non-aqueous (e.g., oily) sterile injection solutions can contain a treprostinil derivative along with excipients such as an antioxidant, a buffer, a bacteriostat and solutes that render the formulation isotonic with the blood of the subject. Aqueous or non-aqueous sterile suspensions can contain a treprostinil derivative along with excipients such as a suspending agent and a thickening agent, and optionally a stabilizer and an agent that increases the solubility of the treprostinil derivative to allow for the preparation of a more concentrated solution or suspension. As another example, a sterile aqueous solution for injection or infusion (e.g., subcutaneously or intravenously) can contain a treprostinil derivative, sodium chloride, a buffering agent (e.g., sodium citrate), a preservative (e.g., meta-cresol), and optionally a base (e.g., NaOH) and/or an acid (e.g., HCl) to adjust pH.

In some embodiments, a topical dosage form of a treprostinil derivative is formulated as a buccal or sublingual tablet or pill. Advantages of a buccal or sublingual tablet or pill include avoidance of gastrointestinal absorption and first-pass metabolism, and rapid absorption into systemic circulation. A buccal or sublingual tablet or pill can be designed to provide faster release of the treprostinil derivative for more rapid uptake of it into systemic circulation. In addition to a therapeutically effective amount of a treprostinil derivative, the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

In addition, treprostinil derivatives can be formulated for intranasal administration. Intranasal administration bypasses gastrointestinal absorption and first-pass metabolism. An intranasal formulation can comprise a treprostinil derivative along with excipients, such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) and/or a penetration enhancer.

Furthermore, treprostinil derivatives can be formulated for administration by oral inhalation. Advantages of administration by inhalation include avoidance of first-pass metabolism, and the ability to tailor to rapid delivery of the therapeutic agent across the mucous membrane of the respiratory tract, or more selective deposition of the agent in the lungs with less systemic side effects. In certain embodiments, a sterile aqueous solution for oral inhalation contains a treprostinil derivative, sodium chloride, a buffering agent (e.g., sodium citrate), optionally a preservative (e.g., meta-cresol), and optionally a base (e.g., NaOH) and/or an acid (e.g., HCl) to adjust pH.

For a delayed or sustained release of a treprostinil derivative, a composition can be formulated as, e.g., a depot that can be implanted in or injected into a subject, e.g., intramuscularly or subcutaneously. A depot formulation can be designed to deliver the treprostinil derivative over an extended period of time, e.g., over at least about 1 week, 2 weeks, 3 weeks, 1 month, 1.5 months, 2 months or longer. For example, a treprostinil derivative can be formulated with a polymeric material (e.g., polyethylene glycol [PEG], polylactic acid [PLA] or polyglycolic acid [PGA], or a copolymer thereof [e.g., PLGA]), a hydrophobic material (e.g., as an emulsion in an oil) and/or an ion-exchange resin, or as a sparingly soluble derivative (e.g., a sparingly soluble salt).

A treprostinil derivative can also be contained or dispersed in a matrix material. The matrix material can comprise a polymer (e.g., ethylene-vinyl acetate) and controls the release of the compound by controlling dissolution and/or diffusion of the compound from, e.g., a reservoir, and can enhance the stability of the compound while contained in the reservoir. Such a "release system" can be configured as a transdermal or transmucosal patch and can contain an excipient that can accelerate the compound's release, such as a water-swellable material (e.g., a hydrogel) that aids in expelling the compound out of the reservoir. U.S. Pat. Nos. 4,144,317 and 5,797,898 describe examples of such a release system.

The release system can provide a temporally modulated release profile (e.g., pulsatile release) when time variation in plasma levels is desired, or a more continuous or consistent release profile when a constant plasma level is desired. Pulsatile release can be achieved from an individual reservoir or from a plurality of reservoirs. For example, where each reservoir provides a single pulse, multiple pulses ("pulsatile" release) are achieved by temporally staggering the single pulse release from each of multiple reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of a compound through it over an extended time period. In addition, continuous release can be approximated by releasing several pulses of a compound in rapid succession ("digital" release). An active release system can be used alone or in conjunction with a passive release system, as described in U.S. Pat. No. 5,797,898.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

The compositions can be presented in unit dosage form as a single dose wherein all active and inactive ingredients are combined in a suitable system, and components do not need to be mixed to form the composition to be administered. The unit dosage form can contain an effective dose, or an appropriate fraction thereof, of a treprostinil derivative. A representative example of a unit dosage form is a tablet, capsule, or pill for oral uptake.

Alternatively, the compositions can be presented as a kit, wherein the active ingredient, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected intravenously).

In some embodiments, a kit contains a treprostinil derivative or a pharmaceutically acceptable salt, solvate, hydrate, clathrate or polymorph thereof, and instructions for administering the compound to treat a condition responsive to treatment with treprostinil (e.g., pulmonary hypertension, such as pulmonary arterial hypertension). In certain embodiments, the compound is contained or incorporated in, or provided by, a device or system configured for transdermal delivery of the compound (e.g., a transdermal patch).

VI. TOPICAL COMPOSITIONS, INCLUDING TRANSDERMAL DELIVERY SYSTEMS

Topical formulations for application to the skin or mucosa can be useful for transdermal or transmucosal administration of a therapeutic agent into the blood for systemic distribution. Advantages of topical administration can include circumvention of gastrointestinal absorption and first-pass metabolism, delivery of a therapeutic agent with a short half-life and low oral bioavailability, more controlled and sustained release of the therapeutic agent, a more uniform plasma dosing or delivery profile of the therapeutic agent, less frequent dosing of the therapeutic agent, minimal or no invasiveness, ease of self-administration, and increased patient compliance. For purposes of the content of a pharmaceutical composition, the term "therapeutic agent" or "drug" encompasses a prodrug.

In general and in addition to the disclosure on topical formulations described elsewhere herein, compositions suitable for topical administration include without limitation liquid or semi-liquid preparations such as sprays, gels, liniments, lotions, oil-in-water or water-in-oil emulsions such as creams, foams, ointments and pastes, and solutions or suspensions such as drops (e.g., eye drops, nose drops and ear drops). In some embodiments, a topical composition comprises a therapeutic agent dissolved, dispersed or suspended in a carrier. The carrier can be in the form of, e.g., a solution, a suspension, an emulsion, an ointment or a gel base, and can contain, e.g., petrolatum, lanolin, a wax (e.g., bee wax), mineral oil, a long-chain alcohol, polyethylene glycol or polypropylene glycol, a diluent (e.g., water and/or an alcohol [e.g., ethanol or propylene glycol]), an emulsifier, a stabilizer or a thickening agent, or any combination thereof. A topical composition can include, or a topical formulation can be administered by means of, e.g., a transdermal or transmucosal delivery device, such as a transdermal patch, a microneedle patch or an iontophoresis device. A topical composition can deliver a drug transdermally or transmucosally via a concentration gradient (with or without the use of a chemical permeation enhancer) or an active mechanism (e.g., iontophoresis or microneedles).

In some embodiments, the treprostinil derivatives described herein are administered transdermally. In certain embodiments, the topical composition (e.g., transdermal delivery system) comprises a chemical permeation enhancer (e.g., a surfactant [e.g., sodium laureth sulfate], optionally in combination with an aromatic compound [e.g., phenylpiperazine]) that facilitates the transport of a treprostinil derivative across the skin into systemic circulation. In further embodiments, the treprostinil derivatives are administered via a transdermal patch. In certain embodiments, a transdermal patch comprises an impermeable backing membrane or layer, a drug reservoir, a semi-permeable membrane that can serve as a rate-limiting or rate-controlling diffusion barrier, and a skin-contacting adhesive layer. The semi-permeable membrane can be composed of, e.g., a suitable polymeric material (e.g., cellulose nitrate or acetate, polyisobutene, polypropylene, polyvinyl acetate or a polycarbonate). Transdermal drug-delivery systems, including patches, can be designed to provide controlled and prolonged release of a drug up to, e.g., about 1 week. WO 1993/003696 and U.S. Pat. Nos. 3,598,122; 4,144,317; 4,201,211; 4,262,003 and 4,379,454 describe various transdermal drug-delivery systems, including patches, which can deliver a controlled amount of a drug for an extended period of time ranging from several hours to several days. Such systems may be adapted for transdermal delivery of treprostinil derivatives.

VII. THERAPEUTIC USES OF TREPROSTINIL DERIVATIVES

The treprostinil derivatives described herein can be converted to treprostinil in vivo, and thus can act as prodrugs of treprostinil. In some embodiments, treprostinil derivatives are converted to treprostinil slowly and to an insubstantial extent (e.g., less than about 30%, 20%, 10% or 5% conversion) in the blood or the skin (if administered, e.g., transdermally), and are converted to treprostinil rapidly and substantially completely (e.g., at least about 70%, 80%, 90% or 95% conversion) in the liver. In other embodiments, treprostinil derivatives are converted to treprostinil to a substantial extent (e.g., at least about 30%, 40%, 50% or 60% conversion), or substantially completely (e.g., at least about 70%, 80%, 90% or 95% conversion), in the blood. In yet other embodiments, treprostinil derivatives are administered transdermally, are converted to treprostinil to some extent (e.g., less than about 30%, 20% or 10% conversion) in the skin, and do not cause a significant amount of side effects in the area of administration, such as irritation. In further embodiments, the treprostinil derivatives are at least about 50-fold, 100-fold, 500-fold or 1000-fold (e.g., at least about 100-fold) less effective in agonizing the prostacyclin receptor than treprostinil.

Treprostinil, a prostacyclin (prostaglandin I2) analog, has a variety of prostacyclin-like effects. For example, treprostinil can promote vasodilation, inhibit platelet activation and aggregation, inhibit thrombus formation, stimulate thrombolysis, inhibit atherogenesis, inhibit cell proliferation, inhibit angiogenesis, promote endothelial cell membrane remodeling, reduce inflammation, and provide cytoprotection. As prodrugs of treprostinil, the treprostinil derivatives described herein can be used to treat a wide variety of conditions, including without limitation: pulmonary hypertension, ischemic diseases (e.g., myocardial ischemia, ischemic stroke, peripheral vascular disease, ischemia of a limb, Raynaud's phenomenon and scleroderma), heart failure (e.g., congestive heart failure), conditions requiring anticoagulation (e.g., post myocardial infarction and post cardiac surgery), atherosclerosis, thrombotic microangiopathy, central retinal vein occlusion, hypertension (e.g., preeclampsia), extracorporeal circulation, inflammatory diseases (e.g., chronic obstructive pulmonary disease [COPD] and psoriasis), renal insufficiency, reproduction and parturition, conditions of unregulated cell growth (e.g., cancers and tumors), celI/tissue preservation, and other therapeutic areas where prostacyclin or treprostinil treatment may provide benefit.

In some embodiments, one or more treprostinil derivatives, or pharmaceutically acceptable salts, solvates, hydrates, clathrates or polymorphs thereof, are used to treat a prostacyclin- or treprostinil-responsive condition selected from the group consisting of pulmonary hypertension, pulmonary fibrosis, peripheral ischemic lesions on the skin (e.g., those caused by scleroderma, Buerger's disease, Raynaud's disease, Raynaud's phenomenon and systemic sclerosis), critical limb ischemia, diabetic neuropathic foot ulcer, kidney malfunction and failure, peripheral vascular disease, atherogenesis (e.g., atherosclerosis), congestive heart failure, tumors, cancers, and pain associated with each of the preceding conditions.

A treprostinil derivative can be used in conjunction with an additional therapeutic agent to treat any condition responsive to treatment with prostacyclin or treprostinil. As a non-limiting example, to treat a vascular (e.g., cardiovascular) disorder a treprostinil derivative can be used in combination with a vascular (e.g., cardiovascular) therapeutic, such as an antiplatelet agent, a phosphodiesterase inhibitor, a calcium channel blocker or an endothelial antagonist, or any combination thereof.

In some embodiments, the treprostinil derivatives described herein are used to treat pulmonary hypertension. An additional therapeutic agent (e.g., a vasoactive agent, a diuretic and/or an anticoagulant) can optionally be administered to treat pulmonary hypertension. In certain embodiments, the pulmonary hypertension is pulmonary arterial hypertension.

Pulmonary hypertension is an increase of blood pressure in the lung vasculature, including the pulmonary artery, pulmonary vein and pulmonary capillaries. Thus, pulmonary hypertension encompasses pulmonary arterial hypertension (PAH) and pulmonary venous hypertension (PVH) (e.g., congestive heart failure). More broadly, pulmonary hypertension encompasses:

WHO Group I—pulmonary arterial hypertension, including idiopathic PAH, heritable PAH (e.g., BMPR2, ALK1 and endoglin [with or without hereditary hemorrhagic telangiectasia]), drug- and toxin-induced PAH, PAH associated with various conditions (e.g., connective tissue disease, HIV infection, portal hypertension, congenital heart disease, schistosomiasis, and chronic hemolytic anemia [e.g., sickle cell disease]), persistent pulmonary hypertension of the newborn, pulmonary veno-occlusive disease (PVOD), and pulmonary capillary hemangiomatosis (PCH);

WHO Group II—pulmonary hypertension owing to left heart disease, including systolic dysfunction, diastolic dysfunction and valvular heart disease;

WHO Group III—pulmonary hypertension owing to lung disease and/or hypoxia, including chronic obstructive pulmonary disease (COPD), interstitial lung disease, other pulmonary diseases with mixed restrictive and obstructive pattern, sleep-disordered breathing, alveolar hypoventilation disorders, chronic exposure to high altitude, and developmental abnormalities;

WHO Group IV—chronic thromboembolic pulmonary hypertension (CTEPH); and

WHO Group V—pulmonary hypertension with unclear multifactorial mechanisms, including hematologic diseases (e.g., myeloproliferative disease and splenectomy), systemic diseases (e.g., sarcoidosis, pulmonary Langerhans cell histiocytosis, lymphangioleiomyomatosis, neurofibromatosis and vasculitis), metabolic disorders (e.g., glycogen storage disease, Gaucher disease and thyroid diseases), and other causes (e.g., tumoral obstruction, fibrosing mediastinitis and chronic renal failure on dialysis).

The therapeutically effective amount and frequency of administration of a treprostinil derivative to treat, e.g., pulmonary hypertension may depend on various factors, including the type of pulmonary hypertension, the severity of the condition, the mode of administration, the age, body weight, general health, gender and diet of the subject, and the response of the subject to the treatment, and can be determined by the treating physician. In certain embodiments, the effective dose of a treprostinil derivative per day is about 0.1-100 mg, 0.1-50 mg, 0.5-50 mg, 0.5-25 mg, 0.5-10 mg, 1-10 mg or 1-5 mg, or as deemed appropriate by the treating physician, which can be administered in a single dose or in divided doses. In further embodiments, the effective dose of a treprostinil derivative per day is about 0.001-2 mg/kg, 0.005-1 mg/kg, 0.01-0.5 mg/kg or 0.01-0.1 mg/kg body weight, or as deemed appropriate by the treating physician.

In some embodiments, a treprostinil derivative is administered, in a single dose or in multiple doses, daily (including one, two, three or more times daily), every two days, every three days, weekly, every 2 weeks, every 3 weeks, monthly, every 6 weeks, every 2 months or every 3 months, or as deemed appropriate by the treating physician. In further embodiments, a treprostinil derivative is administered under a chronic dosing regimen. In certain embodiments, a therapeutically effective amount of a treprostinil derivative is administered over a period of at least 2 weeks, 3 weeks, 1 month, 1.5 months, 2 months, 3 months, 4 months, 5 months, 6 months or longer.

A treprostinil derivative can be administered via any suitable route. Potential routes of administration of a treprostinil derivative include without limitation oral, parenteral (including intradermal, subcutaneous, intramuscular, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). In some embodiments, a treprostinil derivative is administered topically (e.g. dermally, transdermally, mucosally, transmucosally, intranasally, pulmonarily [e.g., by inhalation], or sublingually). In certain embodiments, a treprostinil derivative is administered transdermally (e.g., via a transdermal patch). In other embodiments, a treprostinil derivative is administered orally. In further embodiments, a treprostinil derivative is administered parenterally (e.g., subcutaneously or intravenously, including by injection or infusion).

In some embodiments, a treprostinil derivative is used to treat PAH. In certain embodiments, the treprostinil derivative is administered transdermally, e.g., via a transdermal patch. In further embodiments, an additional therapeutic agent is administered in combination with the treprostinil derivative to treat PAH. The additional therapeutic agent can be administered concurrently with or sequentially to (before or after) administration of the treprostinil derivative. If administered concurrently with the treprostinil derivative, the additional therapeutic agent can be contained in the same composition as the treprostinil derivative or in separate compositions.

In certain embodiments, the additional therapeutic agent for the treatment of PAH is selected from the group consisting of:

vasoactive agents, including without limitation prostaglandins and prostanoids (e.g., prostacyclin [prostaglandin 12] and beraprost), endothelin receptor (e.g., $ET_A$ and/or $ET_B$) antagonists (e.g., ambrisentan, bosentan, sitaxentan and Actelion-1), phosphodiesterase type 5 (PDE5) inhibitors (e.g., sildenafil and tadalafil), activators of soluble guanylate cyclase (e.g., cinaciguat and riociguat), and analogs, derivatives and salts thereof;

diuretics, including without limitation thiazide diuretics (e.g., bendroflumethiazide, chlorothiazide, epitizide and hydrochlorothiazide), thiazide-like diuretics (e.g., chlorthalidone, indapamide and metolazone), and analogs, derivatives and salts thereof;

anticoagulants, including without limitation vitamin K antagonists (e.g., acenocoumarol, atromentin, coumarin, phenindione, phenprocoumon and warfarin), direct thrombin inhibitors (e.g., argatroban, dabigatran, hirudin, lepirudin and bivalirudin), direct factor Xa inhibitors (e.g., apixaban, betrixaban, darexaban, edoxaban, eribaxaban, letaxaban and rivaroxaban), heparin and derivatives thereof (e.g., unfractionated heparin, low molecular weight heparin, fondaparinux and idraparinux), others (e.g., antithrombin, batroxobin and hementin), and analogs, derivatives, fragments and salts thereof; and other kinds of therapeutic agents, including without limitation cardiac glycosides (e.g., digoxin, acetyldigoxin and digoxigenin) and oxygen therapy.

VIII. SYNTHESIS OF TREPROSTINIL DERIVATIVES

A treprostinil (Trp) derivative of Formula (I) in which $R^2$ is hydrogen and —$OR^1$ is derivatized can be prepared by reacting a Trp compound appropriately protected at the octyl hydroxyl group and the carboxyl group (e.g., Compound C in the Examples) with, e.g., a carboxylic acid in the presence of an activating agent (e.g., EDC, DCC, DIC, BOP-Cl, BOP reagent, HATU, HBTU or CDI), or with a pre-prepared activated carbonyl compound (e.g., an acid chloride). The coupling reaction can optionally include an additive (e.g., DMAP, HOSu, HOBT or HOAT) that accelerates the reaction, and can also optionally include a non-nucleophilic or nucleophilic base (e.g., TEA, DIPEA, N-methylmorpholine, pyridine or imidazole). The coupling reaction can be run in a suitable solvent or solvent mixture (e.g., DCM, DMF, THF, dioxane, ethyl acetate or acetonitrile, or any combination thereof). Coupling conditions and reagents, including activating agents, additives and bases, are discussed in, e.g., Handbook of Reagents for Organic Synthesis: Activating Agents and Protecting Groups, A. Pearson and W. Roush, Eds., John Wiley and Sons (1999). The bis-protected Trp compound derivatized at —$OR^1$ can be deprotected to furnish a Trp derivative of Formula (I) using reagents and conditions known in the art. See, e.g., P. Wuts and T. Greene, Greene's Protective Groups in Organic Synthesis, $4^{th}$ Ed., John Wiley and Sons (2006).

A Trp derivative of Formula (I) in which $R^1$ is hydrogen and —$OR^2$ is derivatized can be prepared by appropriately protecting the cyclopentyl hydroxyl group of Compound C, deprotecting the octyl hydroxyl group without deprotecting the cyclopentyl hydroxyl group or the carboxyl group, reacting the octyl hydroxyl group with an activated carbonyl compound (pre-prepared or prepared in situ), and deprotecting the cyclopentyl hydroxyl group and the carboxyl group.

A Trp derivative of Formula (I) in which —$OR^1$ and —$OR^2$ are derivatized with different groups can be prepared by derivatizing —$OR^1$ of Compound C as described herein, deprotecting the octyl hydroxyl group, derivatizing —$OR^2$, and deprotecting the carboxyl group. A Trp derivative of Formula (I) in which —$OR^1$ and —$OR^2$ are derivatized with the same group can be prepared by deprotecting the octyl hydroxyl group of Compound C, derivatizing —$OR^1$ and —$OR^2$ as described herein, and deprotecting the carboxyl group.

A Trp derivative of Formula (II) can be prepared by reacting a Trp compound appropriately protected at the octyl hydroxyl group (e.g., Compound B in the Examples) with an alcohol whose carboxyl group is appropriately protected in the presence of an activating agent as described herein, and deprotecting the octyl hydroxyl group and the carboxyl group.

The synthesis of representative treprostinil derivatives is described in the Examples.

IX. REPRESENTATIVE EMBODIMENTS

The following embodiments of the disclosure are provided by way of example only:

1. A compound of Formula (I):

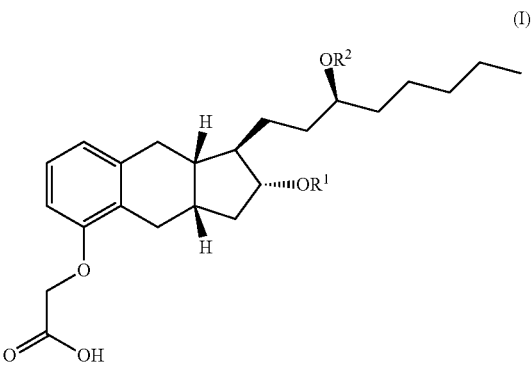

wherein:
$R^1$ and $R^2$ independently are hydrogen,

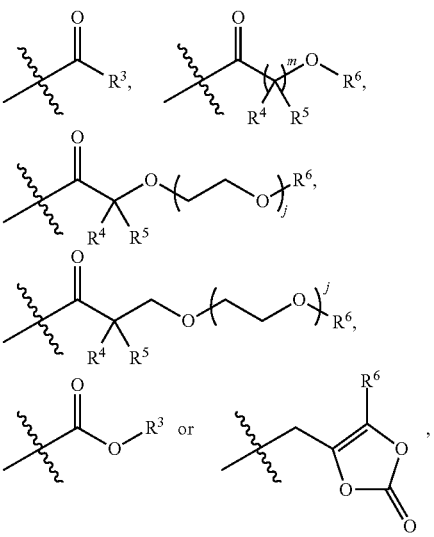

wherein:
R³ in each occurrence independently is alkyl, -alkylaryl, cycloalkyl, heterocyclyl, aryl or heteroaryl, each of which may optionally be substituted;
R⁴ and R⁵ in each occurrence independently are hydrogen, $C_1$-$C_6$ alkyl or $C_3$-$C_6$ cycloalkyl, or R⁴ and R⁵ and the carbon atom to which they are connected form a $C_3$-$C_6$ cycloalkyl ring;
R⁶ in each occurrence independently is hydrogen, R³, —C(=O)R³, —C(=O)OR³ or —C(=O)NR⁹R¹⁰; or R⁶ and R⁴ or R⁵, together with the atoms to which they are connected, form a heterocyclic ring;
R⁹ and R¹⁰ in each occurrence independently are hydrogen, alkyl, -alkylaryl, cycloalkyl, heterocyclyl, aryl or heteroaryl; or
R⁹ and R¹⁰ and the nitrogen atom to which they are connected form a heterocyclic or heteroaryl ring;
j in each occurrence independently is an integer from 0 to 4; and
m in each occurrence independently is an integer from 1 to 10;
or a pharmaceutically acceptable salt, solvate, hydrate, clathrate, polymorph or stereoisomer thereof, with the proviso that:
both R¹ and R² are not hydrogen;
neither —OR¹ nor —OR² forms an acetate;
neither —OR¹ nor —OR² forms a substituted cyclohexane-ester; and
neither —OR¹ nor —OR² forms an ester with or of an amino acid (protected or unprotected), a peptide or a protein.

2. The compound of embodiment 1, wherein R³ in

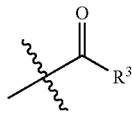

is not alkyl substituted with a nitrogen-containing group, or not cycloalkyl substituted with a carbonyl-containing group.

3. The compound of embodiment 1, wherein neither the alkyl nor the cycloalkyl group, or none of the alkyl, -alkylaryl, cycloalkyl, heterocyclyl, aryl or heteroaryl group, of R³ in

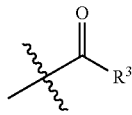

is substituted.

4. The compound of any one of the preceding embodiments, wherein j in each occurrence independently is 0, 1 or 2.

5. The compound of any one of the preceding embodiments, wherein m in each occurrence independently is an integer from 1 to 6.

6. The compound of any one of the preceding embodiments, wherein R¹ and R² independently are

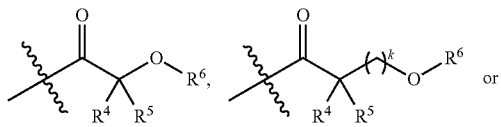

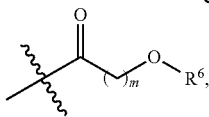

and wherein:
R⁴, R⁵, R⁶ and m are as defined above; and
k in each occurrence independently is an integer from 1 to 9.

7. The compound of embodiment 6, wherein k in each occurrence independently is an integer from 1 to 5.

8. The compound of any one of the preceding embodiments, wherein:
R³ in each occurrence independently is $C_1$-$C_6$ alkyl;
R⁴ and R⁵ in each occurrence independently are hydrogen or $C_1$-$C_3$ alkyl, or R⁴ and R⁵ and the carbon atom to which they are connected form a cyclopropyl ring;
R⁶ in each occurrence independently is hydrogen or R³;
j in each occurrence independently is 0 or 1; and
m in each occurrence independently is 1 or 2.

9. The compound of embodiment 8, wherein:
R³ in each occurrence independently is methyl, ethyl, propyl, isopropyl, butyl, iso-butyl, sec-butyl or tert-butyl;
R⁴ and R⁵ in each occurrence independently are hydrogen, methyl, ethyl, propyl or isopropyl;
R⁶ in each occurrence independently is hydrogen or R³;
j is 0; and
m is 1.

10. The compound of any one of the preceding embodiments, wherein R¹ and R² independently are selected from the group consisting of:
hydrogen,

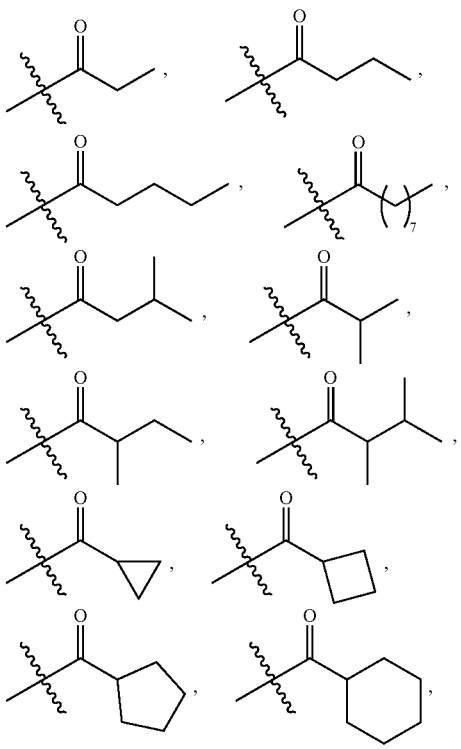

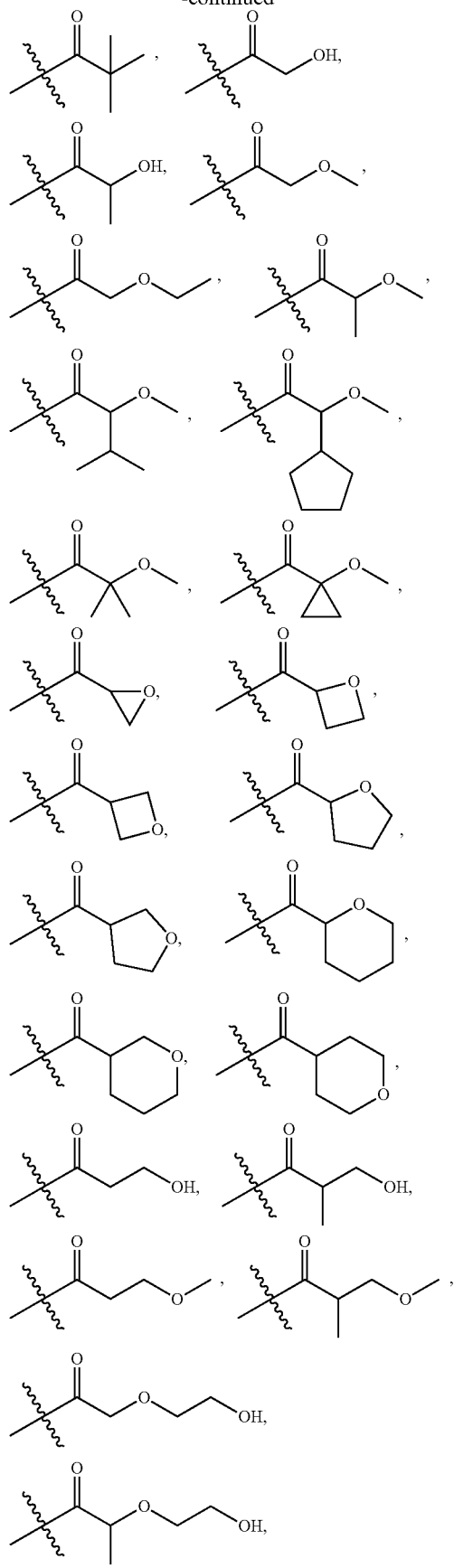
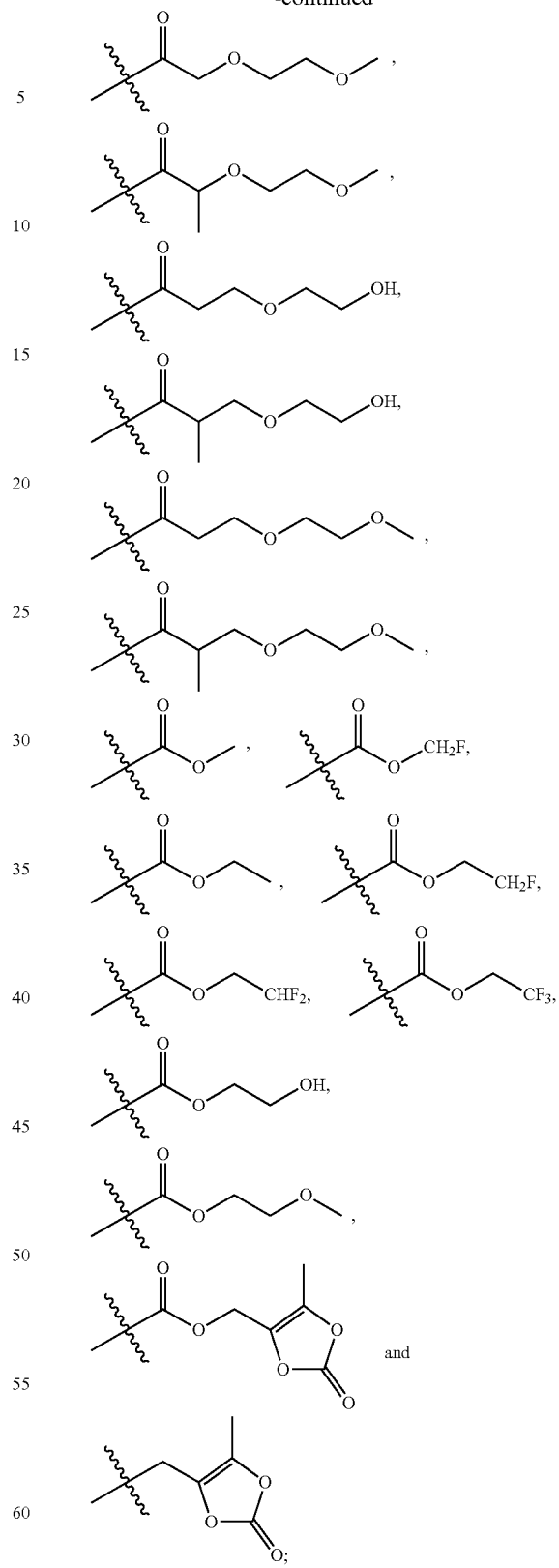
with the proviso that both $R^1$ and $R^2$ are not hydrogen.
11. The compound of embodiment 10, wherein $R^1$ and $R^2$ independently are selected from the group consisting of:

hydrogen,

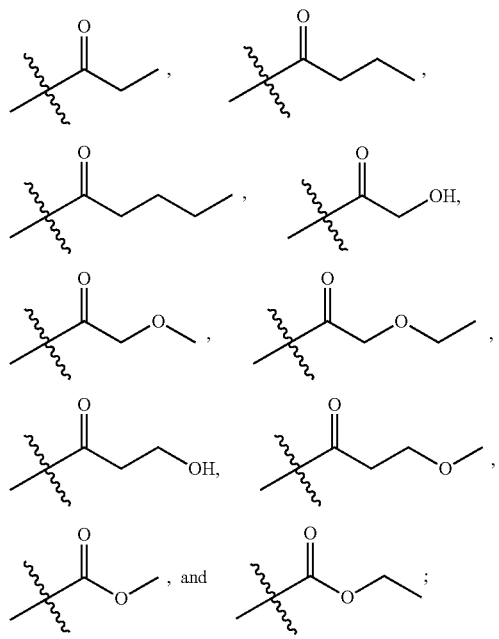

with the proviso that both $R^1$ and $R^2$ are not hydrogen.

12. The compound of any one of the preceding embodiments, wherein both —$OR^1$ and —$OR^2$ are derivatized [Formula (Ic)], optionally with the same group.

13. The compound of any one of embodiments 1 to 11, wherein both —$OR^1$ and —$OR^2$ are not derivatized.

14. The compound of embodiment 13, wherein $R^2$ is hydrogen and —$OR^1$ is derivatized [Formula (Ia)].

15. The compound of embodiment 13, wherein $R^1$ is hydrogen and —$OR^2$ is derivatized [Formula (Ib)].

16. The compound of any one of the preceding embodiments, which is selected from the group consisting of:

Compound Ia-1

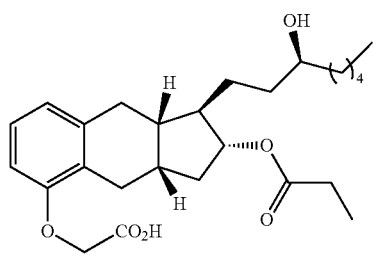

Compound Ia-2

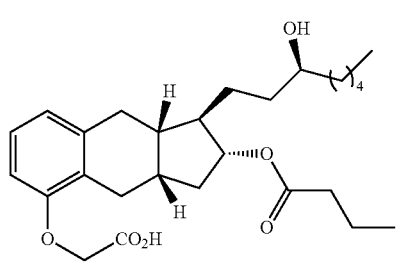

Compound Ia-3

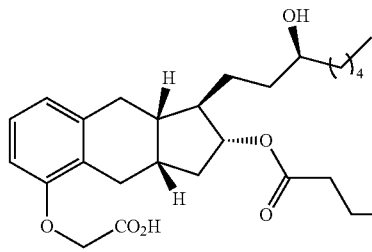

Compound Ia-4

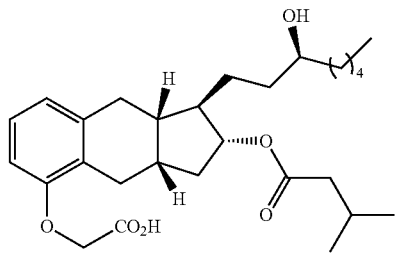

Compound Ia-5

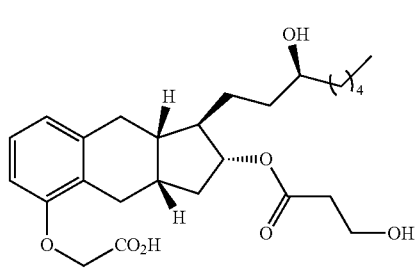

Compound Ia-6

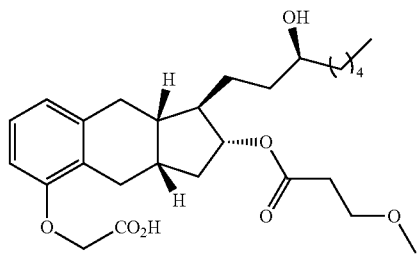

Compound Ia-7

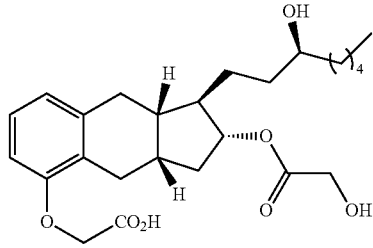

Compound Ia-8

Compound Ia-9
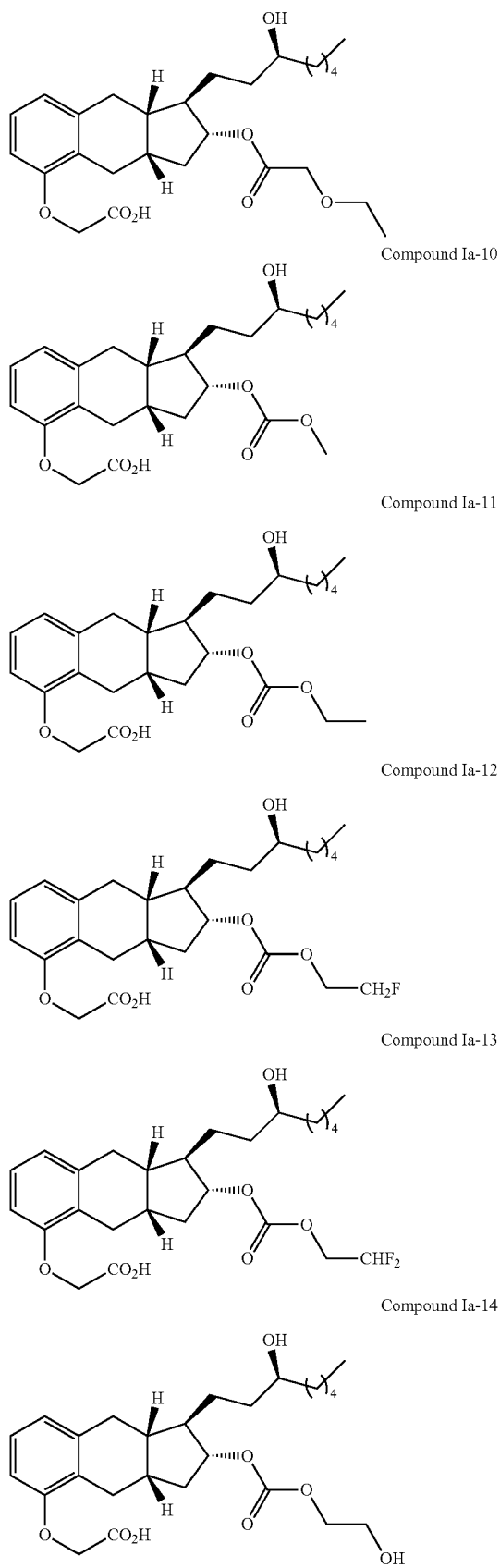
Compound Ia-10
Compound Ia-11
Compound Ia-12
Compound Ia-13
Compound Ia-14
Compound Ia-15
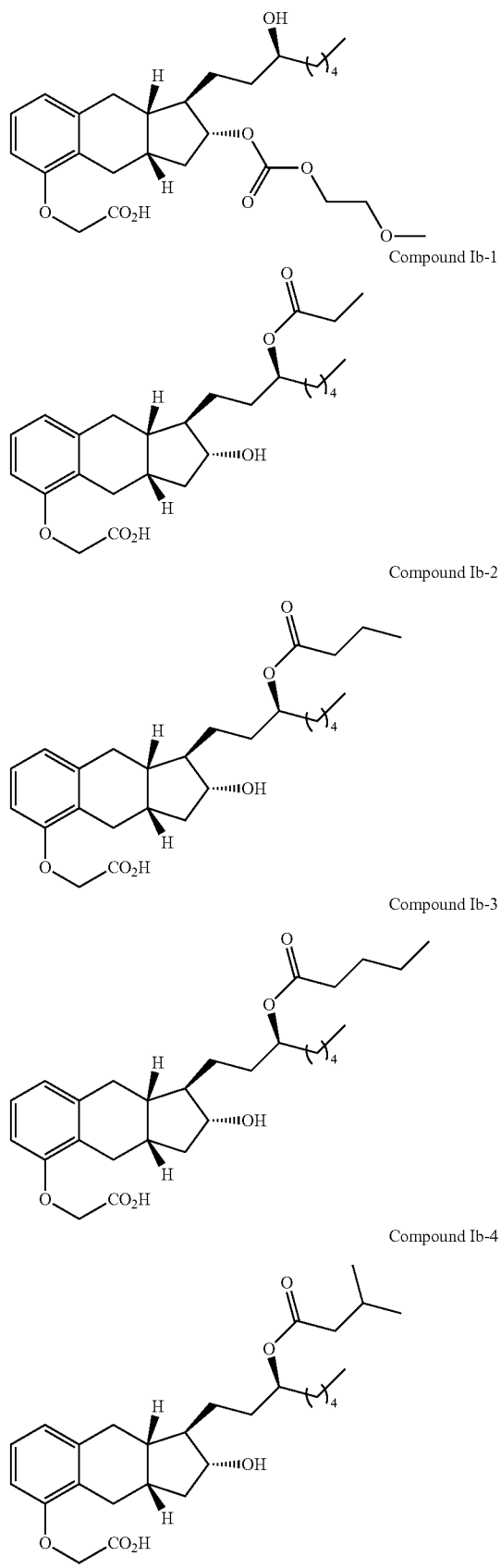
Compound Ib-1
Compound Ib-2
Compound Ib-3
Compound Ib-4

Compound Ib-5

Compound Ib-6

Compound Ib-7

Compound Ib-8

Compound Ib-9

Compound Ib-10

Compound Ib-11

Compound Ib-12

Compound Ib-13
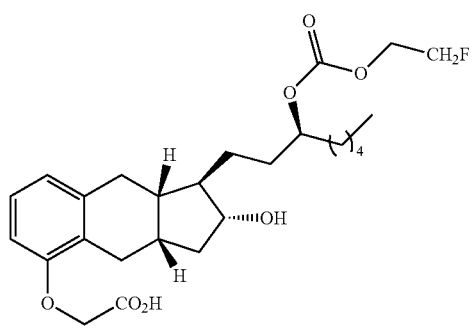
Compound Ib-14
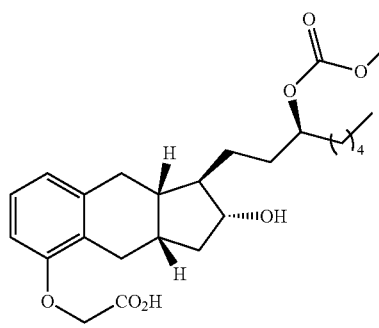
Compound Ib-15
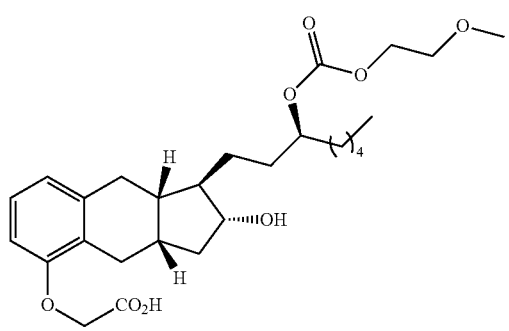
and pharmaceutically acceptable salts, solvates, hydrates, clathrates, polymorphs and stereoisomers thereof.
17. A compound selected from the group consisting of:
Compound Ia-1
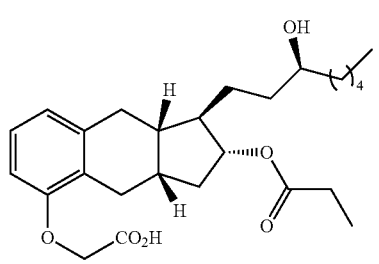
Compound Ia-2
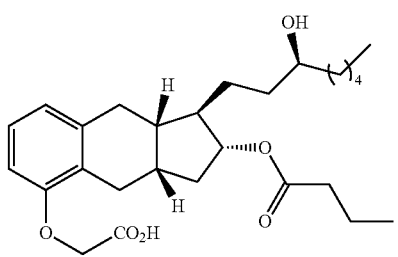
Compound Ia-3
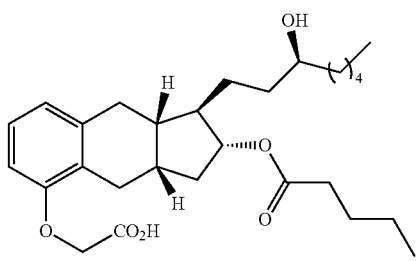
Compound Ia-4
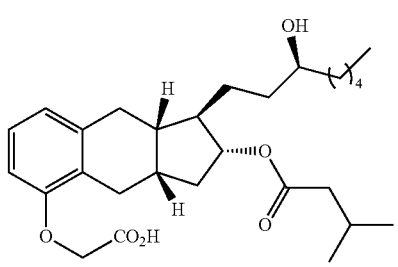
Compound Ia-5
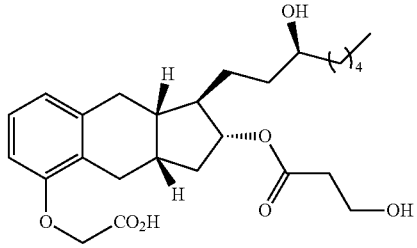
Compound Ia-6
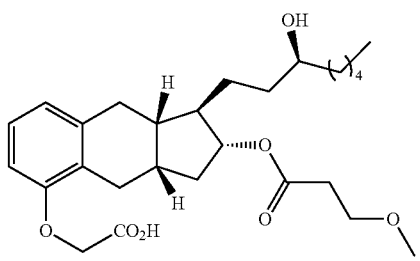
Compound Ia-7
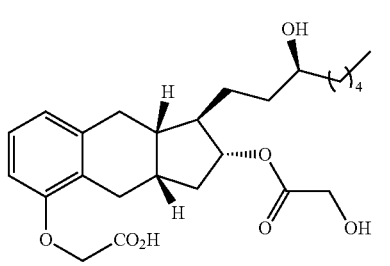

Compound Ia-8
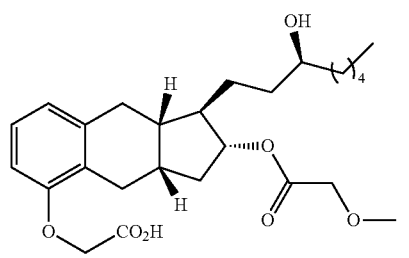
Compound Ia-9
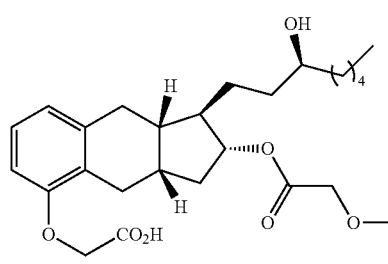
Compound Ia-10
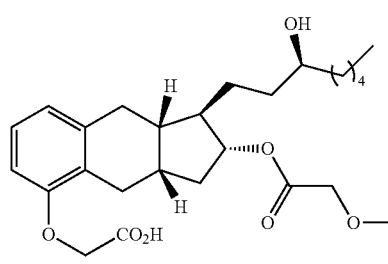
Compound Ia-11
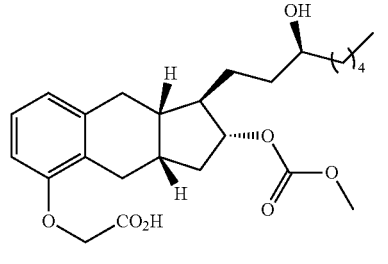
Compound Ia-12
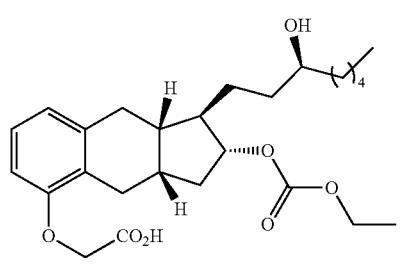
Compound Ia-13
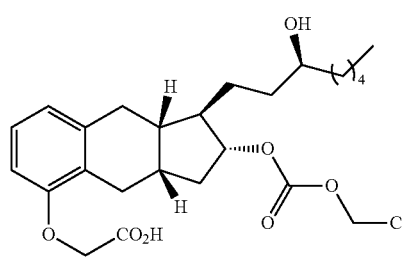
Compound Ia-14
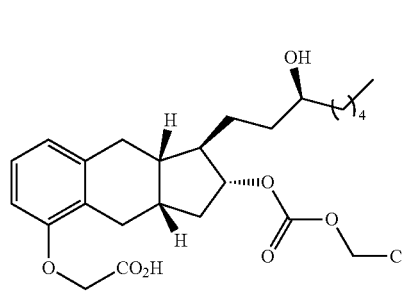
Compound Ia-15
Compound Ib-1
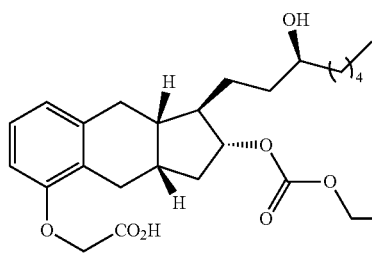
Compound Ib-2
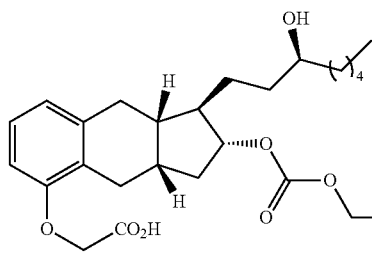
Compound Ib-3
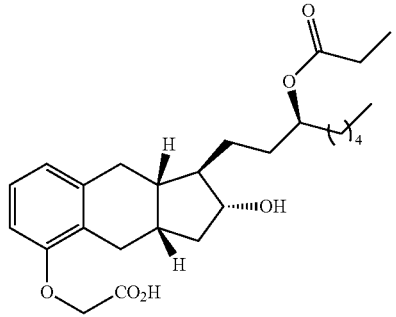

-continued
Compound Ib-4
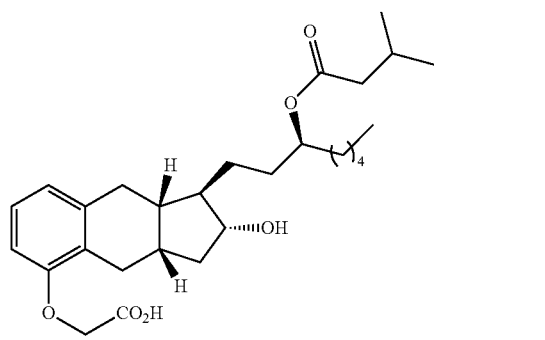
Compound Ib-5
Compound Ib-6
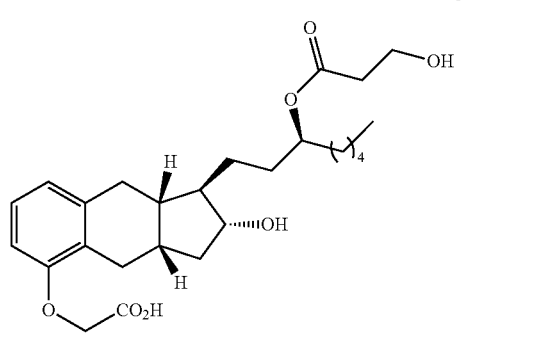
Compound Ib-7
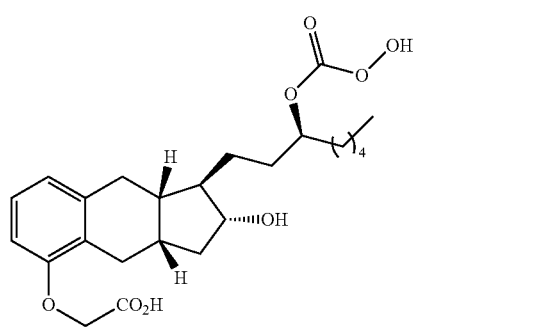
Compound Ib-8
Compound Ib-9
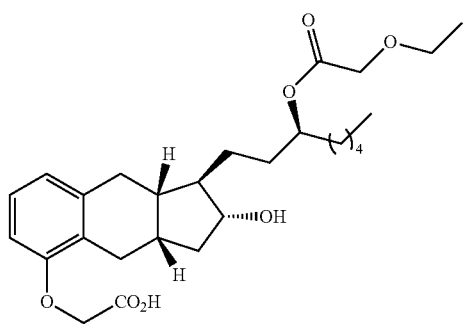
Compound Ib-10
Compound Ib-11
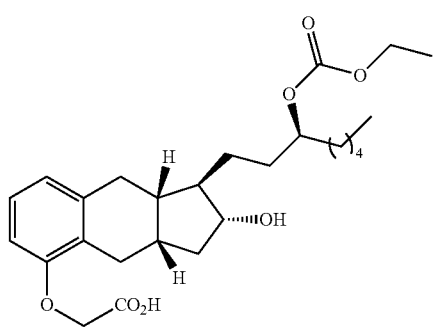

Compound Ib-12

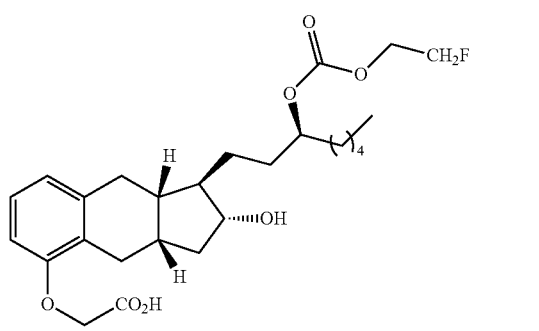

Compound Ib-13

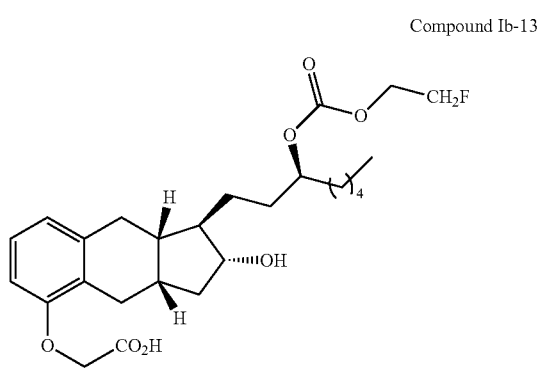

Compound Ib-14

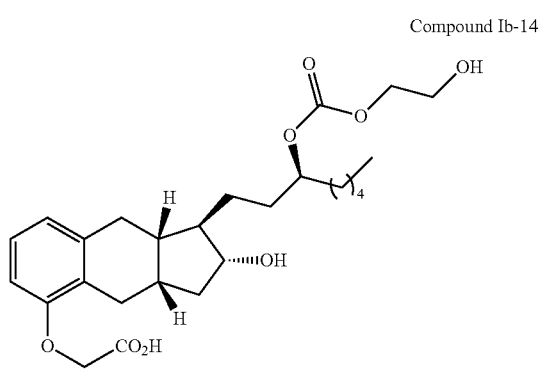

Compound Ib-15

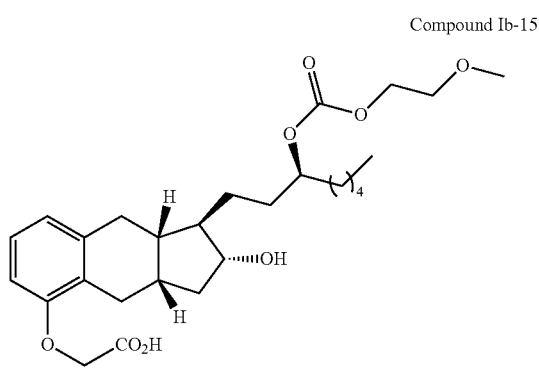

and pharmaceutically acceptable salts, solvates, hydrates, clathrates, polymorphs and stereoisomers thereof.

18. A compound of Formula (II):

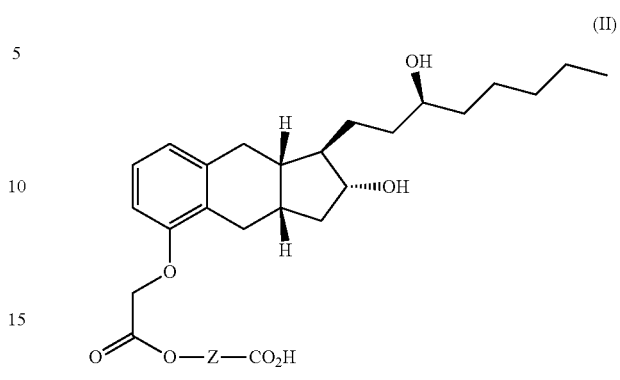

wherein:
—O—Z—$CO_2H$ is

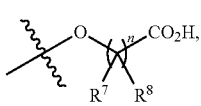

—O-heteroalkyl-$CO_2H$, —O-cyclyl-$CO_2H$, —O—$CH_2$-cyclyl-$CO_2H$, —O-cyclyl-$CH_2$—$CO_2H$, or —O—$CH_2$-cyclyl-$CH_2$—$CO_2H$, each of which may optionally be substituted, wherein:
cyclyl- is -cycloalkyl-, -heterocyclyl-, -aryl- or -heteroaryl-;
$R^7$ and $R^8$ in each occurrence independently are hydrogen, $C_1$-$C_6$ alkyl or $C_3$-$C_6$ cycloalkyl, or $R^7$ and $R^8$ and the carbon atom to which they are connected form a $C_3$-$C_6$ cycloalkyl ring; and
n is an integer from 1 to 10;
or a pharmaceutically acceptable salt, solvate, hydrate, clathrate, polymorph or stereoisomer thereof, with the proviso that:
—O—Z—$CO_2H$ is not

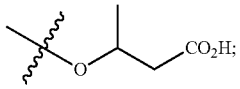

and
—O—Z—$CO_2H$ does not contain a sugar moiety.

19. The compound of embodiment 18, wherein n is an integer from 1 to 6.

20. The compound of embodiment 18, wherein —O—Z—$CO_2H$ does not contain a -heterocyclyl- group, or a substituted -heterocyclyl- group.

21. The compound of embodiment 18, wherein —O—Z—$CO_2H$ is

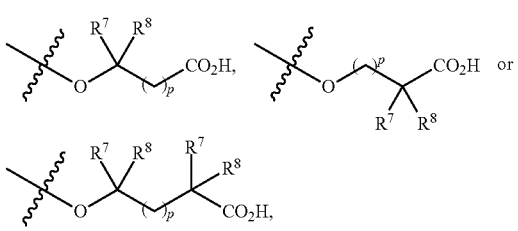

and wherein:

R⁷ and R⁸ are as defined above;

p is an integer from 1 to 9; and q is an integer from 0 to 8;

with the proviso that —O—Z—CO₂H is not

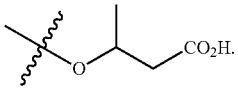 [SMILES: *OC(C)CC(=O)O]

22. The compound of embodiment 21, wherein p is an integer from 1 to 5, and q is an integer from 0 to 4.

23. The compound of embodiment 21 or 22, wherein both R⁷ and R⁸ are hydrogen, and p is an integer from 1 to 5 or from 1 to 3 (or each occurrence of R⁷ and R⁸ is hydrogen, and q is an integer from 0 to 4 or from 0 to 2).

24. The compound of embodiment 21 or 22, wherein —O—Z—CO₂H is

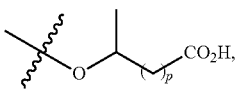

and p is 2, 3, 4 or 5.

25. The compound of embodiment 18, wherein —O—Z—CO₂H is —O-heteroalkyl-CO₂H, and —O-heteroalkyl-CO₂H is selected from the group consisting of:

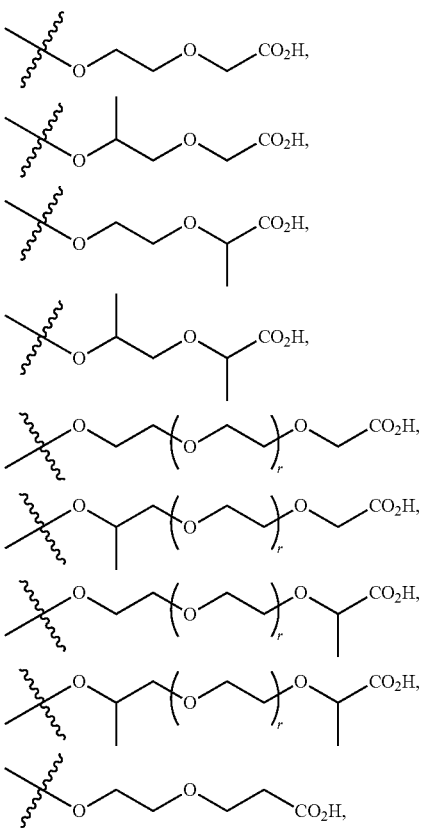

-continued

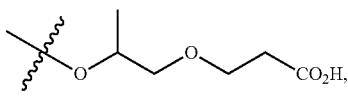

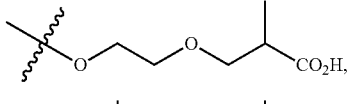

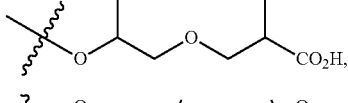

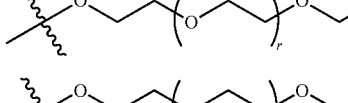

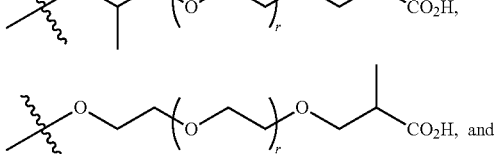

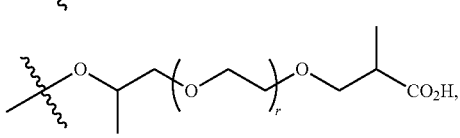

wherein r is each of 1, 2 and 3.

26. The compound of embodiment 25, wherein —O—Z—CO₂H is

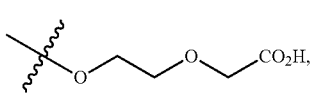

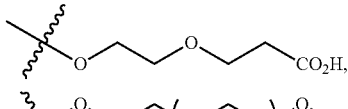

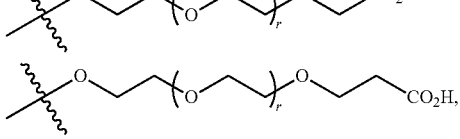

and r is 1, 2 or 3.

27. The compound of embodiment 18, wherein —O—Z—CO₂H is —O-cycloalkyl-CO₂H, —O—CH₂-cycloalkyl-CO₂H, —O-cycloalkyl-CH₂—CO₂H, or —O—CH₂-cycloalkyl-CH₂—CO₂H, and for each of the preceding moieties -cycloalkyl- is:

1,2-cyclopropyl (cis or trans); or 1,3-cyclobutyl (cis or trans) or 1,2-cyclobutyl (cis or trans); or 1,3-cyclopentyl (cis or trans) or 1,2-cyclopentyl (cis or trans); or 1,4-cyclohexyl (cis or trans), 1,3-cyclohexyl (cis or trans), or 1,2-cyclohexyl (cis or trans).

28. The compound of embodiment 27, wherein —O—Z—CO₂H is selected from the group consisting of:

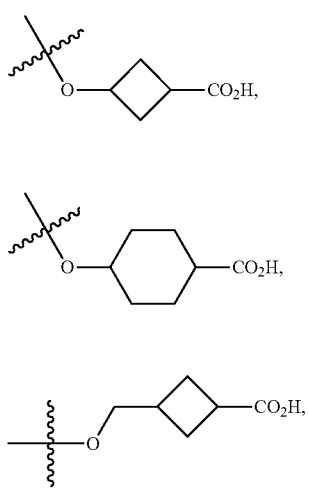
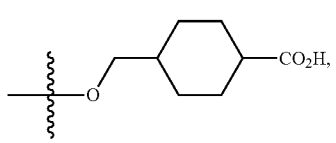
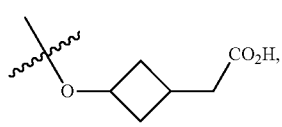
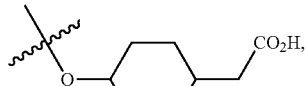
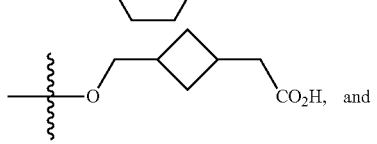
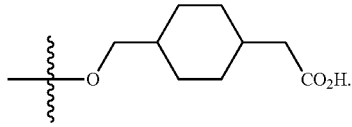
29. The compound of any one of embodiments 18 to 28, which is selected from the group consisting of:
Compound II-1
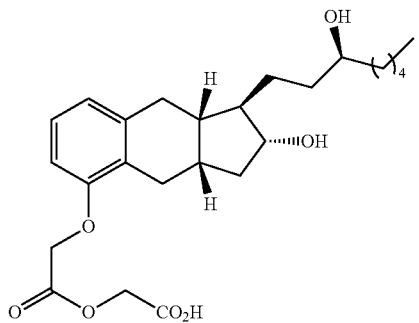
Compound II-2
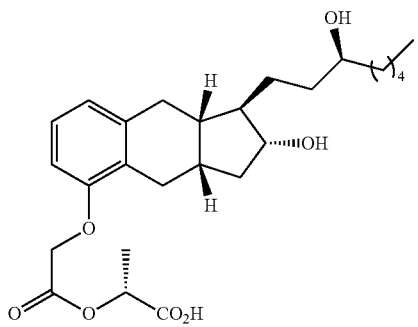
Compound II-3
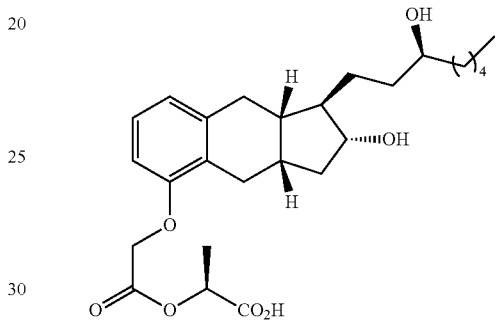
Compound II-4
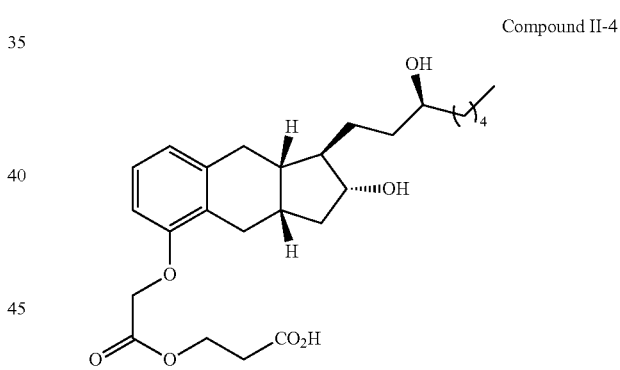
Compound II-5
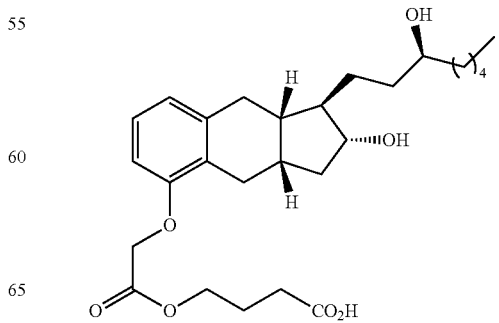

Compound II-6

Compound II-10

Compound II-7

Compound II-11

Compound II-8

Compound II-12

Compound II-9

Compound II-13

Compound II-14
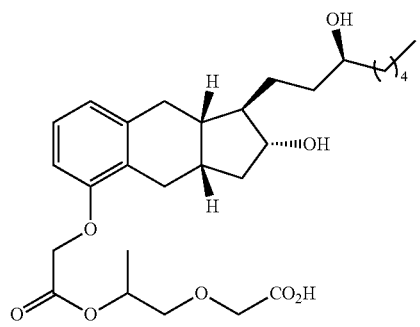
Compound II-15
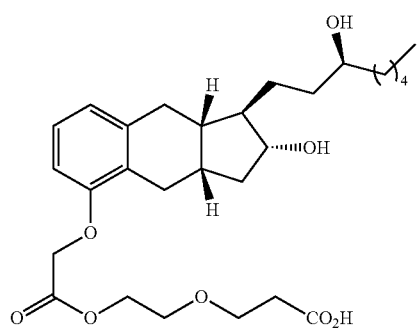
Compound II-16
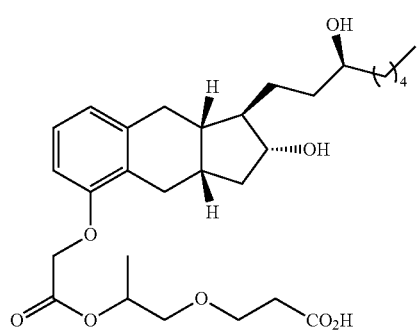
Compound II-17
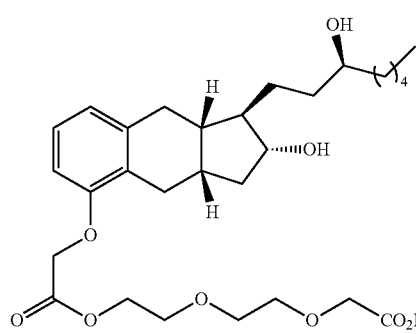
Compound II-18
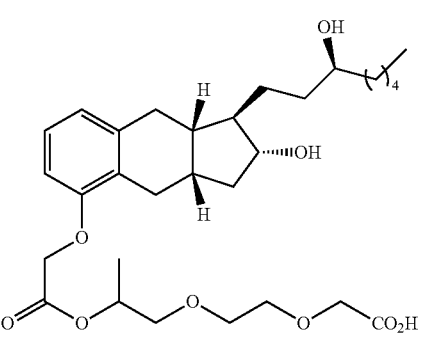
Compound II-19
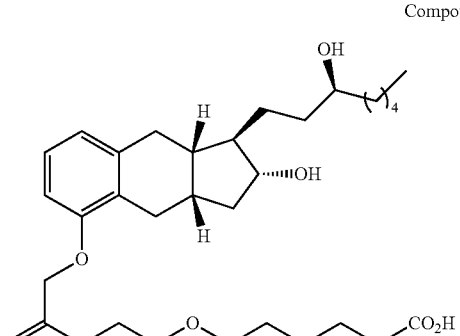
Compound II-20
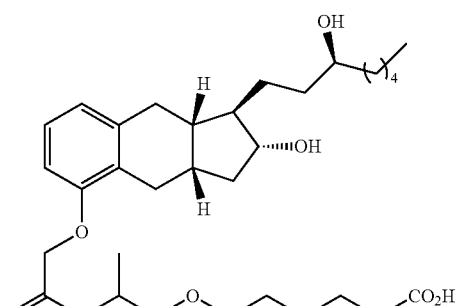
Compound II-21
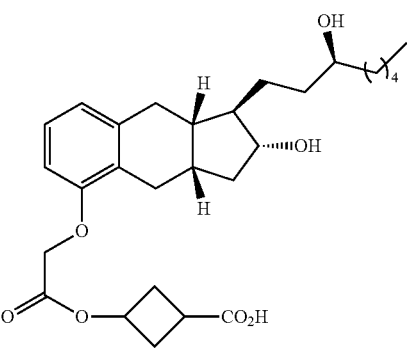

Compound II-22
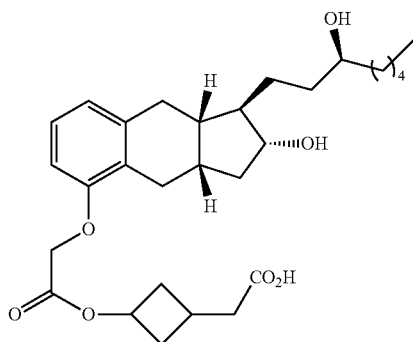
Compound II-23
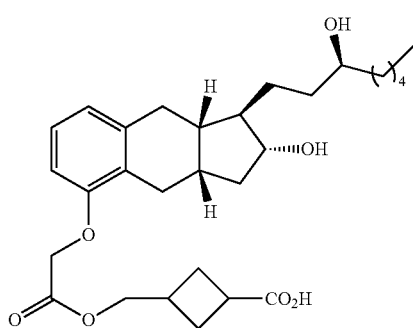
Compound II-24
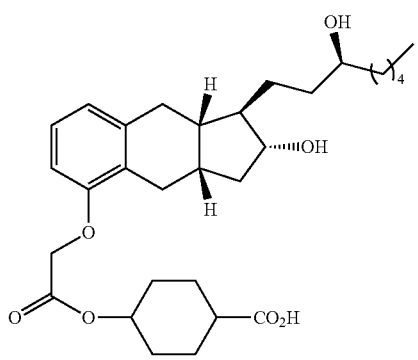
Compound II-25
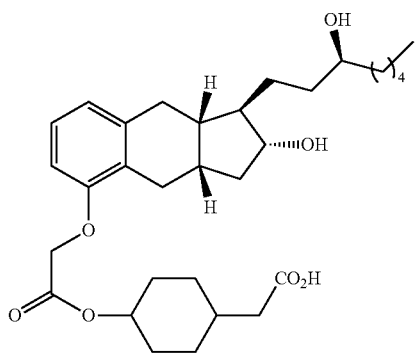
Compound II-26
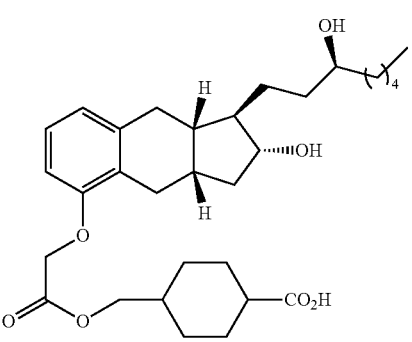
and pharmaceutically acceptable salts, solvates, hydrates, clathrates, polymorphs and stereoisomers thereof.
30. The compound of embodiment 29, which is selected from the group consisting of:
Compound II-4
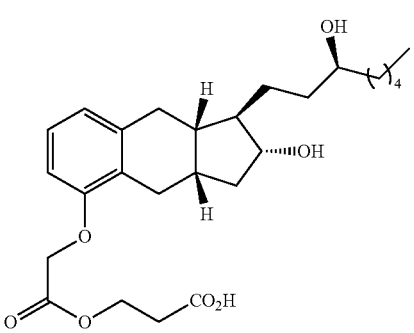
Compound II-5
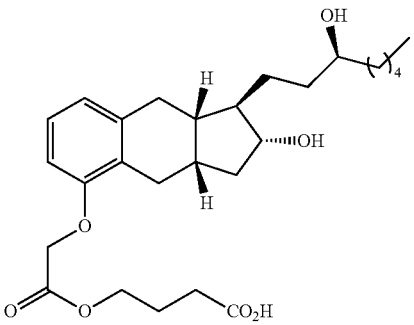
Compound II-7
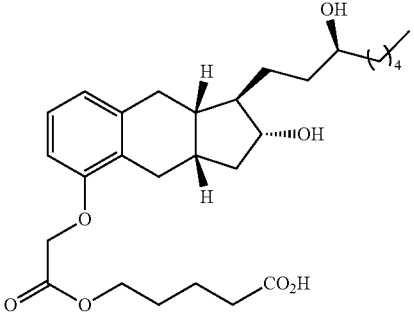

Compound II-9
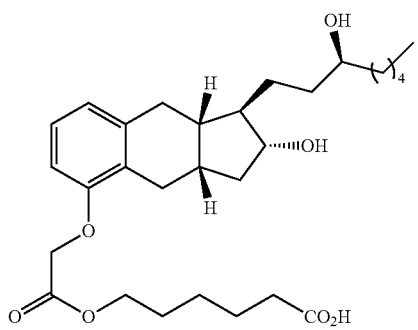
Compound II-13
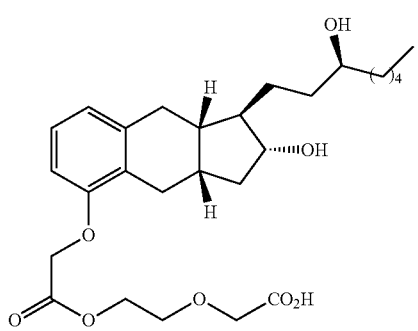
Compound II-15
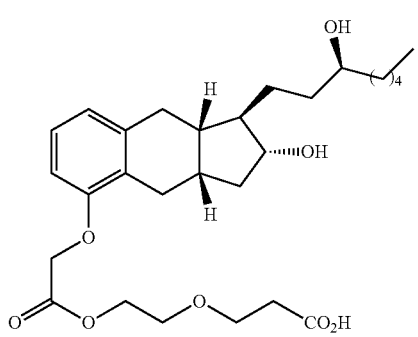
and pharmaceutically acceptable salts, solvates, hydrates, clathrates, polymorphs and stereoisomers thereof.
31. A compound selected from the group consisting of:
Compound II-1
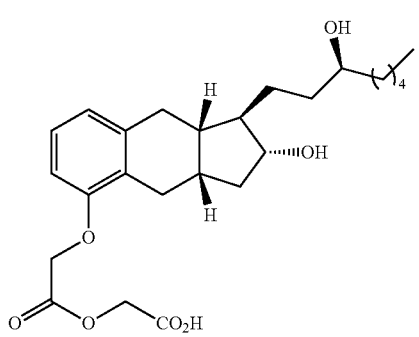
Compound II-2
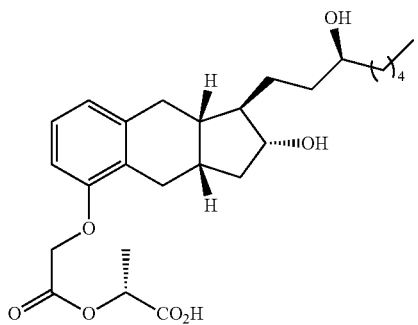
Compound II-3
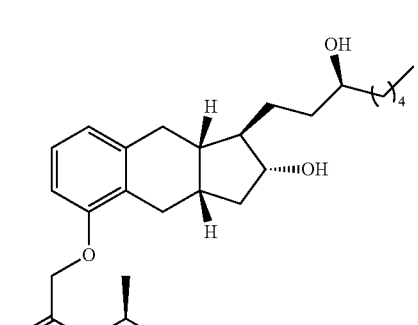
Compound II-4
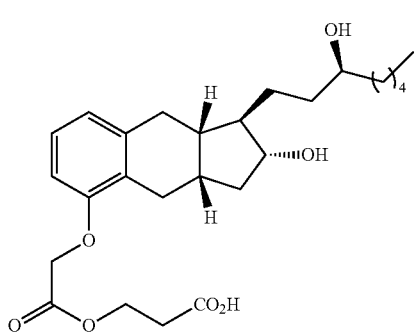
Compound II-5
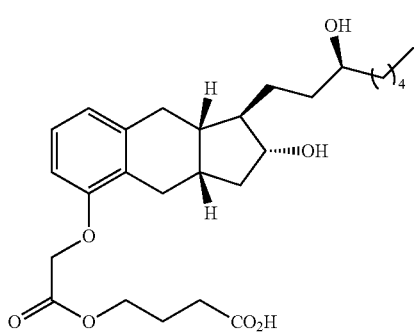

-continued
Compound II-6
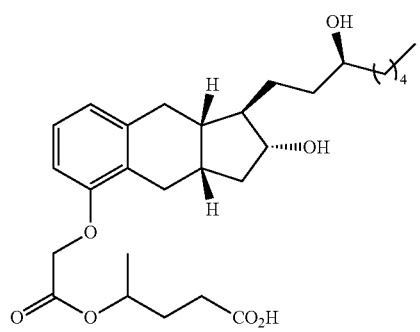
Compound II-7
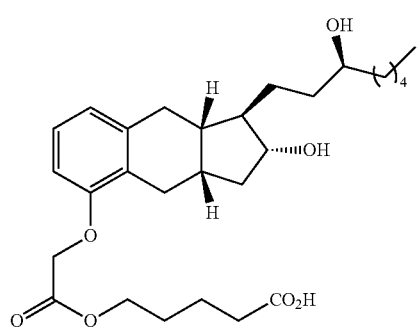
Compound II-8
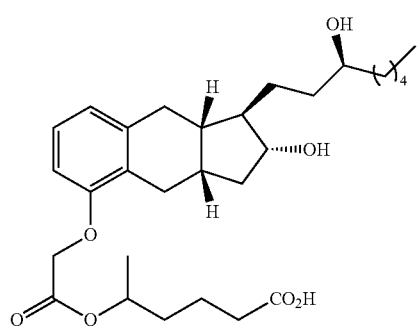
Compound II-9
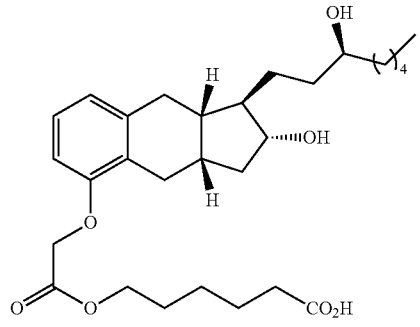
-continued
Compound II-10
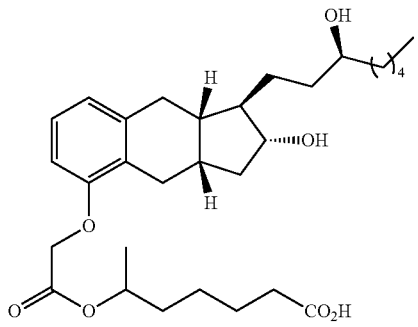
Compound II-11
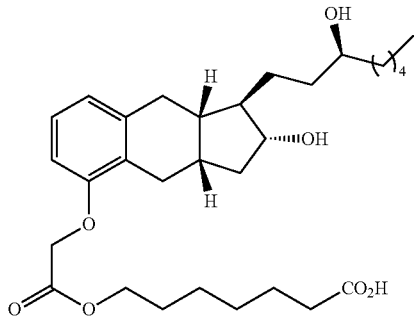
Compound II-12
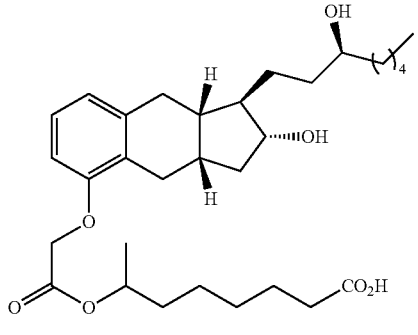
Compound II-13
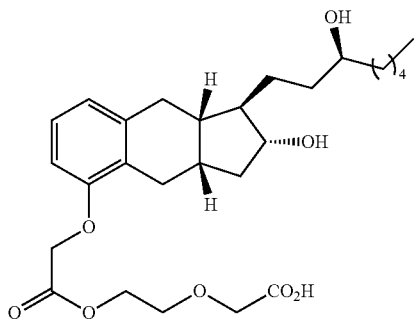

Compound II-14
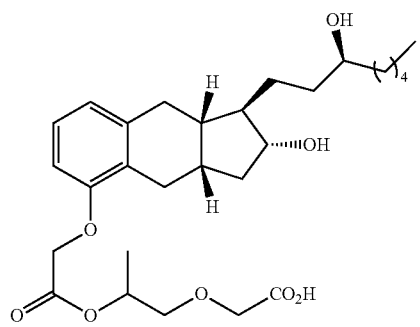
Compound II-15
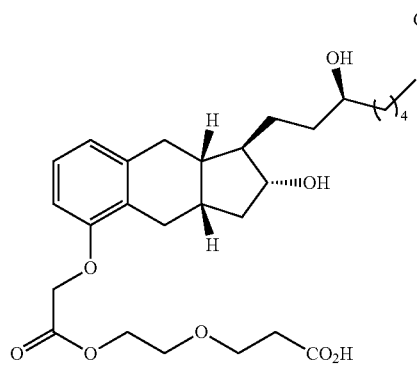
Compound II-16
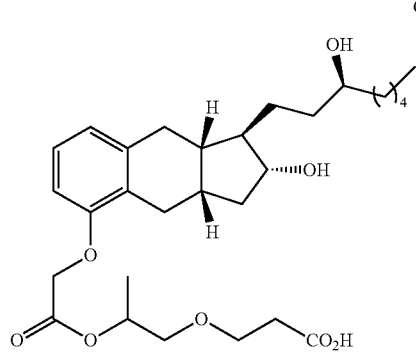
Compound II-17
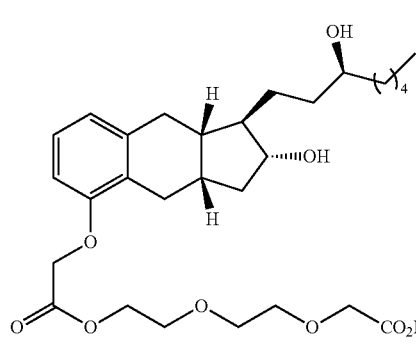
Compound II-18
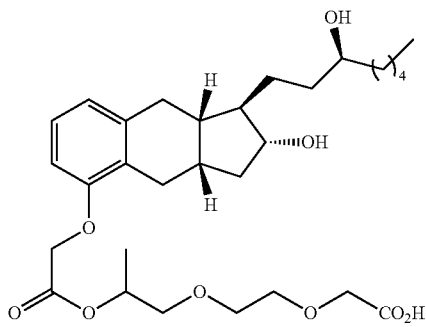
Compound II-19
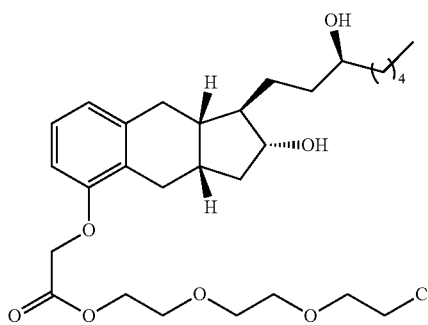
Compound II-20
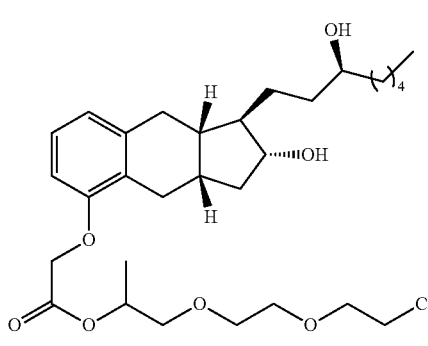
Compound II-21
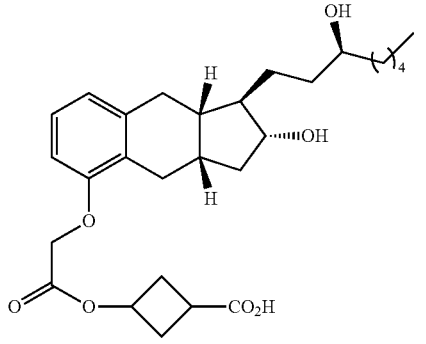

Compound II-22
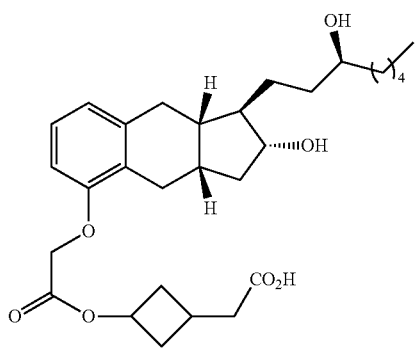
Compound II-23
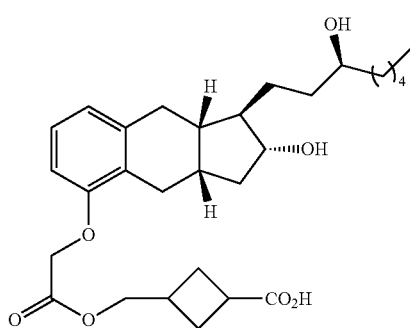
Compound II-24
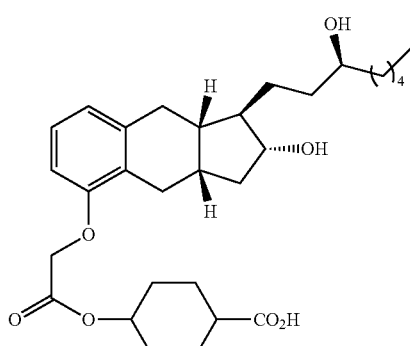
Compound II-25
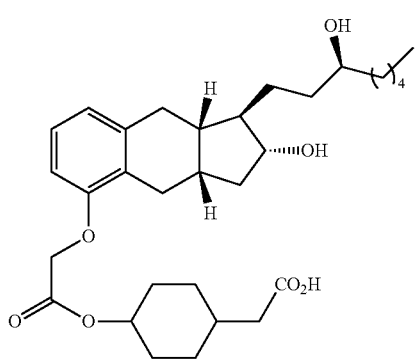
Compound II-26
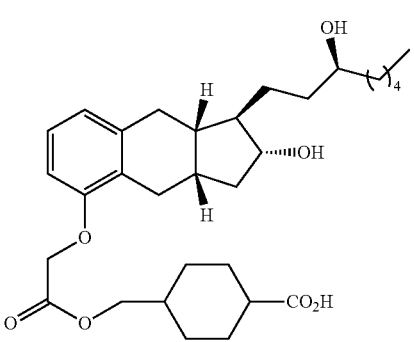
and pharmaceutically acceptable salts, solvates, hydrates, clathrates, polymorphs and stereoisomers thereof.
32. The compound of embodiment 31, which is selected from the group consisting of:
Compound II-4
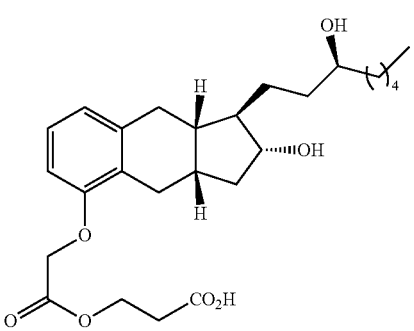
Compound II-5
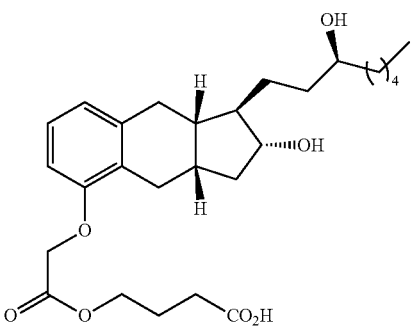
Compound II-7
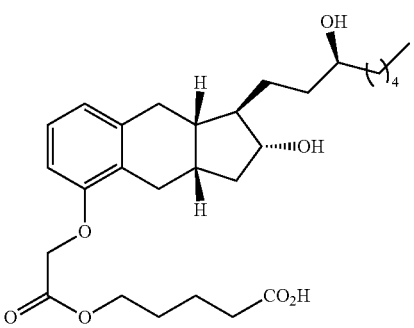

-continued

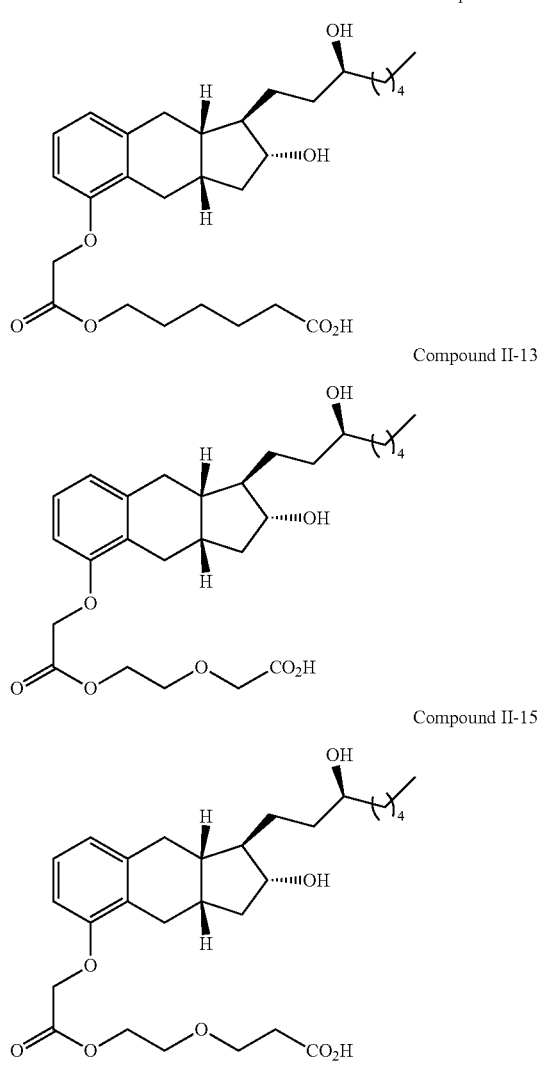

Compound II-9

Compound II-13

Compound II-15 and pharmaceutically acceptable salts, solvates, hydrates, clathrates, polymorphs and stereoisomers thereof.

33. A pharmaceutical composition comprising a compound of any one of embodiments 1 to 32, or a pharmaceutically acceptable salt, solvate, hydrate, clathrate, polymorph or stereoisomer thereof, and one or more pharmaceutically acceptable excipients or carriers.

34. The composition of embodiment 33, wherein the compound is a compound of embodiment 17 or 31, or a pharmaceutically acceptable salt, solvate, hydrate, clathrate, polymorph or stereoisomer thereof.

35. The composition of embodiment 34, wherein the compound is a compound of embodiment 17 or 32, or a pharmaceutically acceptable salt, solvate, hydrate, clathrate, polymorph or stereoisomer thereof.

36. The composition of any one of embodiments 33 to 35, which is configured for transdermal delivery of the compound.

37. The composition of embodiment 36, which is configured as a transdermal patch.

38. A method of treating a medical condition responsive to treatment with treprostinil, comprising administering to a subject in need of treatment a therapeutically effective amount of a compound of any one of embodiments 1 to 32, or a pharmaceutically acceptable salt, solvate, hydrate, clathrate, polymorph or stereoisomer thereof.

39. The method of embodiment 38, wherein the medical condition is selected from the group consisting of pulmonary hypertension, pulmonary fibrosis, peripheral ischemic lesions on the skin (e.g., those caused by scleroderma, Buerger's disease, Raynaud's disease, Raynaud's phenomenon and systemic sclerosis), critical limb ischemia, diabetic neuropathic foot ulcer, kidney malfunction and failure, peripheral vascular disease, atherogenesis (e.g., atherosclerosis), congestive heart failure, tumors, cancers, and pain associated with each of the preceding conditions.

40. The method of embodiment 39, wherein the medical condition is pulmonary hypertension.

41. The method of embodiment 40, wherein the medical condition is pulmonary arterial hypertension.

42. The method of any one of embodiments 38 to 41, wherein the compound is a compound of embodiment 17 or 31, or a pharmaceutically acceptable salt, solvate, hydrate, clathrate, polymorph or stereoisomer thereof.

43. The method of embodiment 42, wherein the compound is a compound of embodiment 17 or 32, or a pharmaceutically acceptable salt, solvate, hydrate, clathrate, polymorph or stereoisomer thereof.

44. The method of any one of embodiments 38 to 43, wherein the route of administration of the compound comprises oral, parenteral (e.g., intradermal, subcutaneous, intramuscular, intravascular, intravenous, intraarterial, intramedullary or intrathecal), intracavitary, intraperitoneal, or topical (e.g., dermal/epicutaneous, transdermal, mucosal, transmucosal, intranasal [e.g., by nasal spray or drop], intraocular [e.g., by eye drop], pulmonary [e.g., by inhalation], buccal, sublingual, rectal or vaginal), or any combination thereof.

45. The method of embodiment 44, wherein the compound is administered transdermally (e.g., via a transdermal patch).

46. The method of any one of embodiments 38 to 45, wherein:

the medical condition is pulmonary arterial hypertension;

the compound is a compound of embodiment 17 or 31, or a pharmaceutically acceptable salt, solvate, hydrate, clathrate, polymorph or stereoisomer thereof; and the compound is administered transdermally (e.g., via a transdermal patch).

47. The method of any one of embodiments 38 to 46, further comprising administering an additional therapeutic agent.

48. The method of embodiment 47, wherein the additional therapeutic agent comprises a vasoactive agent, a diuretic or an anticoagulant, or any combination thereof.

49. A kit comprising:

a compound of any one of embodiments 1 to 32, or a pharmaceutically acceptable salt, solvate, hydrate, clathrate, polymorph or stereoisomer thereof; and instructions for administering the compound to treat a medical condition responsive to treatment with treprostinil.

50. The kit of embodiment 49, wherein the compound is contained or incorporated in a device or system configured for transdermal delivery (e.g., a transdermal patch).

51. The kit of embodiment 49 or 50, wherein the medical condition is pulmonary hypertension (e.g., pulmonary arterial hypertension).

X. EXAMPLES

The following examples are intended only to illustrate the disclosure. Other procedures, methodologies, assays, conditions and reagents may alternatively be used as appropriate.

Biological Assays of Treprostinil Derivatives

Example 1. Stability Assays of Treprostinil Derivatives

The following three stability assays were conducted on treprostinil derivatives, with the results shown in Table 1.

(Test 1)

Human liver microsomal stability assay was conducted by incubating 0.5 µM test compound at 37° C. for up to 45 minutes in 50 mM potassium phosphate buffer (pH 7.4) containing 0.5 mg of microsomal protein and 50 µL of NADPH-generating system (7.8 mg of glucose 6-phosphate, 1.7 mg of NADPH and 6 U of glucose 6-phosphate dehydrogenase per mL in 2% w/v of sodium bicarbonate). At 0, 5, 15, 30 and 45 min, an aliquot was taken and quenched with internal standard-containing stop solution. No co-factor controls at 45 min were prepared. After incubation, the samples were analyzed by LC-MS/MS. Peak area ratios of analyte to internal standard were used to calculate the intrinsic clearance. The intrinsic clearance ($CL_{int}$) was determined from the first-order elimination constant by non-linear regression. Formation of the active drug treprostinil (Compound A) over the time course was monitored by LC-MS/MS analysis.

(Test 2)

Human plasma stability assay was conducted by incubating 0.5 µM test compound at 37° C. for up to 120 min in heparinated human plasma. At 0, 5, 15, 30, 60, 120 and 240 min, an aliquot was taken and quenched with internal standard-containing stop solution. After incubation, the samples were analyzed by LC-MS/MS. Peak area ratios of analyte to internal standard were used to calculate the half-life. Formation of the active drug Compound A over the time course was monitored by LC-MS/MS analysis.

(Test 3)

Human skin homogenate stability assay was conducted in a similar manner as the human liver microsomal stability assay, by incubating 0.5 µM test compound at 37° C. for up to 45 min in 50 mM potassium phosphate buffer (pH 7.4) containing 0.5 mg of human skin homogenate protein and 50 µL of NADPH-generating system (7.8 mg of glucose 6-phosphate, 1.7 mg of NADPH and 6 U of glucose 6-phosphate dehydrogenase per mL in 2% w/v of sodium bicarbonate). At 0, 5, 15, 30 and 45 min, an aliquot was taken and quenched with internal standard-containing stop solution. No co-factor controls at 45 min were prepared. After incubation, the samples were analyzed by LC-MS/MS. Peak area ratios of analyte to internal standard were used to calculate the intrinsic clearance. The intrinsic clearance ($CL_{int}$) was determined from the first-order elimination constant by non-linear regression. Formation of the active drug Compound A over the time course was monitored by LC-MS/MS analysis.

Results (half-life) of the three stability assays described above are shown in Table 1. For Table 1, the code for the half-life of the test compounds in the assays is:

A=<15 min
B=15-30 min
C=31-60 min
D=>60 min

TABLE 1

| Cmpd No. | MW (g/mol) | m/z [M + Na]+ | Test 1 $T_{1/2}$ | Test 2 $T_{1/2}$ | Test 3 $T_{1/2}$ | Test 4 |
|---|---|---|---|---|---|---|
| A | 390 | 413 | | | | +++ |
|   |     |     | | | | +++ |
| Ia-1 | 446 | 469 | A | D | D | + |
|      |     |     |   |   |   | + |
|      |     |     |   |   |   | + |
| Ia-3 | 474 | 497 | A | D | D | + |
|      |     |     |   |   |   | + |
| Ia-7 | 448 | 471 | A | D | D |   |
| Ia-8 | 462 | 485 | A | D | D | +++ |
|      |     |     |   |   |   | +++ |
|      |     |     |   |   |   | ++ |
| Ia-9 | 476 | 499 | A | D | D |   |
| Ia-10 | 448 | 471 | A | D | D | ++ |
|       |     |     |   |   |   | ++ |
| Ia-11 | 462 | 485 | A | D | D | ++ |
|       |     |     |   |   |   | ++ |
|       |     |     |   |   |   | ++ |
| Ia-14 | 478 | 501 | C | D | D | +++ |
|       |     |     |   |   |   | +++ |
|       |     |     |   |   |   | +++ |
| Ib-8 | 462 | 485 | A | D | D |   |
| Ib-10 | 448 | 471 | A | D | D |   |
| II-1 | 448 | 471 | C | D | D | +++ |
|      |     |     |   |   |   | ++ |
| II-2 | 462 | 485 | C | D | D | ++++ |
|      |     |     |   |   |   | ++++ |
|      |     |     |   |   |   | ++++ |
| II-4 | 462 | 485 | B | D | D | +++ |
|      |     |     |   |   |   | +++ |

Example 2. Skin Flux Assay of Treprostinil Derivatives (Test 4)

A skin flux assay was performed using a vertical Franz diffusion cell having a diffusion area of 0.64 cm² and a volume of 7.5 mL. The assay was conducted at 32° C. with continuous stirring. Heat-separated human cadaver epidermis was used in the assay, the epidermis being stored at −20° C. after the heat stripping procedure. The human epidermis was thawed prior to being mounted on the diffusion cell. A test compound was applied on the skin, and the diffusion cell was closed by screw-cap. At various time intervals, whole medium or receptor medium was replaced by fresh medium. Part of the collected medium was used to calculate the skin flux of the test compound. The skin flux of various test compounds was evaluated using human epidermis from different donors. N=4 replicates were performed for each test compound tested on human epidermis from a particular donor.

Results of the skin flux assay are shown in Table 1 above. For Table 1, the code for the average skin flux of the test compounds tested on human epidermis from a particular donor is:

+=low to moderate skin flux
++=medium skin flux
+++=high skin flux
++++=very high skin flux

Synthesis of Treprostinil Derivatives

Representative syntheses of compounds of Formulas (I) and (II) are shown below.

Synthesis of {2-hydroxy-1-[3-(tetrahydropyran-2-yloxy)octyl]-2,3,3a,4,9,9a-hexahydro-1H-cyclopenta[b]naphthalen-5-yloxy}acetic Acid Benzyl Ester (Compound C)

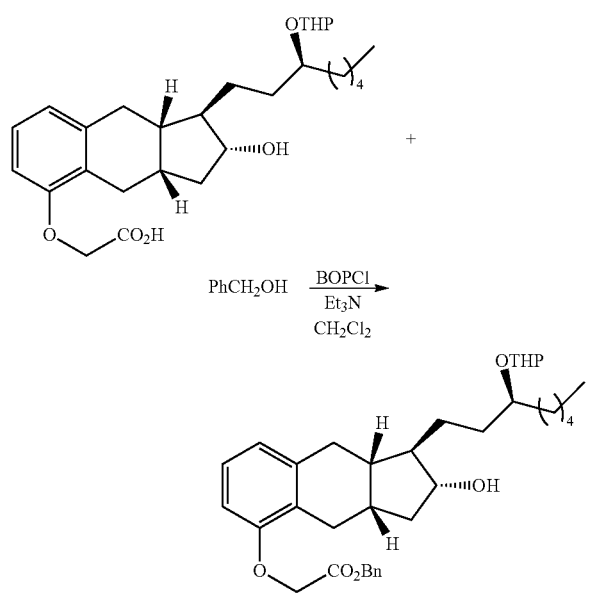

A solution of {2-hydroxy-1-[3-(tetrahydropyran-2-yloxy)octyl]-2,3,3a,4,9,9a-hexahydro-1H-cyclopenta[b]naphthalen-5-yloxy}acetic acid (Compound B) (2 g, 4.21 mmol), benzyl alcohol (2.47 g, 22.9 mmol) and triethylamine (7.2 g, 71.3 mmol) in dichloromethane (DCM) (20 mL) was treated with bis(2-oxo-3-oxazolidinyl)phosphinic chloride (BOP-Cl) (7.8 g, 30.7 mmol) at 0° C. and stirred at room temperature (RT) for 2 hr. The reaction mixture was diluted with methyl-tert-butyl ether (MTBE) and washed with water and then brine, dried over sodium sulfate and concentrated under vacuum. The residue was purified by silica gel chromatography to provide Compound C. MS: m/z 587 [M+Na]+

Example 3. Synthesis of [1-(3-hydroxyoctyl)-2-(2-methoxyacetoxy)-2,3,3a,4,9,9a-hexahydro-1H-cyclopenta[b]naphthalen-5-yloxy]acetic Acid (Compound Ia-8)

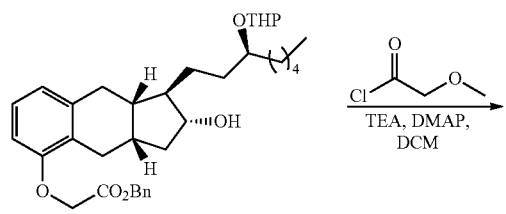

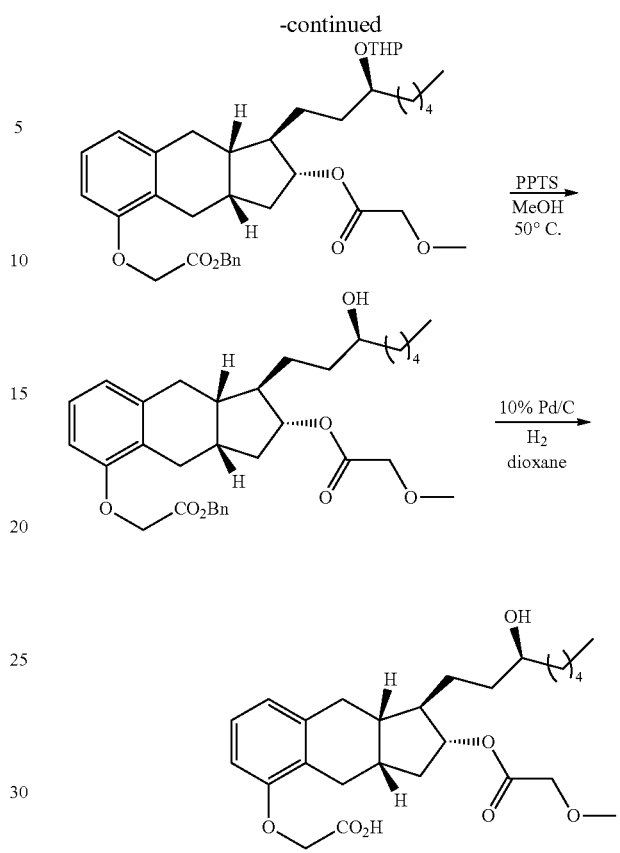

A solution of Compound C (90 mg, 0.15 mmol), NEt₃ (70 μL, 0.5 mmol) and 4-dimethylaminopyridine (DMAP) (1 crystal) in DCM (2 mL) was treated with methoxyacetyl chloride (21 μL, 0.22 mmol) and stirred at RT for 12 hr under nitrogen. The reaction mixture was diluted with MTBE and washed with water and then brine, dried over sodium sulfate and concentrated under vacuum. The residue was purified by silica gel chromatography. The THP-protected methoxyacetate was dissolved in MeOH (4 mL), treated with pyridinium para-toluene-sulfonate (PPTS) (catalytic) and stirred at 50° C. for 2 hr. The reaction mixture was concentrated, and the residue was dissolved in MTBE (20 mL) and washed with water and then brine to yield crude THP-deprotected methoxyacetate. The crude product was taken in dioxane (5 mL) along with 10% Pd/C (18 mg) and hydrogenated under a hydrogen atmosphere to yield crude Compound Ia-8 (64 mg) as an oil. MS: m/z 485 [M+Na]+

The following compounds were synthesized using similar procedures as above:

Compound Ia-1

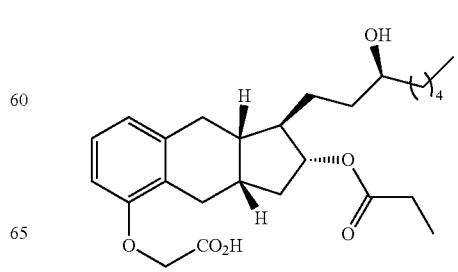

-continued

Compound Ia-2

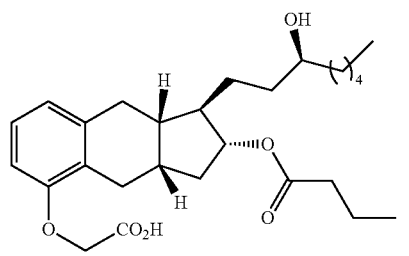

Compound Ia-3

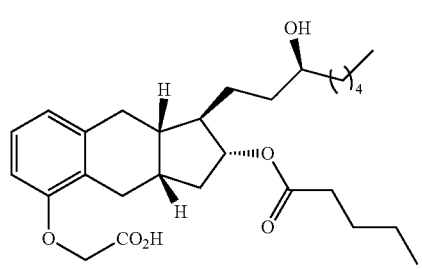

Compound Ia-9

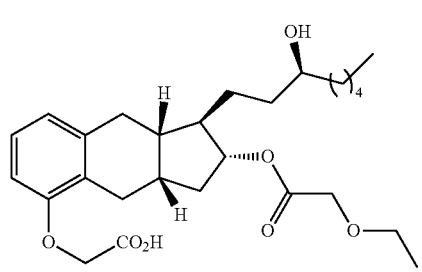

Compound Ia-11

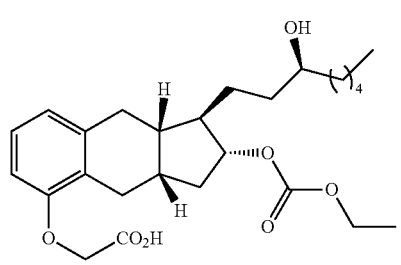

Example 4. Synthesis of [2-(2-hydroxyacetoxy)-1-(3-hydroxyoctyl)-2,3,3a,4,9,9a-hexahydro-1H-cyclopenta[b]naphthalen-5-yloxy]acetic Acid (Compound Ia-7)

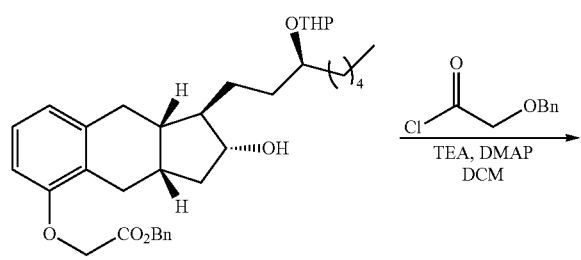

-continued

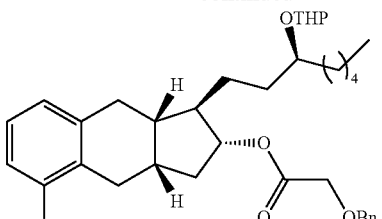

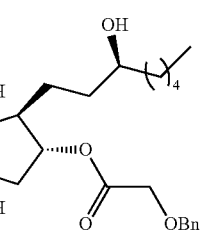

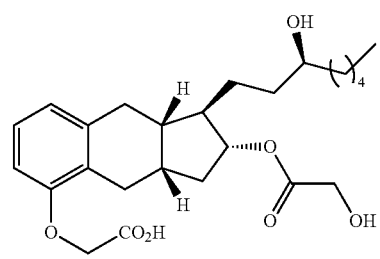

A solution of Compound C (100 mg, 0.177 mmol), NEt₃ (77 µL, 0.55 mmol) and DMAP (1 crystal) in DCM (2 mL) was treated with benzyloxyacetyl chloride (65 mg, 0.22 mmol) and stirred at RT for 12 hr under nitrogen. The reaction mixture was diluted with MTBE and washed with water and then brine, dried over sodium sulfate and concentrated under vacuum. The residue was purified by silica gel chromatography. The THP-protected benzyloxyacetate was dissolved in MeOH (4 mL), treated with PPTS (catalytic) and stirred at 50° C. for 2 hr. The reaction mixture was concentrated, and the residue was dissolved in MTBE (20 mL) and washed with water and then brine to yield crude THP-deprotected benzyloxyacetate. The crude product was taken in dioxane (5 mL) along with 10% Pd/C (24 mg) and hydrogenated under a hydrogen atmosphere to yield crude Compound Ia-7 (56 mg) as an oil. MS: m/z 471 [M+Na]⁺

Example 5. Synthesis of [1-(3-hydroxyoctyl)-2-methoxycarbonyloxy-2,3,3a,4,9,9a-hexahydro-1H-cyclopenta[b]naphthalen-5-yloxy]acetic Acid (Compound Ia-10)

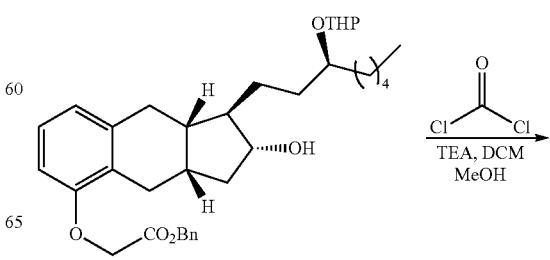

85

-continued

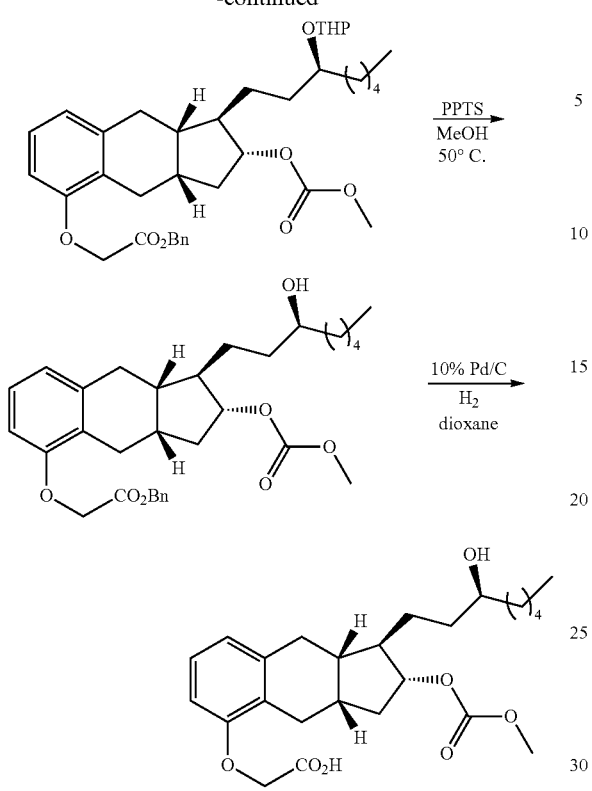

A solution of Compound C (160 mg, 0.28 mmol) and NEt₃ (798 µL, 2.8 mmol) in DCM (2 mL) was treated with phosgene solution (906 µL, 1.4 mmol, 0.5 M in toluene) at 0° C., and the resulting mixture was stirred at 0° C. for 0.5 hr under nitrogen. The reaction mixture was then added to MeOH (2 mL) at 0° C. and stirred for an additional 1 hr. The solvent was removed, and the residue was purified by silica gel chromatography. The THP-protected methylcarbonate was dissolved in MeOH (4 mL), treated with PPTS (catalytic) and stirred at 50° C. for 2 hr. The reaction mixture was concentrated, and the residue was dissolved in MTBE (20 mL) and washed with water and then brine to yield crude THP-deprotected methylcarbonate. The crude product was taken in dioxane (5 mL) along with 10% Pd/C (28 mg) and hydrogenated under a hydrogen atmosphere to yield crude Compound Ia-10 (83 mg) as an oil. MS: m/z 471 [M+Na]⁺

The following compound was synthesized using similar procedures as above:

Compound Ia-14

86

Synthesis of [2-benzyloxycarbonyloxy-1-(3-hydroxyoctyl)-2,3,3a,4,9,9a-hexahydro-1H-cyclopenta[b]naphthalen-5-yloxy]acetic Acid Benzyl Ester (Compound D)

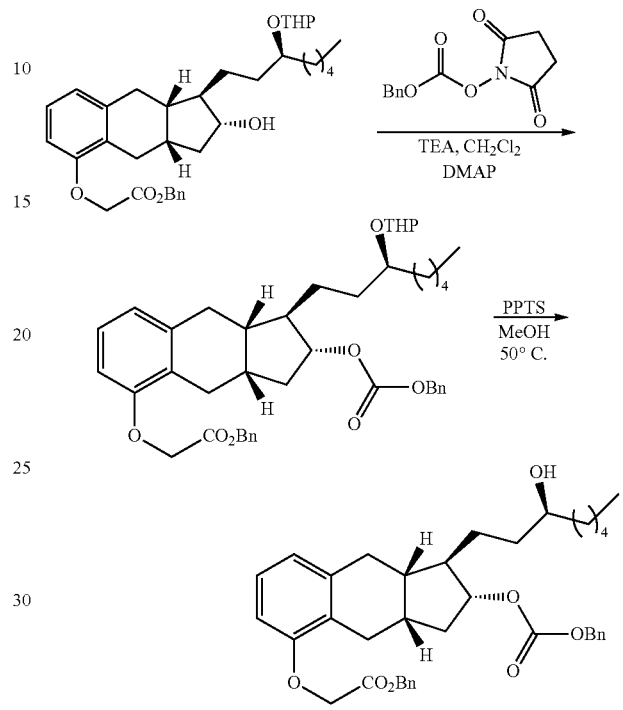

A solution of Compound C (100 mg, 0.177 mmol), NEt₃ (77 µL, 0.55 mmol) and DMAP (1 crystal) in DCM (2 mL) was treated with N-(benzyloxycarbonyloxy)succinimide (84 mg, 0.34 mmol) and stirred at RT for 24 hr under nitrogen. The reaction mixture was diluted with MTBE and washed with water and then brine, dried over sodium sulfate and concentrated under vacuum. The residue was purified by silica gel chromatography. The benzylcarbonate was dissolved in MeOH (4 mL), treated with PPTS (catalytic) and stirred at 50° C. for 2 hr. The reaction mixture was concentrated, and the residue was dissolved in MTBE (20 mL) and washed with water and then brine to yield crude Compound D (110 mg) as an oil.

Example 6. Synthesis of {2-hydroxy-1-[3-(2-methoxyacetoxy)octyl]-2,3,3a,4,9,9a-hexahydro-1H-cyclopenta[b]naphthalen-5-yloxy}acetic Acid (Compound Ib-8)

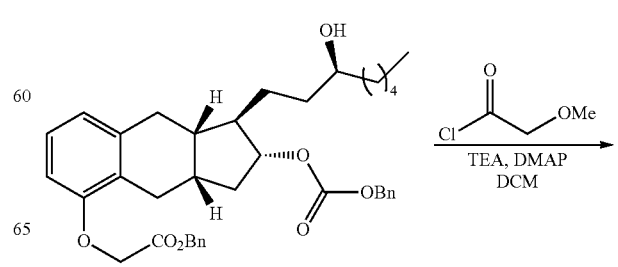

87

-continued

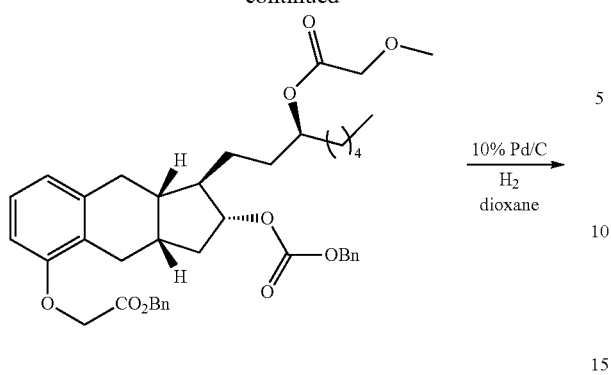

→ 10% Pd/C
H₂
dioxane

88

-continued

Compound Ib-2

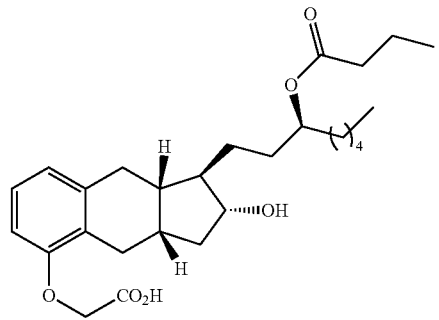

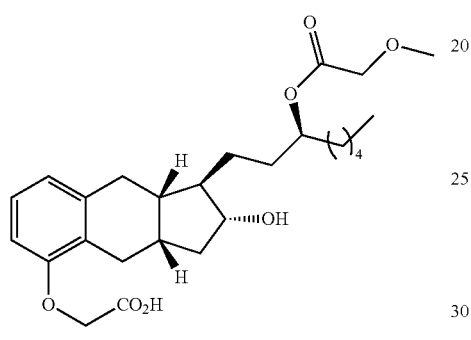

Compound Ib-3

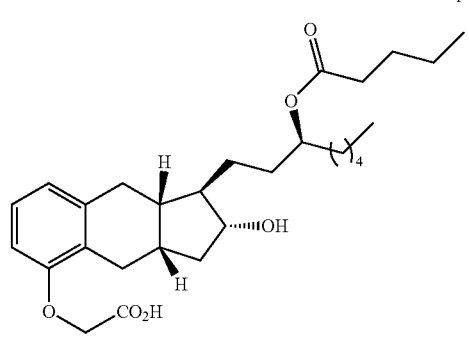

A solution of Compound D (70 mg, 0.11 mmol), NEt₃ (75 µL, 0.52 mmol) and DMAP (1 crystal) in DCM (2 mL) was treated with methoxyacetyl chloride (21 µL, 0.22 mmol) and stirred at 0° C. for 1 hr under nitrogen. The reaction mixture was diluted with MTBE and washed with water and then brine, dried over sodium sulfate and concentrated under vacuum. The residue was purified by silica gel chromatography. The methoxyacetate was taken in dioxane (5 mL) along with 10% Pd/C (16 mg) and hydrogenated under a hydrogen atmosphere to yield crude Compound Ib-8 (43 mg) as an oil. MS: m/z 485 [M+Na]⁺

The following compounds were synthesized using similar procedures as above:

Compound Ib-9

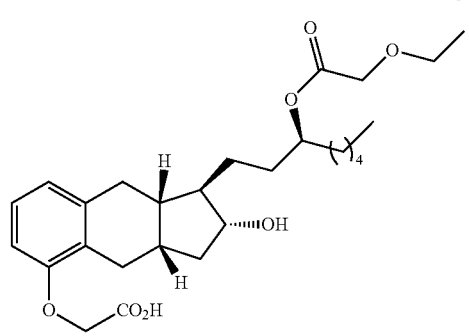

Compound Ib-1

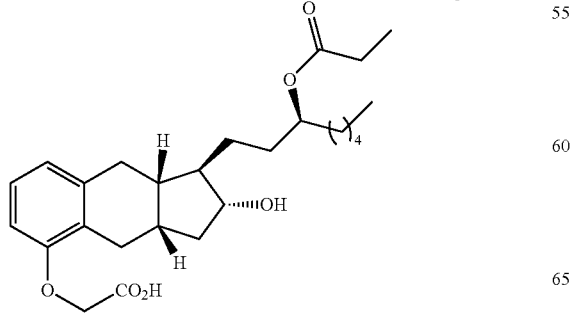

Compound Ib-10

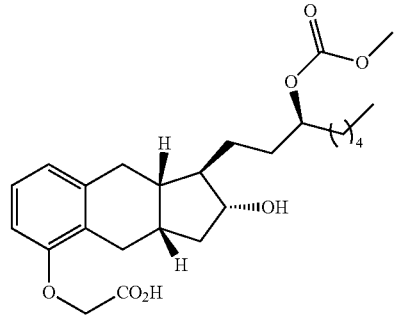

-continued

Compound Ib-11

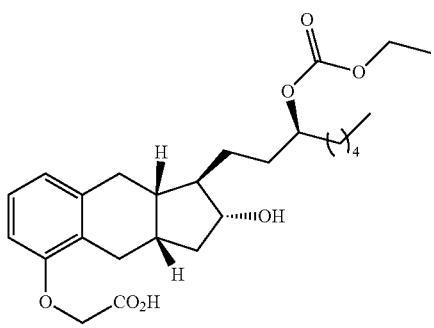

Example 7. Synthesis of 3-{2-[2-hydroxy-1-(3-hydroxyoctyl)-2,3,3a,4,9,9a-hexahydro-1H-cyclopenta[b]naphthalen-5-yloxy]acetoxy}propionic Acid (Compound 11-4)

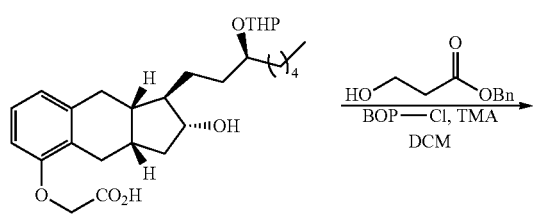

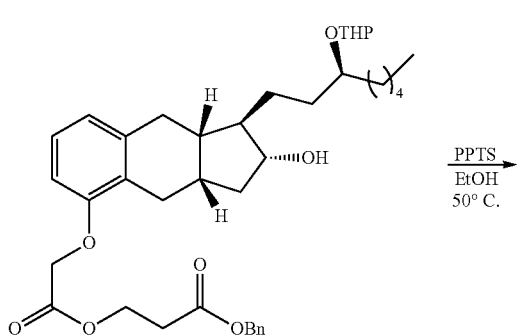

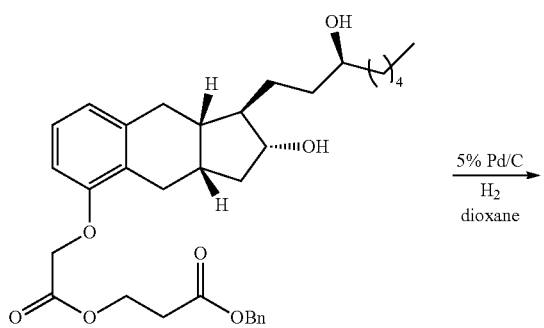

-continued

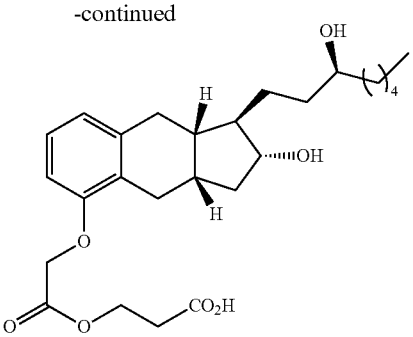

To a solution of Compound B (120 mg, 0.25 mmol), benzyl 3-hydroxypropionate (54 mg, 0.30 mmol) and trimethylamine (140 µL, 1.0 mmol) in DCM (4 mL) was added BOP-Cl (95 mg, 0.38 mmol). The reaction mixture was stirred at RT for 16 hr under nitrogen, diluted with MTBE, washed with brine, dried over sodium sulfate, and concentrated to an oil that was purified by silica gel chromatography. A solution of the THP-protected diester in ethanol (4 mL) was treated with PPTS (50 mg), stirred at 50° C. for 4 hr, and concentrated to an oil that was purified by silica gel chromatography. A solution of the THP-deprotected diester in dioxane (5 mL) was treated with wet 5% Pd/C (20 mg) and stirred for 24 hr under a balloon of hydrogen. The reaction mixture was filtered and concentrated to give crude Compound 11-4. MS: m/z 485 [M+Na]$^+$ The following compounds were synthesized using similar procedures as above:

Compound II-1

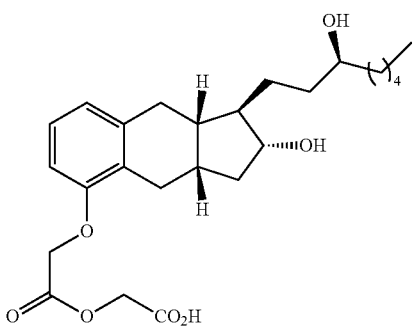

Compound II-2

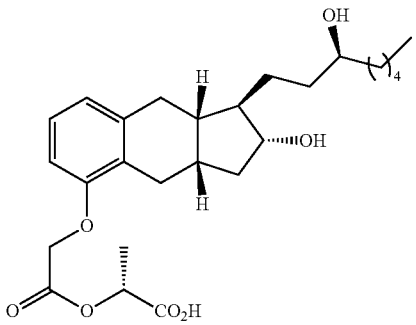

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

What is claimed is:

1. A pharmaceutical composition comprising one or more pharmaceutically acceptable excipients or carriers and a compound selected from the group consisting of:

Compound II-1
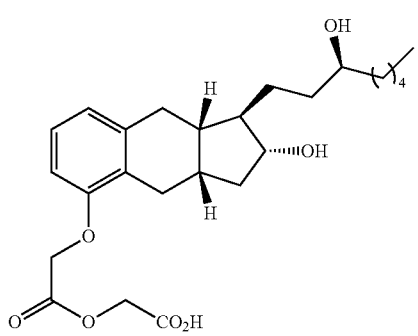

Compound II-2
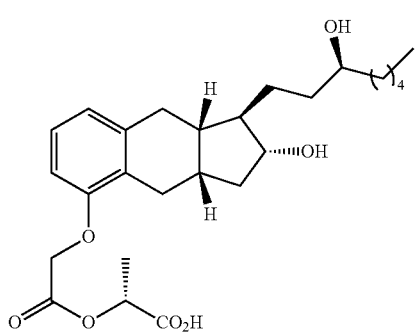

Compound II-3
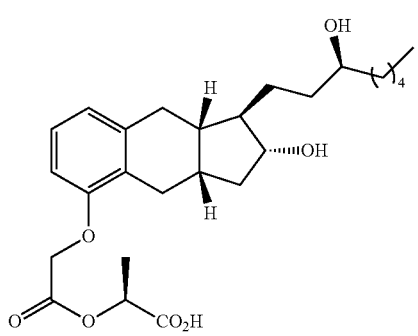

Compound II-4
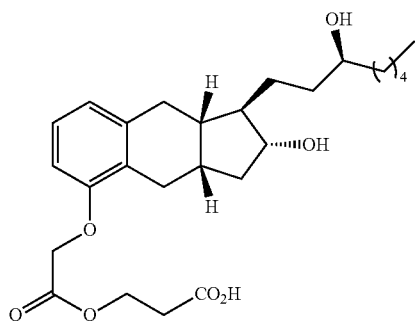

Compound II-5
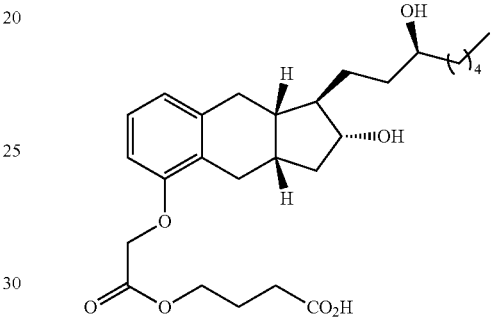

Compound II-6
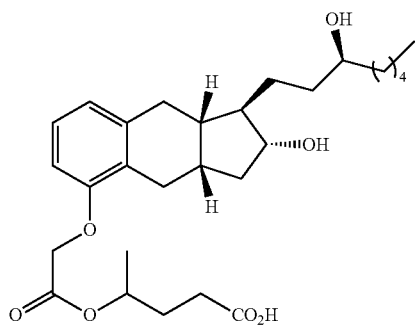

Compound II-7
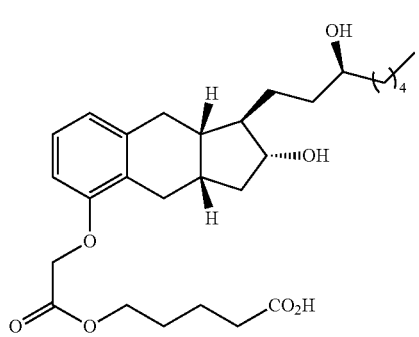

Compound II-8
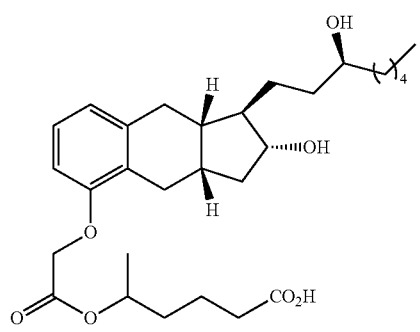
Compound II-9
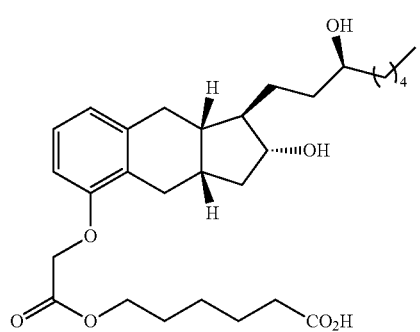
Compound II-10
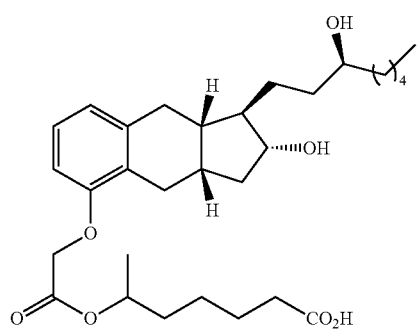
Compound II-11
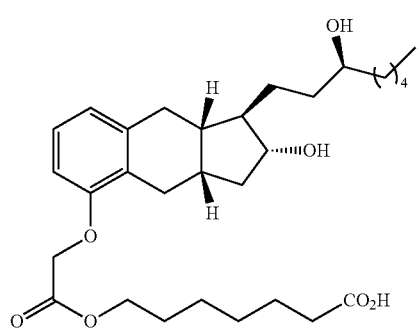
Compound II-12
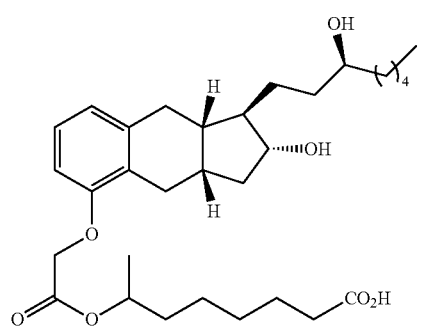
Compound II-13
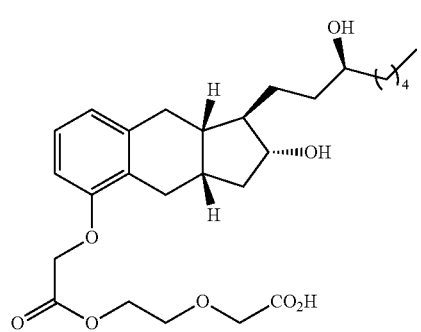
Compound II-14
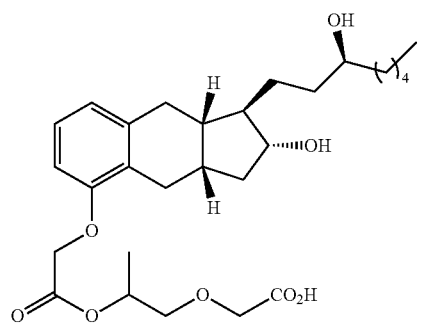
Compound II-15
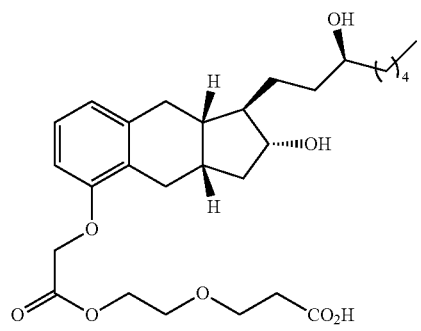

Compound II-16
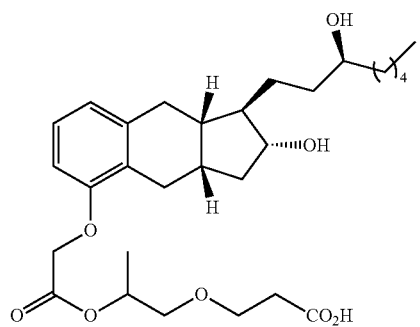
Compound II-17
Compound II-18
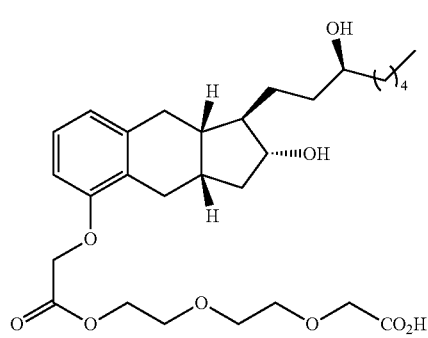
Compound II-19
Compound II-20
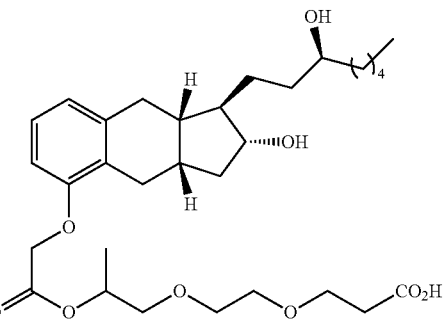
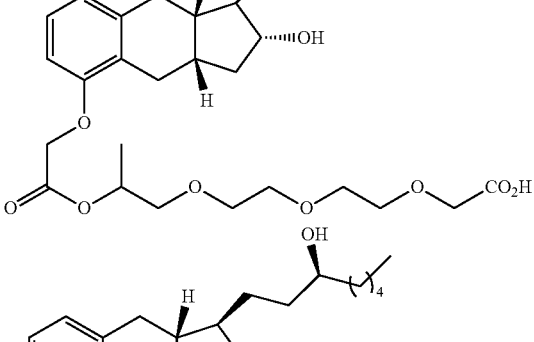
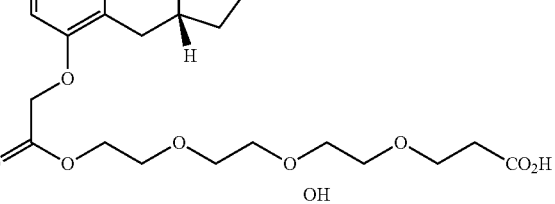
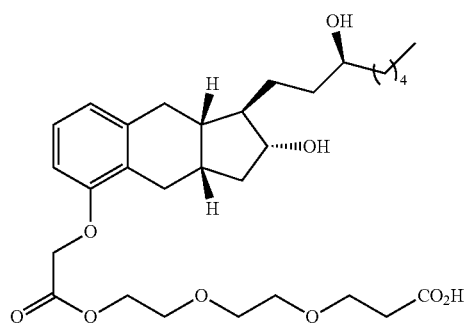

Compound II-21

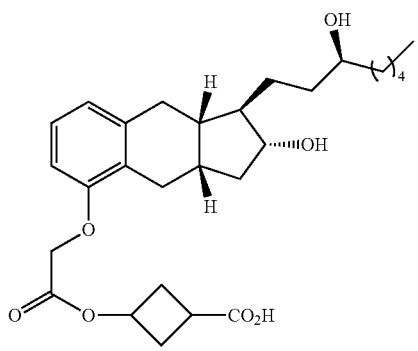

Compound II-25

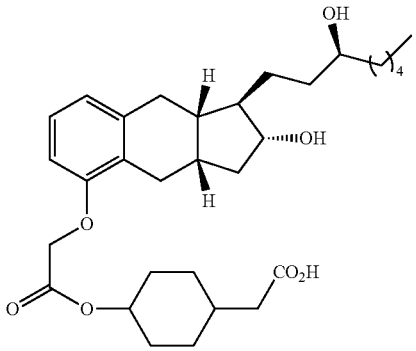

Compound II-22

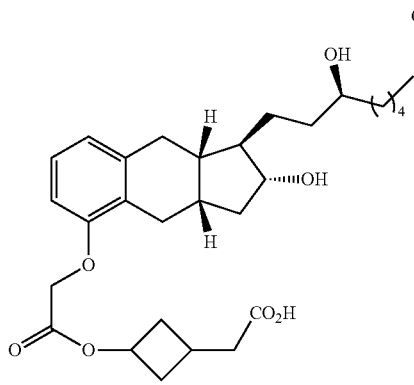

Compound II-26

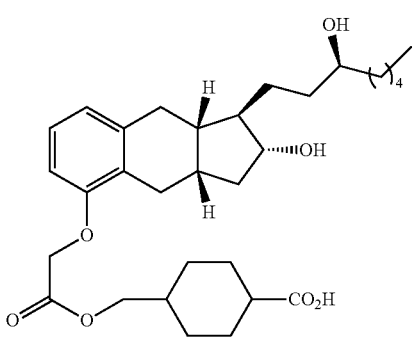

Compound II-23

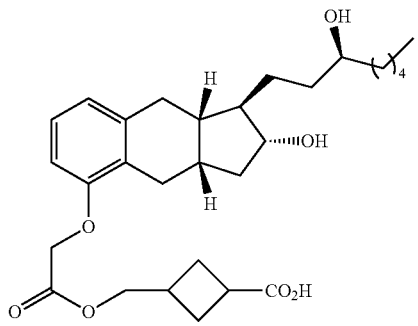

or a pharmaceutically acceptable salt, solvate, hydrate, clathrate, polymorph or stereoisomer thereof.

2. The pharmaceutical composition of claim 1, which is formulated for transdermal delivery of the compound.

3. The pharmaceutical composition of claim 2, which is configured as a transdermal patch.

4. A method of treating a medical condition responsive to treatment with treprostinil, comprising administering to a subject in need of treatment a therapeutically effective amount of a compound selected from the group consisting of:

Compound II-24

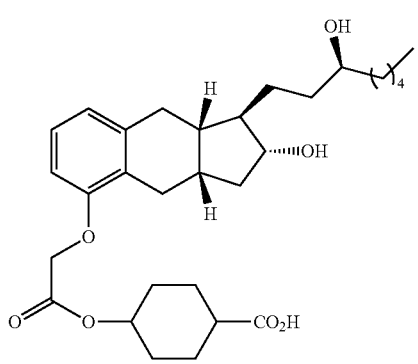

Compound II-1

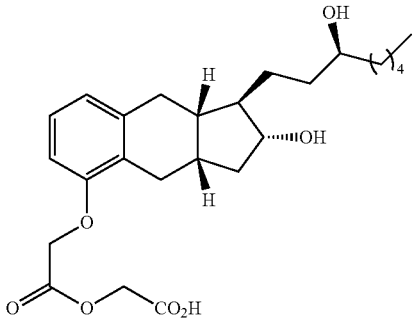

Compound II-2
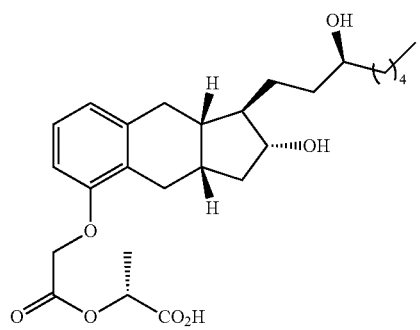
Compound II-3
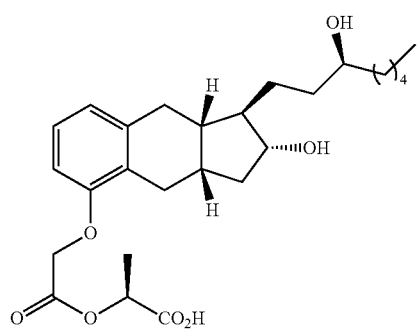
Compound II-4
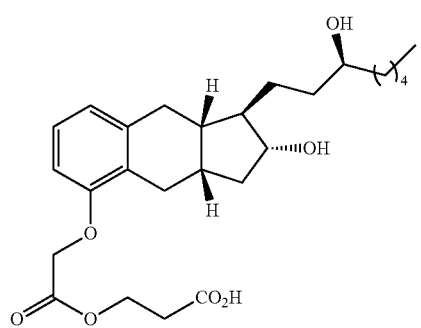
Compound II-5
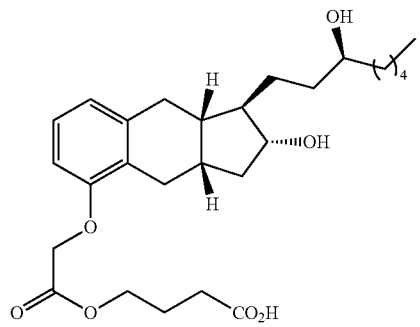
Compound II-6
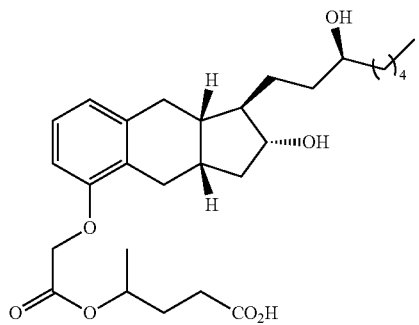
Compound II-7
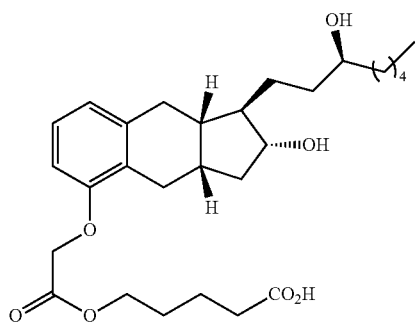
Compound II-8
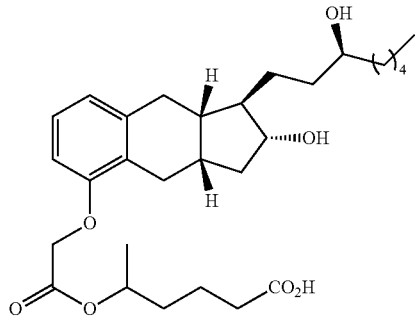
Compound II-9
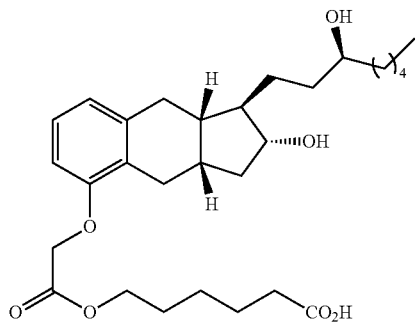

Compound II-10
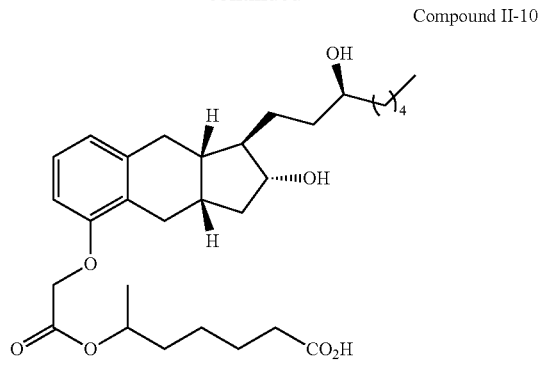
Compound II-11
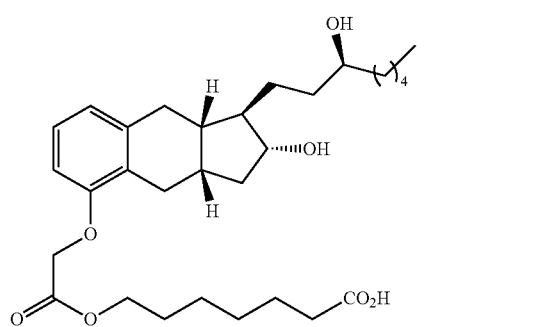
Compound II-12
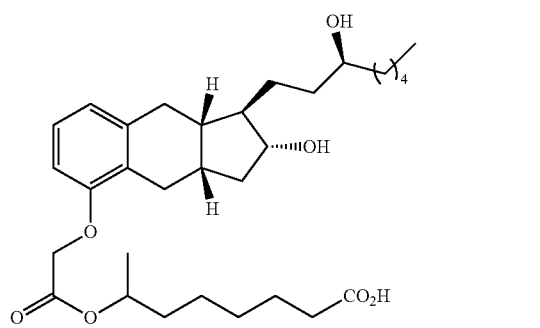
Compound II-13
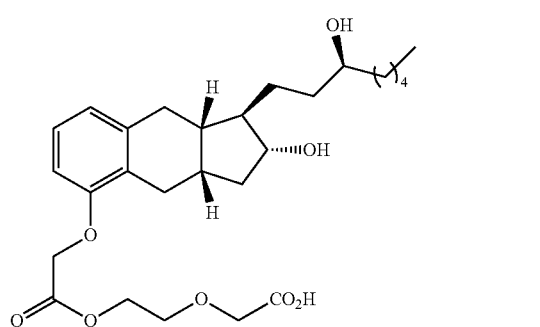
Compound II-14
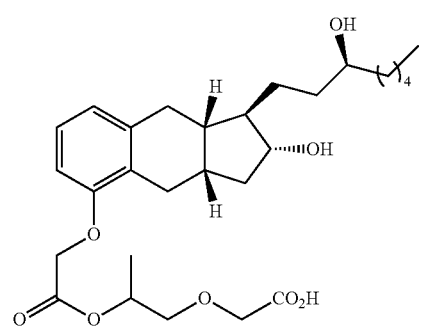
Compound II-15
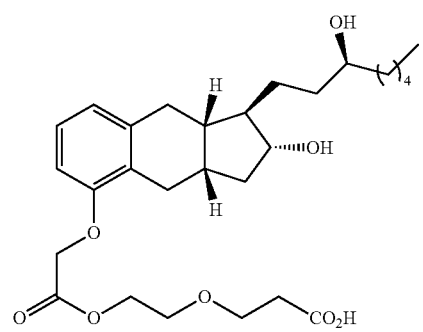
Compound II-16
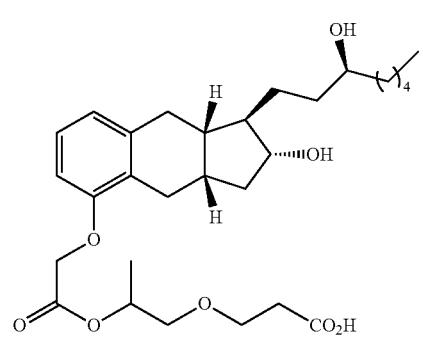
Compound II-17
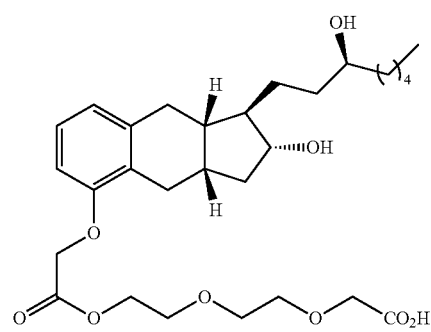

-continued
Compound II-18
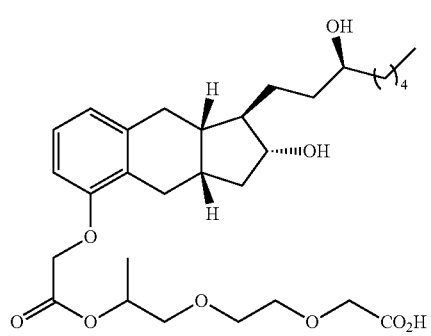
Compound II-19
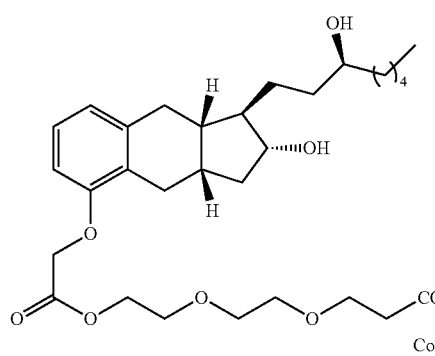
Compound II-20
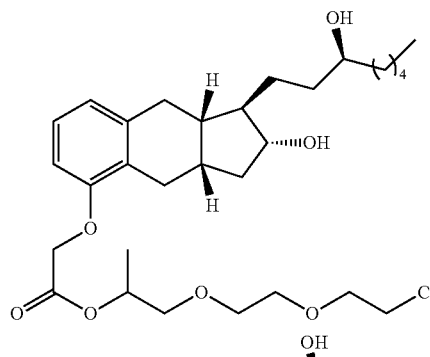
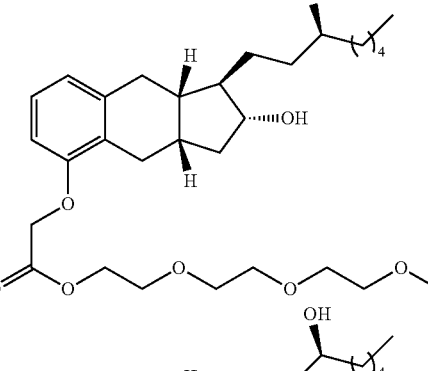
-continued
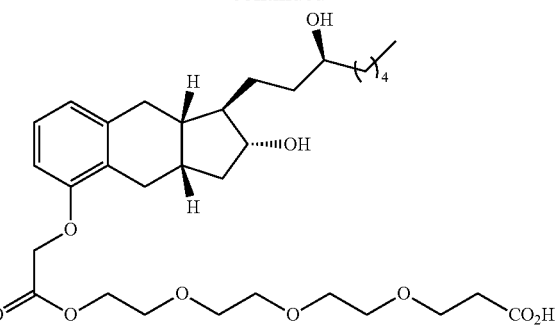
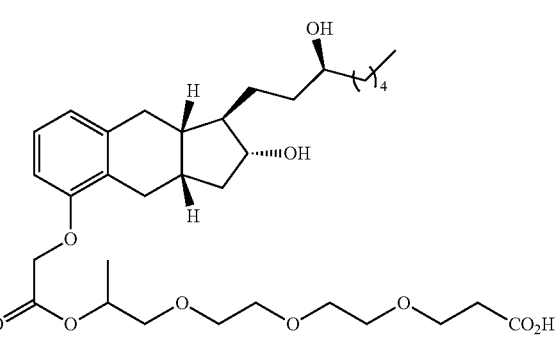
Compound II-21
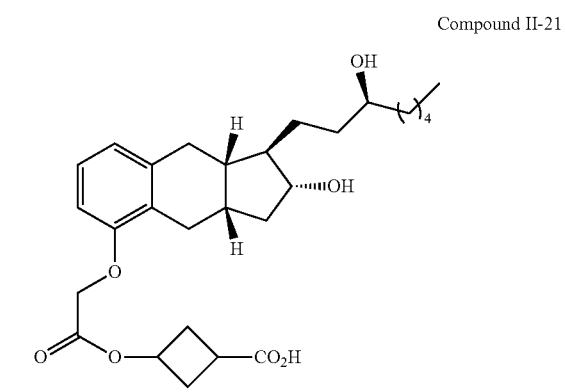
Compound II-22
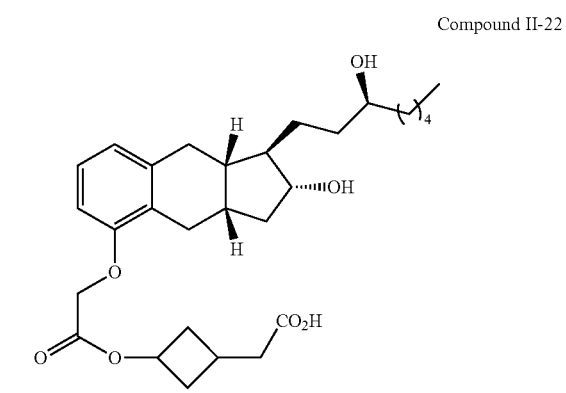

-continued

Compound II-23

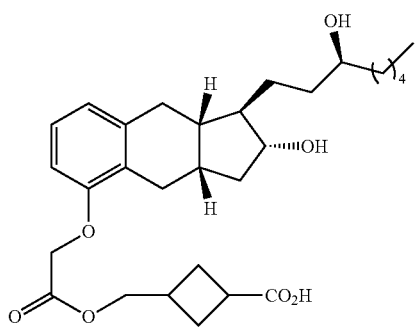

Compound II-24

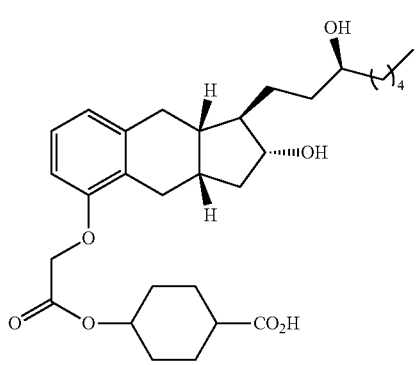

Compound II-25

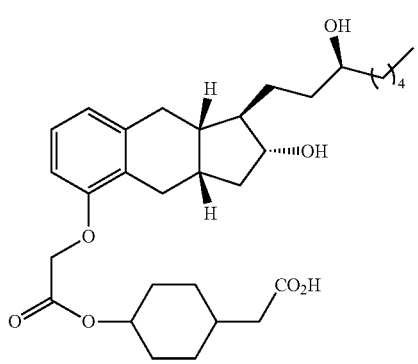

-continued

Compound II-26

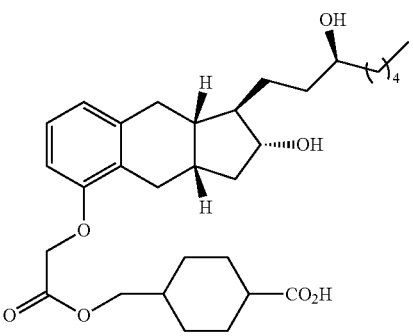

or a pharmaceutically acceptable salt, solvate, hydrate, clathrate, polymorph or stereoisomer thereof.

5. The method of claim 4, wherein the medical condition is selected from the group consisting of pulmonary hypertension, pulmonary fibrosis, ischemic diseases, peripheral vascular disease, peripheral ischemic lesions on the skin, critical limb ischemia, heart failure, atherogenesis, inflammatory diseases, diabetic neuropathic foot ulcer, kidney malfunction and failure, tumors, cancers, and pain associated with each of the preceding conditions.

6. The method of claim 5, wherein the medical condition is pulmonary hypertension.

7. The method of claim 6, wherein the medical condition is pulmonary arterial hypertension.

8. The method of claim 4, wherein the compound is administered topically.

9. The method of claim 8, wherein the compound is administered transdermally.

10. The method of claim 9, wherein the compound is administered via a transdermal patch.

11. The method of claim 8, wherein the compound is administered pulmonarily by oral inhalation.

12. The method of claim 4, wherein the compound is administered orally.

13. The method of claim 4, wherein the compound is administered parenterally.

14. The method of claim 13, wherein the compound is administered subcutaneously or intravenously.

15. The method of claim 4, further comprising administering an additional therapeutic agent.

16. The method of claim 15, wherein the additional therapeutic agent comprises a vasoactive agent, a diuretic, an anticoagulant or a cardiac glycoside, or any combination thereof.

* * * * *